United States Patent
Gilmore et al.

(10) Patent No.: US 9,801,720 B2
(45) Date of Patent: Oct. 31, 2017

(54) CARDIAC TISSUE CINCHING

(71) Applicant: 4TECH INC., Newton, MA (US)

(72) Inventors: Michael Gilmore, Ardrahan (IE); Paolo Denti, Milan (IT); Andrea Guidotti, Zurich (CH); Mohamed Azeem Latib, Milan (IT); Kevin Lynn, Athenry (IE); John Mullins, Tuam (IE); Francesco Maisano, Zurich (CH); David Zarbatany, Laguna Niguel, CA (US)

(73) Assignee: 4TECH INC., Waltham, MA (US)

( * ) Notice: Subject to any disclaimer, the term of this patent is extended or adjusted under 35 U.S.C. 154(b) by 0 days.

(21) Appl. No.: 15/123,157

(22) PCT Filed: Jun. 14, 2015

(86) PCT No.: PCT/IB2015/001196
§ 371 (c)(1),
(2) Date: Sep. 1, 2016

(87) PCT Pub. No.: WO2015/193728
PCT Pub. Date: Dec. 23, 2015

(65) Prior Publication Data
US 2017/0086975 A1 Mar. 30, 2017

Related U.S. Application Data

(60) Provisional application No. 62/131,636, filed on Mar. 11, 2015, provisional application No. 62/014,397, filed on Jun. 19, 2014.

(51) Int. Cl.
*A61F 2/24* (2006.01)
*A61B 17/00* (2006.01)
*A61B 17/04* (2006.01)

(52) U.S. Cl.
CPC ...... *A61F 2/2487* (2013.01); *A61B 17/00234* (2013.01); *A61B 17/0401* (2013.01);
(Continued)

(58) Field of Classification Search
CPC .... A61F 2/2487; A61F 2/2454; A61F 2/2457; A61F 2/2442–2/2451; A61B 17/0401;
(Continued)

(56) References Cited

U.S. PATENT DOCUMENTS 3,874,388 A * 4/1975 King ............... A61B 17/0057
606/213
4,214,349 A 7/1980 Munch
(Continued)

FOREIGN PATENT DOCUMENTS

DE 102007043830 4/2009
EP 1568326 8/2005
(Continued)

OTHER PUBLICATIONS

An Interview Summary dated Dec. 5, 2016, which issued during the prosecution of U.S. Appl. No. 13/574,088.
(Continued)

*Primary Examiner* — David C Eastwood
*Assistant Examiner* — Charles Wei
(74) *Attorney, Agent, or Firm* — UltimatEdge IP Law Group, P.C.; Dean G. Stathakis; Vito A. Canuso, III

(57) ABSTRACT

A method is provided including making an opening (300) through an atrial septum (302) at a septal site (304) at least 5 mm from a fossa ovalis (330). A first tissue anchor (204) is endovascularly advanced to a left-atrial site (306) on an annulus of a mitral valve (310) or a wall of a left atrium (308) above the annulus. The first tissue anchor (204) is implanted at the left-atrial site (306). A second tissue anchor (24) is endovascularly advanced to a right-atrial site (320)
(Continued)

on an annulus of a tricuspid valve (207) or a wall of a right atrium (200) above the annulus. The second tissue (24) anchor is implanted at the right-atrial site (320). The left-atrial site (306) and the right-atrial site (320) are approximated by tensioning a tether (22) that passes through the opening (300) of the atrial septum (302) and connects the first and the second tissue anchors (204, 24). Other embodiments are also described.

20 Claims, 36 Drawing Sheets

(52) U.S. Cl.
CPC ........ *A61B 17/0466* (2013.01); *A61F 2/2427* (2013.01); *A61B 2017/00243* (2013.01); *A61B 2017/0414* (2013.01); *A61B 2017/0454* (2013.01)

(58) Field of Classification Search
CPC ...... A61B 17/0057; A61B 2017/00243; A61B 2017/00247; A61B 2017/0419; A61B 2017/00606; A61B 2017/00575; A61B 2017/0409
USPC .................................................. 606/132, 232
See application file for complete search history.

(56) References Cited

U.S. PATENT DOCUMENTS

| | | |
|---|---|---|
| 4,405,313 A | 9/1983 | Sisley et al. |
| 4,423,525 A | 1/1984 | Vallana |
| 4,444,207 A | 4/1984 | Robicsek |
| 4,493,329 A | 1/1985 | Crawford et al. |
| 4,532,926 A | 8/1985 | O'Holla |
| 4,548,202 A | 10/1985 | Duncan |
| 4,602,911 A | 7/1986 | Ahmadi et al. |
| 4,625,727 A | 12/1986 | Leiboff |
| 4,712,549 A | 12/1987 | Peters et al. |
| 4,741,336 A | 5/1988 | Failla et al. |
| 4,778,468 A | 10/1988 | Hunt et al. |
| 4,808,157 A | 2/1989 | Coombs |
| 4,853,986 A | 8/1989 | Allen |
| 5,108,420 A | 4/1992 | Marks |
| 5,330,521 A | 7/1994 | Cohen |
| 5,336,233 A | 8/1994 | Chen |
| 5,350,399 A | 9/1994 | Erlebacher et al. |
| 5,450,860 A | 9/1995 | O'Connor |
| 5,473,812 A | 12/1995 | Morris et al. |
| 5,474,518 A | 12/1995 | Farrer-Velazquez |
| 5,776,178 A | 7/1998 | Pohndorf et al. |
| 5,792,400 A | 8/1998 | Talja et al. |
| 5,843,120 A | 12/1998 | Israel |
| 5,843,164 A | 12/1998 | Frantzen et al. |
| 5,904,697 A | 5/1999 | Gifford et al. |
| 5,948,000 A | 9/1999 | Larsen et al. |
| 5,957,953 A | 9/1999 | Dipoto et al. |
| 5,961,440 A | 10/1999 | Schweich, Jr. et al. |
| 6,010,113 A | 1/2000 | Rotering |
| 6,024,756 A * | 2/2000 | Huebsch ............ A61B 17/0057 606/213 |
| 6,027,523 A | 2/2000 | Schmieding |
| 6,045,497 A | 4/2000 | Schweich, Jr. et al. |
| 6,050,936 A | 4/2000 | Schweich, Jr. et al. |
| 6,077,214 A * | 6/2000 | Mortier ............ A61B 17/00234 128/898 |
| 6,183,512 B1 | 2/2001 | Howanec et al. |
| 6,193,734 B1 | 2/2001 | Bolduc et al. |
| 6,206,913 B1 | 3/2001 | Yencho et al. |
| 6,210,432 B1 | 4/2001 | Solem et al. |
| 6,231,516 B1 | 5/2001 | Keilman et al. |
| 6,298,272 B1 | 10/2001 | Peterfeso et al. |
| 6,299,635 B1 | 10/2001 | Frantzen |
| 6,332,893 B1 | 12/2001 | Mortier et al. |
| 6,338,738 B1 | 1/2002 | Bellotti et al. |
| 6,402,780 B2 | 6/2002 | Williamson, IV et al. |
| 6,402,781 B1 | 6/2002 | Langberg et al. |
| 6,406,420 B1 * | 6/2002 | McCarthy ........ A61B 17/00234 600/16 |
| 6,461,336 B1 | 10/2002 | Larre |
| 6,533,810 B2 | 3/2003 | Hankh et al. |
| 6,537,198 B1 | 3/2003 | Vidlund et al. |
| 6,537,314 B2 | 3/2003 | Langberg et al. |
| 6,575,976 B2 | 6/2003 | Grafton |
| 6,585,766 B1 | 7/2003 | Huynh et al. |
| 6,602,288 B1 | 8/2003 | Cosgrove et al. |
| 6,613,078 B1 | 9/2003 | Barone |
| 6,613,079 B1 | 9/2003 | Wolinsky |
| 6,616,684 B1 * | 9/2003 | Vidlund ........... A61B 17/00234 606/213 |
| 6,619,291 B2 | 9/2003 | Hlavka et al. |
| 6,622,730 B2 | 9/2003 | Ekvall et al. |
| 6,626,899 B2 | 9/2003 | Houser et al. |
| 6,626,930 B1 | 9/2003 | Allen et al. |
| 6,629,534 B1 * | 10/2003 | St. Goar ............ A61B 17/0469 128/898 |
| 6,629,921 B1 | 10/2003 | Schweich, Jr. et al. |
| 6,641,597 B2 | 11/2003 | Burkhart et al. |
| 6,645,193 B2 | 11/2003 | Mangosong |
| 6,702,846 B2 | 3/2004 | Mikus |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 * | 4/2004 | Schroeder ........ A61B 17/00234 600/16 |
| 6,730,118 B2 | 5/2004 | Spenser et al. |
| 6,743,198 B1 | 6/2004 | Tihon |
| 6,746,472 B2 | 6/2004 | Frazier et al. |
| 6,764,510 B2 * | 7/2004 | Vidlund ........... A61B 17/00234 623/2.34 |
| 6,776,754 B1 * | 8/2004 | Wilk ................ A61B 17/00234 128/898 |
| 6,797,001 B2 | 9/2004 | Mathis |
| 6,810,882 B2 | 11/2004 | Langberg et al. |
| 6,884,250 B2 | 4/2005 | Monassevitch |
| 6,893,459 B1 | 5/2005 | Macoviak |
| 6,908,478 B2 | 6/2005 | Alferness et al. |
| 6,929,660 B1 | 8/2005 | Ainsworth et al. |
| 6,989,028 B2 | 1/2006 | Lashinski et al. |
| 6,997,951 B2 | 2/2006 | Solem et al. |
| 7,011,682 B2 | 3/2006 | Lashinski et al. |
| 7,018,406 B2 | 3/2006 | Seguin et al. |
| 7,018,408 B2 | 3/2006 | Bailey et al. |
| 7,037,290 B2 | 5/2006 | Gardeski et al. |
| 7,041,097 B1 | 5/2006 | Webler |
| 7,044,967 B1 | 5/2006 | Solem et al. |
| 7,060,021 B1 * | 6/2006 | Wilk ................ A61B 17/00234 128/898 |
| 7,063,711 B1 | 6/2006 | Loshakove et al. |
| 7,077,861 B2 | 7/2006 | Spence |
| 7,083,628 B2 | 8/2006 | Bachman |
| 7,087,064 B1 | 8/2006 | Hyde |
| 7,094,244 B2 | 8/2006 | Schreck |
| 7,101,395 B2 | 9/2006 | Tremulis et al. |
| 7,101,396 B2 | 9/2006 | Artof et al. |
| 7,112,219 B2 | 9/2006 | Vidlund et al. |
| 7,125,421 B2 | 10/2006 | Tremulis et al. |
| 7,144,363 B2 | 12/2006 | Pai et al. |
| 7,159,593 B2 | 1/2007 | McCarthy et al. |
| 7,166,127 B2 | 1/2007 | Spence et al. |
| 7,169,187 B2 | 1/2007 | Datta |
| 7,175,625 B2 | 2/2007 | Culbert |
| 7,179,282 B2 | 2/2007 | Alferness et al. |
| 7,186,262 B2 | 3/2007 | Saadat |
| 7,189,199 B2 | 3/2007 | McCarthy et al. |
| 7,192,442 B2 | 3/2007 | Solem et al. |
| 7,192,443 B2 | 3/2007 | Solem et al. |
| 7,198,646 B2 | 4/2007 | Figulla et al. |
| 7,201,772 B2 | 4/2007 | Schwammenthal |
| 7,211,107 B2 | 5/2007 | Bruckheimer et al. |
| 7,211,110 B2 | 5/2007 | Rowe et al. |
| 7,241,257 B1 | 7/2007 | Ainsworth et al. |

(56) References Cited

U.S. PATENT DOCUMENTS

| | | | |
|---|---|---|---|
| 7,247,134 B2 | 7/2007 | Vidlund et al. | |
| 7,258,697 B1 | 8/2007 | Cox et al. | |
| 7,291,168 B2 | 11/2007 | MacOviak et al. | |
| 7,311,697 B2 | 12/2007 | Osborne | |
| 7,311,728 B2 | 12/2007 | Solem et al. | |
| 7,316,706 B2 | 1/2008 | Bloom et al. | |
| 7,316,710 B1 | 1/2008 | Cheng et al. | |
| 7,329,279 B2 | 2/2008 | Haug et al. | |
| 7,331,972 B1 | 2/2008 | Cox | |
| 7,335,213 B1 | 2/2008 | Hyde et al. | |
| 7,338,506 B2 | 3/2008 | Caro | |
| 7,351,256 B2 | 4/2008 | Hojeibane | |
| 7,371,244 B2 | 5/2008 | Chatlynne et al. | |
| 7,374,573 B2 | 5/2008 | Gabbay | |
| 7,381,210 B2 | 6/2008 | Zarbatany et al. | |
| 7,381,220 B2 | 6/2008 | MacOviak et al. | |
| 7,390,329 B2 | 6/2008 | Westra et al. | |
| 7,431,692 B2 | 10/2008 | Zollinger et al. | |
| 7,431,726 B2 | 10/2008 | Spence et al. | |
| 7,485,143 B2 | 2/2009 | Webler et al. | |
| 7,500,989 B2 | 3/2009 | Solem et al. | |
| 7,503,931 B2 | 3/2009 | Kowalsky et al. | |
| 7,510,575 B2 | 3/2009 | Spenser et al. | |
| 7,527,646 B2 | 5/2009 | Randert et al. | |
| 7,530,995 B2 | 5/2009 | Quijano et al. | |
| 7,547,321 B2 | 6/2009 | Silvestri et al. | |
| 7,549,983 B2 | 6/2009 | Roue et al. | |
| 7,597,703 B2 | 10/2009 | Sater | |
| 7,608,102 B2 | 10/2009 | Adams et al. | |
| 7,618,449 B2 | 11/2009 | Tremulis et al. | |
| 7,628,797 B2 | 12/2009 | Tieu et al. | |
| 7,632,303 B1 | 12/2009 | Stalker et al. | |
| 7,637,946 B2 | 12/2009 | Solem et al. | |
| 7,666,204 B2 | 2/2010 | Thornton et al. | |
| 7,695,512 B2 | 4/2010 | Lashinski et al. | |
| 7,704,277 B2 | 4/2010 | Zakay et al. | |
| 7,722,523 B2 | 5/2010 | Mortier et al. | |
| 7,758,632 B2 | 7/2010 | Hojeibane et al. | |
| 7,766,816 B2 * | 8/2010 | Chin | A61B 17/0401 600/37 |
| 7,771,467 B2 | 8/2010 | Svensson | |
| 7,780,726 B2 | 8/2010 | Seguin | |
| 7,785,366 B2 | 8/2010 | Maurer et al. | |
| 7,803,187 B2 | 9/2010 | Hauser | |
| 7,806,910 B2 | 10/2010 | Anderson | |
| 7,837,727 B2 | 11/2010 | Goetz et al. | |
| 7,841,502 B2 | 11/2010 | Walberg et al. | |
| 7,857,846 B2 | 12/2010 | Alferness et al. | |
| 7,871,433 B2 | 1/2011 | Lattouf | |
| 7,883,539 B2 | 2/2011 | Schweich, Jr. et al. | |
| 7,930,016 B1 * | 4/2011 | Saadat | A61B 1/0008 600/101 |
| 7,942,927 B2 | 5/2011 | Kaye et al. | |
| 7,947,207 B2 | 5/2011 | Mcniven et al. | |
| 7,972,378 B2 | 7/2011 | Tabor et al. | |
| 7,991,484 B1 | 8/2011 | Sengupta et al. | |
| 7,992,567 B2 | 8/2011 | Hirotsuka | |
| 7,993,368 B2 | 8/2011 | Gambale et al. | |
| 7,993,397 B2 | 8/2011 | Lashinski et al. | |
| 8,010,207 B2 | 8/2011 | Smits et al. | |
| 8,025,495 B2 | 9/2011 | Hardert et al. | |
| 8,029,518 B2 | 10/2011 | Goldfarb et al. | |
| 8,052,592 B2 | 11/2011 | Goldfarb et al. | |
| 8,075,616 B2 | 12/2011 | Solem et al. | |
| 8,092,520 B2 | 1/2012 | Quadri | |
| 8,092,525 B2 | 1/2012 | Eliasen et al. | |
| 8,100,820 B2 | 1/2012 | Hauser et al. | |
| 8,108,054 B2 | 1/2012 | Helland | |
| 8,109,996 B2 | 2/2012 | Stacchino et al. | |
| 8,137,381 B2 | 3/2012 | Foerster et al. | |
| 8,142,493 B2 | 3/2012 | Spence et al. | |
| 8,142,495 B2 | 3/2012 | Hasenkam et al. | |
| 8,147,542 B2 | 4/2012 | Maisano et al. | |
| 8,157,810 B2 | 4/2012 | Case et al. | |
| 8,172,898 B2 | 5/2012 | Alferness et al. | |
| 8,197,441 B2 | 6/2012 | Webler et al. | |
| 8,202,281 B2 | 6/2012 | Voss | |
| 8,202,315 B2 | 6/2012 | Hlavka et al. | |
| 8,216,302 B2 | 7/2012 | Wilson et al. | |
| 8,226,707 B2 | 7/2012 | White | |
| 8,236,013 B2 | 8/2012 | Chu | |
| 8,236,049 B2 | 8/2012 | Rowe et al. | |
| 8,252,005 B2 | 8/2012 | Findlay et al. | |
| 8,262,567 B2 | 9/2012 | Sharp et al. | |
| 8,262,724 B2 | 9/2012 | Seguin et al. | |
| 8,262,725 B2 | 9/2012 | Subramanian | |
| 8,267,981 B2 | 9/2012 | Boock et al. | |
| 8,313,497 B2 | 11/2012 | Walberg et al. | |
| 8,313,498 B2 | 11/2012 | Pantages et al. | |
| 8,323,312 B2 | 12/2012 | Clark | |
| 8,323,335 B2 | 12/2012 | Rowe et al. | |
| 8,332,051 B2 | 12/2012 | Sommer et al. | |
| 8,361,088 B2 | 1/2013 | McIntosh | |
| 8,382,829 B1 | 2/2013 | Call et al. | |
| 8,394,008 B2 * | 3/2013 | Annest | A61B 17/00234 600/16 |
| 8,398,672 B2 | 3/2013 | Kleshinski et al. | |
| 8,409,273 B2 | 4/2013 | Thornton et al. | |
| 8,419,753 B2 | 4/2013 | Stafford | |
| 8,430,893 B2 | 4/2013 | Ma | |
| 8,449,606 B2 | 5/2013 | Eliasen et al. | |
| 8,460,368 B2 | 6/2013 | Taylor et al. | |
| 8,460,371 B2 | 6/2013 | Hlavka et al. | |
| 8,475,525 B2 | 7/2013 | Maisano et al. | |
| 8,480,691 B2 | 7/2013 | Dana et al. | |
| 8,480,730 B2 | 7/2013 | Maurer et al. | |
| 8,523,881 B2 | 9/2013 | Cabiri et al. | |
| 8,524,132 B2 | 9/2013 | Von Oepen et al. | |
| 8,529,621 B2 | 9/2013 | Alfieri et al. | |
| 8,545,553 B2 | 10/2013 | Zipory et al. | |
| 8,568,475 B2 | 10/2013 | Nguyen et al. | |
| 8,568,476 B2 | 10/2013 | Rao et al. | |
| 8,591,460 B2 | 11/2013 | Wilson et al. | |
| 8,597,347 B2 | 12/2013 | Maurer et al. | |
| 8,628,569 B2 | 1/2014 | Benichou et al. | |
| 8,628,571 B1 | 1/2014 | Hacohen | |
| 8,663,248 B2 | 3/2014 | Zung et al. | |
| 8,685,080 B2 | 4/2014 | White | |
| 8,685,083 B2 | 4/2014 | Perier et al. | |
| 8,721,588 B2 | 5/2014 | Echarri et al. | |
| 8,728,097 B1 | 5/2014 | Sugimoto et al. | |
| 8,747,463 B2 | 6/2014 | Fogarty et al. | |
| 8,753,357 B2 | 6/2014 | Roorda et al. | |
| 8,753,373 B2 | 6/2014 | Chau et al. | |
| 8,778,017 B2 | 7/2014 | Eliasen et al. | |
| 8,784,481 B2 | 7/2014 | Alkhatib et al. | |
| 8,790,394 B2 | 7/2014 | Miller et al. | |
| 8,795,356 B2 | 8/2014 | Quadri et al. | |
| 8,808,366 B2 | 8/2014 | Braido et al. | |
| 8,808,368 B2 | 8/2014 | Maisano et al. | |
| 8,845,723 B2 | 9/2014 | Spence et al. | |
| 8,852,270 B2 | 10/2014 | Maurer et al. | |
| 8,852,272 B2 | 10/2014 | Gross et al. | |
| 8,858,594 B2 | 10/2014 | Clark | |
| 8,858,623 B2 | 10/2014 | Miller et al. | |
| 8,864,822 B2 | 10/2014 | Spence et al. | |
| 8,870,949 B2 | 10/2014 | Rowe | |
| 8,870,950 B2 | 10/2014 | Hacohen | |
| 8,893,947 B2 | 11/2014 | Reynolds et al. | |
| 8,911,461 B2 | 12/2014 | Traynor et al. | |
| 8,926,691 B2 | 1/2015 | Chau et al. | |
| 8,945,177 B2 | 2/2015 | Dell et al. | |
| 8,945,211 B2 | 2/2015 | Sugimoto | |
| 8,951,285 B2 | 2/2015 | Sugimoto et al. | |
| 8,961,594 B2 | 2/2015 | Maisano et al. | |
| 8,961,595 B2 | 2/2015 | Alkhatib | |
| 8,961,596 B2 | 2/2015 | Maisano et al. | |
| 8,968,335 B2 | 3/2015 | Robinson et al. | |
| 8,968,336 B2 | 3/2015 | Conklin et al. | |
| 8,968,395 B2 | 3/2015 | Hauser et al. | |
| 8,979,750 B2 * | 3/2015 | Van Bladel | A61B 17/00 600/213 |
| 8,979,922 B2 | 3/2015 | Jayasinghe et al. | |
| 8,979,923 B2 | 3/2015 | Spence et al. | |

(56) References Cited

U.S. PATENT DOCUMENTS

| | | | |
|---|---|---|---|
| 9,005,273 B2 | 4/2015 | Salahieh et al. |
| 9,011,468 B2 | 4/2015 | Ketai et al. |
| 9,017,347 B2 | 4/2015 | Oba et al. |
| 9,034,032 B2 | 5/2015 | McLean et al. |
| 9,034,033 B2 | 5/2015 | McLean et al. |
| 9,078,652 B2 | 7/2015 | Conklin et al. |
| 9,084,676 B2 | 7/2015 | Chau et al. |
| 9,107,749 B2 | 8/2015 | Bobo et al. |
| 9,131,939 B1 | 9/2015 | Call et al. |
| 9,138,335 B2 | 9/2015 | Cartledge et al. |
| 9,180,005 B1 | 11/2015 | Lashinski et al. |
| 9,192,471 B2 | 11/2015 | Bolling |
| 9,211,115 B2 * | 12/2015 | Annest ............... A61B 17/0401 |
| 9,211,203 B2 | 12/2015 | Pike et al. |
| 9,241,702 B2 | 1/2016 | Maisano et al. |
| 9,241,706 B2 | 1/2016 | Paraschac et al. |
| 9,259,218 B2 | 2/2016 | Robinson |
| 9,259,317 B2 | 2/2016 | Wilson et al. |
| 9,282,965 B2 | 3/2016 | Kokish |
| 9,289,282 B2 | 3/2016 | Olson et al. |
| 9,289,297 B2 | 3/2016 | Wilson et al. |
| 9,301,749 B2 | 4/2016 | Rowe et al. |
| 9,314,242 B2 | 4/2016 | Bachman |
| 9,326,870 B2 | 5/2016 | Berglund et al. |
| 9,358,111 B2 | 6/2016 | Spence et al. |
| 9,408,607 B2 | 8/2016 | Cartledge et al. |
| 9,474,605 B2 | 10/2016 | Rowe et al. |
| 9,662,212 B2 * | 5/2017 | Van Bladel ............ A61F 2/2487 |
| 2001/0018611 A1 * | 8/2001 | Solem ................... A61F 2/2451 623/2.37 |
| 2002/0013571 A1 | 1/2002 | Goldfarb et al. |
| 2002/0032481 A1 | 5/2002 | Gabbay |
| 2002/0082625 A1 | 6/2002 | Huxel et al. |
| 2002/0107564 A1 | 8/2002 | Cox et al. |
| 2002/0151961 A1 | 10/2002 | Lashinski et al. |
| 2002/0156517 A1 | 10/2002 | Perouse |
| 2002/0177904 A1 | 11/2002 | Huxel et al. |
| 2003/0033003 A1 | 2/2003 | Harrison et al. |
| 2003/0057156 A1 | 3/2003 | Peterson et al. |
| 2003/0083742 A1 | 5/2003 | Spence et al. |
| 2003/0093096 A1 | 5/2003 | McGuckin, Jr. et al. |
| 2003/0167071 A1 | 9/2003 | Martin et al. |
| 2003/0229350 A1 | 12/2003 | Kay |
| 2003/0236568 A1 | 12/2003 | Hojeibane et al. |
| 2004/0117009 A1 | 6/2004 | Cali et al. |
| 2004/0133274 A1 | 7/2004 | Webler et al. |
| 2004/0172046 A1 | 9/2004 | Hlavka et al. |
| 2004/0181287 A1 | 9/2004 | Gellman |
| 2004/0186566 A1 | 9/2004 | Hindrichs et al. |
| 2004/0193092 A1 | 9/2004 | Deal |
| 2004/0236419 A1 | 11/2004 | Milo |
| 2004/0260389 A1 | 12/2004 | Case et al. |
| 2005/0004668 A1 | 1/2005 | Aklog et al. |
| 2005/0016560 A1 | 1/2005 | Voughlohn |
| 2005/0021085 A1 | 1/2005 | Abrams et al. |
| 2005/0055089 A1 | 3/2005 | Macoviak et al. |
| 2005/0059984 A1 * | 3/2005 | Chanduszko ....... A61B 17/0057 606/151 |
| 2005/0059997 A1 | 3/2005 | Bauman et al. |
| 2005/0075723 A1 | 4/2005 | Schroeder et al. |
| 2005/0080483 A1 | 4/2005 | Solem et al. |
| 2005/0090827 A1 | 4/2005 | Gedebou |
| 2005/0096666 A1 | 5/2005 | Gordon et al. |
| 2005/0107812 A1 | 5/2005 | Starksen et al. |
| 2005/0107871 A1 | 5/2005 | Realyvasquez et al. |
| 2005/0113900 A1 | 5/2005 | Shiroff et al. |
| 2005/0125077 A1 | 6/2005 | Harmon et al. |
| 2005/0137688 A1 | 6/2005 | Salahieh et al. |
| 2005/0137695 A1 | 6/2005 | Salahieh et al. |
| 2005/0149182 A1 * | 7/2005 | Alferness ............... A61F 2/2466 623/2.36 |
| 2005/0154448 A1 | 7/2005 | Cully et al. |
| 2005/0177180 A1 | 8/2005 | Kaganov et al. |
| 2005/0177228 A1 | 8/2005 | Solem |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222488 A1 * | 10/2005 | Chang ............... A61B 17/00234 600/37 |
| 2005/0222665 A1 | 10/2005 | Arayani |
| 2005/0228422 A1 * | 10/2005 | Machold .......... A61B 17/00234 606/167 |
| 2005/0251208 A1 | 11/2005 | Elmer et al. |
| 2005/0256532 A1 | 11/2005 | Nayak et al. |
| 2005/0273138 A1 | 12/2005 | To et al. |
| 2005/0283246 A1 | 12/2005 | Cauthen et al. |
| 2006/0004442 A1 | 1/2006 | Spenser et al. |
| 2006/0020326 A9 | 1/2006 | Bolduc et al. |
| 2006/0020327 A1 | 1/2006 | Lashinski et al. |
| 2006/0052821 A1 | 3/2006 | Abbot et al. |
| 2006/0079736 A1 * | 4/2006 | Chin ................... A61B 17/0401 600/151 |
| 2006/0106278 A1 * | 5/2006 | MacHold ......... A61B 17/00234 600/37 |
| 2006/0106279 A1 * | 5/2006 | MacHold ......... A61B 17/00234 600/37 |
| 2006/0106420 A1 | 5/2006 | Dolan et al. |
| 2006/0106423 A1 | 5/2006 | Weisel et al. |
| 2006/0129166 A1 | 6/2006 | Lavelle |
| 2006/0161265 A1 | 7/2006 | Levine et al. |
| 2006/0173524 A1 | 8/2006 | Salahieh et al. |
| 2006/0178700 A1 | 8/2006 | Quinn |
| 2006/0200199 A1 | 9/2006 | Bonutti et al. |
| 2006/0206201 A1 | 9/2006 | Garcia et al. |
| 2006/0229708 A1 | 10/2006 | Powell et al. |
| 2006/0241745 A1 | 10/2006 | Solem |
| 2006/0241748 A1 | 10/2006 | Lee et al. |
| 2006/0252984 A1 * | 11/2006 | Rahdert ............. A61B 17/0401 600/37 |
| 2006/0259135 A1 | 11/2006 | Navia et al. |
| 2006/0259137 A1 | 11/2006 | Artof et al. |
| 2006/0265042 A1 * | 11/2006 | Catanese, III ..... A61B 17/0401 623/1.11 |
| 2006/0276871 A1 | 12/2006 | Lamson et al. |
| 2006/0282161 A1 | 12/2006 | Huynh et al. |
| 2007/0016287 A1 | 1/2007 | Cartledge |
| 2007/0016288 A1 | 1/2007 | Gurskis et al. |
| 2007/0021781 A1 | 1/2007 | Jervis et al. |
| 2007/0032787 A1 * | 2/2007 | Hassett ............... A61B 18/1492 606/41 |
| 2007/0032796 A1 * | 2/2007 | Chin-Chen ........ A61B 17/0057 606/139 |
| 2007/0032820 A1 * | 2/2007 | Chin-Chen ........ A61B 17/0057 606/213 |
| 2007/0038221 A1 | 2/2007 | Fine et al. |
| 2007/0038296 A1 | 2/2007 | Navia |
| 2007/0049942 A1 | 3/2007 | Hindrichs et al. |
| 2007/0049970 A1 | 3/2007 | Belef et al. |
| 2007/0049971 A1 * | 3/2007 | Chin ................. A61B 17/0401 606/232 |
| 2007/0051377 A1 | 3/2007 | Douk et al. |
| 2007/0055340 A1 | 3/2007 | Pryor |
| 2007/0060895 A1 | 3/2007 | Sibbitt et al. |
| 2007/0060989 A1 | 3/2007 | Deem et al. |
| 2007/0061010 A1 | 3/2007 | Hauser et al. |
| 2007/0066863 A1 | 3/2007 | Rafiee et al. |
| 2007/0083168 A1 | 4/2007 | Whiting et al. |
| 2007/0093869 A1 | 4/2007 | Bloom et al. |
| 2007/0100427 A1 | 5/2007 | Perouse |
| 2007/0112425 A1 | 5/2007 | Schaller et al. |
| 2007/0118151 A1 | 5/2007 | Davidson |
| 2007/0123936 A1 | 5/2007 | Goldin et al. |
| 2007/0162107 A1 | 7/2007 | Haug et al. |
| 2007/0168013 A1 | 7/2007 | Douglas |
| 2007/0185532 A1 | 8/2007 | Stone et al. |
| 2007/0198082 A1 | 8/2007 | Kapadia et al. |
| 2007/0203391 A1 | 8/2007 | Bloom et al. |
| 2007/0208389 A1 | 9/2007 | Amundson et al. |
| 2007/0219558 A1 | 9/2007 | Deutsch |
| 2007/0250160 A1 | 10/2007 | Rafiee |
| 2007/0265658 A1 * | 11/2007 | Nelson ............. A61B 17/00234 606/213 |
| 2007/0265700 A1 | 11/2007 | Eliasen et al. |

(56) References Cited

U.S. PATENT DOCUMENTS

| | | |
|---|---|---|
| 2007/0270943 A1 | 11/2007 | Solem et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0288086 A1 | 12/2007 | Kalmann et al. |
| 2007/0288089 A1 | 12/2007 | Gurskis et al. |
| 2008/0003539 A1 | 1/2008 | Lundgren |
| 2008/0015617 A1 | 1/2008 | Harari et al. |
| 2008/0027268 A1 | 1/2008 | Buckner et al. |
| 2008/0027446 A1 | 1/2008 | Stone et al. |
| 2008/0027483 A1 | 1/2008 | Cartledge |
| 2008/0033475 A1* | 2/2008 | Meng ............... A61B 17/0057 606/191 |
| 2008/0035160 A1 | 2/2008 | Woodson et al. |
| 2008/0058866 A1 | 3/2008 | Young et al. |
| 2008/0077231 A1 | 3/2008 | Heringes et al. |
| 2008/0091264 A1* | 4/2008 | Machold ............ A61B 17/0057 623/2.1 |
| 2008/0097595 A1 | 4/2008 | Gabbay |
| 2008/0125861 A1 | 5/2008 | Webler et al. |
| 2008/0140116 A1 | 6/2008 | Bonutti |
| 2008/0140188 A1 | 6/2008 | Randert et al. |
| 2008/0167714 A1 | 7/2008 | St. Goar |
| 2008/0190989 A1 | 8/2008 | Crews et al. |
| 2008/0262598 A1 | 10/2008 | Elmaleh |
| 2008/0262609 A1 | 10/2008 | Gross et al. |
| 2008/0275469 A1 | 11/2008 | Fanton et al. |
| 2008/0281411 A1 | 11/2008 | Berreklouw et al. |
| 2008/0288044 A1 | 11/2008 | Osborne |
| 2008/0288062 A1 | 11/2008 | Andrieu et al. |
| 2008/0300629 A1 | 12/2008 | Surti |
| 2009/0005863 A1 | 1/2009 | Goetz et al. |
| 2009/0043382 A1 | 2/2009 | Maurer et al. |
| 2009/0048668 A1 | 2/2009 | Wilson et al. |
| 2009/0082828 A1 | 3/2009 | Ostroff |
| 2009/0082847 A1 | 3/2009 | Zacharias et al. |
| 2009/0084386 A1 | 4/2009 | McClellan et al. |
| 2009/0099647 A1 | 4/2009 | Glimsdale et al. |
| 2009/0099649 A1 | 4/2009 | Chobotov et al. |
| 2009/0112052 A1 | 4/2009 | Lund et al. |
| 2009/0118776 A1 | 5/2009 | Kelsch et al. |
| 2009/0131849 A1 | 5/2009 | Maurer et al. |
| 2009/0132033 A1 | 5/2009 | Maurer et al. |
| 2009/0143808 A1 | 6/2009 | Houser |
| 2009/0149872 A1 | 6/2009 | Gross et al. |
| 2009/0171439 A1 | 7/2009 | Nissl |
| 2009/0216265 A1 | 8/2009 | Devries |
| 2009/0240326 A1 | 9/2009 | Wilson et al. |
| 2009/0254103 A1 | 10/2009 | Deutsch et al. |
| 2009/0259307 A1 | 10/2009 | Gross et al. |
| 2009/0264991 A1 | 10/2009 | Paul et al. |
| 2009/0264995 A1 | 10/2009 | Subramanian |
| 2009/0276040 A1 | 11/2009 | Rowe et al. |
| 2009/0287304 A1 | 11/2009 | Dahlgren et al. |
| 2009/0306622 A1 | 12/2009 | Machold et al. |
| 2009/0326648 A1 | 12/2009 | Machold et al. |
| 2010/0022948 A1 | 1/2010 | Wilson et al. |
| 2010/0023117 A1 | 1/2010 | Yoganathan et al. |
| 2010/0023118 A1 | 1/2010 | Medlock et al. |
| 2010/0029071 A1 | 2/2010 | Russell et al. |
| 2010/0030329 A1 | 2/2010 | Frater |
| 2010/0049293 A1 | 2/2010 | Zukowski et al. |
| 2010/0063520 A1 | 3/2010 | Bilotti |
| 2010/0063542 A1 | 3/2010 | Van Der Burg et al. |
| 2010/0063586 A1 | 3/2010 | Hasenkam et al. |
| 2010/0121349 A1 | 5/2010 | Meier et al. |
| 2010/0121434 A1 | 5/2010 | Paul et al. |
| 2010/0121435 A1 | 5/2010 | Subramanian et al. |
| 2010/0130992 A1 | 5/2010 | Machold et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168791 A1 | 7/2010 | Kassab |
| 2010/0174358 A1 | 7/2010 | Rabkin |
| 2010/0185278 A1* | 7/2010 | Schankereli ..... A61B 17/00234 623/2.36 |
| 2010/0204662 A1 | 8/2010 | Orlov et al. |
| 2010/0211166 A1 | 8/2010 | Miller et al. |
| 2010/0217382 A1 | 8/2010 | Chau et al. |
| 2010/0228269 A1 | 9/2010 | Garrison et al. |
| 2010/0234935 A1 | 9/2010 | Bashiri |
| 2010/0249908 A1 | 9/2010 | Chau et al. |
| 2010/0249920 A1 | 9/2010 | Bolling et al. |
| 2010/0264192 A1 | 10/2010 | Marczyk |
| 2010/0268204 A1 | 10/2010 | Tieu et al. |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0286767 A1 | 11/2010 | Zipory et al. |
| 2010/0298930 A1 | 11/2010 | Orlov |
| 2010/0324598 A1 | 12/2010 | Anderson |
| 2010/0324668 A1 | 12/2010 | Maurer et al. |
| 2011/0004296 A1 | 1/2011 | Lutter et al. |
| 2011/0009818 A1 | 1/2011 | Goff |
| 2011/0011917 A1 | 1/2011 | Loulmet |
| 2011/0022164 A1 | 1/2011 | Quinn et al. |
| 2011/0029066 A1 | 2/2011 | Gilad |
| 2011/0029071 A1 | 2/2011 | Zlotnick et al. |
| 2011/0035000 A1 | 2/2011 | Nieminen et al. |
| 2011/0040366 A1 | 2/2011 | Goetz et al. |
| 2011/0071626 A1 | 3/2011 | Wright et al. |
| 2011/0077733 A1 | 3/2011 | Solem |
| 2011/0082538 A1 | 4/2011 | Dahlgren et al. |
| 2011/0087146 A1 | 4/2011 | Ryan et al. |
| 2011/0092993 A1 | 4/2011 | Jacobs |
| 2011/0093002 A1 | 4/2011 | Rucker et al. |
| 2011/0098732 A1 | 4/2011 | Jacobs |
| 2011/0106245 A1 | 5/2011 | Miller et al. |
| 2011/0106247 A1 | 5/2011 | Miller et al. |
| 2011/0112619 A1 | 5/2011 | Foster et al. |
| 2011/0112632 A1 | 5/2011 | Chau et al. |
| 2011/0137397 A1 | 6/2011 | Chau et al. |
| 2011/0152998 A1 | 6/2011 | Berez et al. |
| 2011/0166636 A1 | 7/2011 | Rowe |
| 2011/0184510 A1* | 7/2011 | Maisano ............ A61B 17/0401 623/1.24 |
| 2011/0190879 A1 | 8/2011 | Bobo et al. |
| 2011/0208283 A1 | 8/2011 | Rust et al. |
| 2011/0224785 A1 | 9/2011 | Hacohen |
| 2011/0238088 A1 | 9/2011 | Bolduc et al. |
| 2011/0238112 A1 | 9/2011 | Kim et al. |
| 2011/0251678 A1 | 10/2011 | Eidenschink |
| 2011/0264208 A1 | 10/2011 | Duffy et al. |
| 2011/0301698 A1 | 12/2011 | Miller et al. |
| 2012/0016343 A1 | 1/2012 | Gill |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0143320 A1 | 1/2012 | Eliasen et al. |
| 2012/0035712 A1 | 2/2012 | Maisano |
| 2012/0083806 A1 | 4/2012 | Goertzen |
| 2012/0123531 A1 | 5/2012 | Tsukashima et al. |
| 2012/0130374 A1 | 5/2012 | Bouduban et al. |
| 2012/0130421 A1 | 5/2012 | Hafez et al. |
| 2012/0158053 A1 | 6/2012 | Paulos |
| 2012/0179244 A1 | 7/2012 | Schankereli et al. |
| 2012/0215236 A1 | 8/2012 | Matsunaga et al. |
| 2012/0222969 A1 | 9/2012 | Osborne et al. |
| 2012/0226349 A1 | 9/2012 | Tuval et al. |
| 2012/0232373 A1 | 9/2012 | Hallander et al. |
| 2012/0245604 A1 | 9/2012 | Tegzes |
| 2012/0283757 A1 | 11/2012 | Miller et al. |
| 2012/0296349 A1 | 11/2012 | Smith et al. |
| 2012/0310328 A1 | 12/2012 | Olson et al. |
| 2013/0030522 A1* | 1/2013 | Rowe ................ A61B 17/0401 623/2.36 |
| 2013/0041459 A1 | 2/2013 | Wilson et al. |
| 2013/0053951 A1 | 2/2013 | Baliarda |
| 2013/0085529 A1 | 4/2013 | Housman |
| 2013/0096664 A1 | 4/2013 | Goetz et al. |
| 2013/0096672 A1 | 4/2013 | Reich et al. |

(56) References Cited

U.S. PATENT DOCUMENTS

| | | | |
|---|---|---|---|
| 2013/0110230 A1* | 5/2013 | Solem | A61F 2/2466 623/2.38 |
| 2013/0166017 A1 | 6/2013 | Cartledge et al. | |
| 2013/0166022 A1 | 6/2013 | Conklin | |
| 2013/0172978 A1 | 7/2013 | Vidlund et al. | |
| 2013/0190863 A1* | 7/2013 | Call | A61B 17/0401 623/2.36 |
| 2013/0281760 A1* | 10/2013 | Farnan | A61M 1/3653 600/16 |
| 2013/0296925 A1 | 11/2013 | Chanduszko et al. | |
| 2013/0325110 A1 | 12/2013 | Khalil et al. | |
| 2013/0331930 A1 | 12/2013 | Rowe et al. | |
| 2014/0005778 A1 | 1/2014 | Buchbinder et al. | |
| 2014/0018911 A1 | 1/2014 | Zhou et al. | |
| 2014/0031864 A1 | 1/2014 | Jafari et al. | |
| 2014/0031928 A1 | 1/2014 | Murphy et al. | |
| 2014/0058405 A1 | 2/2014 | Foster | |
| 2014/0066693 A1 | 3/2014 | Goldfarb et al. | |
| 2014/0067054 A1 | 3/2014 | Chau et al. | |
| 2014/0114390 A1 | 4/2014 | Tobis et al. | |
| 2014/0121763 A1 | 5/2014 | Duffy et al. | |
| 2014/0142689 A1 | 5/2014 | De Canniere et al. | |
| 2014/0163690 A1 | 6/2014 | White | |
| 2014/0200657 A1 | 7/2014 | Maurer et al. | |
| 2014/0207231 A1 | 7/2014 | Hacohen et al. | |
| 2014/0214159 A1 | 7/2014 | Vidlund et al. | |
| 2014/0243894 A1 | 8/2014 | Groothuis et al. | |
| 2014/0257475 A1 | 9/2014 | Gross et al. | |
| 2014/0275757 A1 | 9/2014 | Goodwin et al. | |
| 2014/0277390 A1 | 9/2014 | Ratz et al. | |
| 2014/0277427 A1 | 9/2014 | Ratz et al. | |
| 2014/0288639 A1 | 9/2014 | Gainor | |
| 2014/0296962 A1 | 10/2014 | Cartledge et al. | |
| 2014/0309730 A1 | 10/2014 | Alon et al. | |
| 2014/0324164 A1 | 10/2014 | Gross et al. | |
| 2014/0358224 A1 | 12/2014 | Tegels et al. | |
| 2014/0371843 A1 | 12/2014 | Wilson et al. | |
| 2014/0379006 A1 | 12/2014 | Sutherland et al. | |
| 2014/0379074 A1 | 12/2014 | Spence et al. | |
| 2014/0379076 A1 | 12/2014 | Vidlund et al. | |
| 2015/0018940 A1 | 1/2015 | Quill et al. | |
| 2015/0045879 A1 | 2/2015 | Longoria et al. | |
| 2015/0051698 A1 | 2/2015 | Baliarda et al. | |
| 2015/0066082 A1* | 3/2015 | Moshe | A61B 17/0401 606/232 |
| 2015/0066138 A1 | 3/2015 | Alexander et al. | |
| 2015/0073545 A1 | 3/2015 | Braido | |
| 2015/0094800 A1 | 4/2015 | Chawla | |
| 2015/0094802 A1 | 4/2015 | Buchbinder et al. | |
| 2015/0100116 A1 | 4/2015 | Mohl et al. | |
| 2015/0119936 A1 | 4/2015 | Gilmore et al. | |
| 2015/0127097 A1 | 5/2015 | Neumann et al. | |
| 2015/0142049 A1 | 5/2015 | Delgado et al. | |
| 2015/0142103 A1 | 5/2015 | Vidlund | |
| 2015/0142105 A1 | 5/2015 | Bolling et al. | |
| 2015/0182336 A1 | 7/2015 | Zipory et al. | |
| 2015/0196693 A1 | 7/2015 | Lin | |
| 2015/0223934 A1 | 8/2015 | Vidlund et al. | |
| 2015/0250590 A1 | 9/2015 | Gries et al. | |
| 2015/0272730 A1 | 10/2015 | Melnick et al. | |
| 2015/0320414 A1 | 11/2015 | Conklin et al. | |
| 2015/0351909 A1 | 12/2015 | Bobo et al. | |
| 2016/0022417 A1 | 1/2016 | Karapetian et al. | |
| 2016/0022422 A1* | 1/2016 | Annest | A61B 17/00234 606/232 |
| 2016/0038285 A1 | 2/2016 | Glenn et al. | |
| 2016/0081829 A1 | 3/2016 | Rowe | |
| 2016/0120672 A1 | 5/2016 | Martin et al. | |
| 2016/0128689 A1 | 5/2016 | Sutherland et al. | |
| 2016/0157862 A1 | 6/2016 | Hernandez et al. | |
| 2016/0174979 A1 | 6/2016 | Wei | |
| 2016/0228246 A1 | 8/2016 | Zimmerman | |
| 2016/0228252 A1 | 8/2016 | Keidar | |
| 2016/0235526 A1 | 8/2016 | Lashinski et al. | |
| 2016/0242762 A1 | 8/2016 | Gilmore et al. | |
| 2016/0256269 A1 | 9/2016 | Cahalane et al. | |
| 2016/0262741 A1 | 9/2016 | Gilmore et al. | |
| 2016/0270776 A1 | 9/2016 | Miraki et al. | |
| 2016/0270916 A1 | 9/2016 | Cahalane et al. | |
| 2016/0287383 A1 | 10/2016 | Rowe | |
| 2016/0287387 A1 | 10/2016 | Wei | |

FOREIGN PATENT DOCUMENTS

| | | |
|---|---|---|
| EP | 1397176 | 3/2007 |
| EP | 1759663 | 3/2007 |
| EP | 1 836 971 | 9/2007 |
| EP | 1562522 | 12/2008 |
| EP | 1357843 | 5/2009 |
| EP | 1 968 491 | 7/2010 |
| EP | 1928357 | 11/2010 |
| EP | 1718249 | 4/2011 |
| EP | 2399549 | 3/2014 |
| EP | 1646332 | 6/2015 |
| EP | 2410948 | 7/2016 |
| EP | 2465568 | 8/2016 |
| EP | 2023858 | 10/2016 |
| WO | 1992/005093 | 4/1992 |
| WO | 1997/041778 | 11/1997 |
| WO | 2000/28923 | 5/2000 |
| WO | 2001/010306 | 2/2001 |
| WO | 2004/069055 | 8/2004 |
| WO | 2004/082538 | 9/2004 |
| WO | 2005/021063 | 3/2005 |
| WO | 2005/058206 | 6/2005 |
| WO | 2005/102194 | 11/2005 |
| WO | 2006/019498 | 2/2006 |
| WO | 2006/097931 | 9/2006 |
| WO | 2006/105008 | 10/2006 |
| WO | 2006/105009 | 10/2006 |
| WO | 2007/080595 | 7/2007 |
| WO | 2007/140309 | 12/2007 |
| WO | 2008/065044 | 6/2008 |
| WO | 2008/068756 | 6/2008 |
| WO | 2009/039400 | 3/2009 |
| WO | 2009/101617 | 8/2009 |
| WO | 2010/004546 | 1/2010 |
| WO | 2010/008549 | 1/2010 |
| WO | 2010/071494 | 6/2010 |
| WO | 2010/073246 | 7/2010 |
| WO | 2010/099032 | 9/2010 |
| WO | 2010/108079 | 9/2010 |
| WO | 2010/128502 | 11/2010 |
| WO | 2010/128503 | 11/2010 |
| WO | 2011/014496 | 2/2011 |
| WO | 2011/037891 | 3/2011 |
| WO | 2011/051942 | 5/2011 |
| WO | 2011/089601 | 7/2011 |
| WO | 2011/097355 | 8/2011 |
| WO | 2011/143263 | 11/2011 |
| WO | 2011/153408 | 12/2011 |
| WO | 2012/127309 | 9/2012 |
| WO | 2013/003228 | 1/2013 |
| WO | 2013/011502 | 1/2013 |
| WO | 2013/028145 | 2/2013 |
| WO | 2013/078497 | 6/2013 |
| WO | 2014/043527 | 3/2014 |
| WO | 2014/064694 | 5/2014 |
| WO | 2014/087402 | 6/2014 |
| WO | 2014/108903 | 7/2014 |
| WO | 2014/141239 | 9/2014 |
| WO | 2015/015497 | 2/2015 |
| WO | 2015/063580 | 5/2015 |
| WO | 2015/193728 | 12/2015 |
| WO | 2016/011275 | 1/2016 |
| WO | 2016/087934 | 6/2016 |

OTHER PUBLICATIONS

An International Search Report 2013, which issued during and a Written Opinion both dated Dec. 6, 2013, which issued during the prosecution of Applicant's PCT/IL2013/050470.

(56) References Cited

OTHER PUBLICATIONS

U.S. Appl. No. 62/131,636, filed Mar. 11, 2015.
Alfieri et al., "An effective technique to correct anterior mitral leaflet prolapse," J Card Surg 14(6):468-470 (1999).
U.S. Appl. No. 62/014,397, filed Jun. 19, 2014.
Alfieri et al., "Novel suture device for beating heart mitral leaflet approximation," Annals of Thoracic Surgery 74:1488 1493 (2002).
Alfieri et al., "The double orifice technique in mitral valve repair: a simple solution for complex problems," Journal of Thoracic Cardiovascular Surgery 122:674-681 (2001).
Amplatzer Cardiac Plug Brochure (English Pages), AGA Medical Corporation, Plymouth, MN Copyright 2008-2011, downloaded Jan. 11, 2011.
Beale BS, "Surgical Repair of Collateral Ligament Injuries," presented at 63rd CVMA Convention, Halifax, Nova Scotia, Canada, Jul. 6-9, 2011.
Dentistry Today, "Implant Direct" product information page, Jun. 1, 2011, downloaded Dec. 10, 2012 from http://dentistrytoday.com/top25implant-i/5558-implant-direct.
Maisano et al., "The double-orifice technique as a standardized approach to treat mitral regurgitation due to severe myxomatous disease: surgical technique," European Journal of Cardio-thoracic Surgery 17 (2000) 201-205.
Shikhar Agarwal et al., "Interventional Cardiology Perspective of Functional Tricuspid Regurgitation," Circulatoin: Cardiovascular Interventions, pp. 565-573; Dec. 2009; vol. 2, Issue 6.
Smith & Nephew MINITAC™ TI 2.0 Suture Anchor Product Description, downloaded on Dec. 9, 2012 from http://global.smith-nephew.com/us/MINITAC_TI_2_SUTURE_ANCHR_3127.htm.
Second Notice of Allowance dated May 10, 2013, which issued during the prosecution of U.S. Appl. No. 12/692,061.
An Interview Summary dated Oct. 24, 2012, which issued during the prosecution of U.S. Appl. No. 12/692,061.
An Office Action dated Jul. 6, 2012, which issued during the prosecution of U.S. Appl. No. 12/692,061.
A Notice of Allowance dated Mar. 6, 2013, which issued during the prosecution of U.S. Appl. No. 12/692,061.
An International Search Report and a Written Opinion both dated May 19, 2011, which issued during the prosecution of Applicant's PCT/IL11/00064.
An International Search Report and a Written Opinion both dated Jan. 22, 2013, which issued during the prosecution of Applicant's PCT/IL2012/000282.
An Office Action dated Dec. 5, 2013, which issued during the prosecution of U.S. Appl. No. 13/485,145.
An International Search Report and a Written Opinion both dated Mar. 17, 2014, which issued during the prosecution of Applicant's PCT/IL2013/050937.
Invitation to pay additional fees in PCT/IL2014/050027 dated Apr. 4 2014.
An International Search Report which issued during the prosecution and a Written Opinion both dated May 28, 2014, which issued during the prosecution of Applicant's PCT/IL2014/050027.
U.S. Appl. No. 60/902,146, filed Feb. 16, 2007.
European Search Report dated Apr. 10, 2015, which issued during the prosecution of Applicant's European App No. 11734451.5.
European Search Report dated May 15, 2015, which issued during the prosecution of Applicant's European App No. 12814417.7.
An Office Action dated Sep. 14, 2015, which issued during the prosecution of U.S. Appl. No. 13/553,081.
An English Translation of an Office Action dated Jun. 30, 2015 which issued during the prosecution of Chinese Patent Application No. 201180015301.6.
An English Translation of an Office Action dated Jul. 7, 2015 which issued during the prosecution of Japanese Patent Application No. 2012-549463.
An Office Action dated Oct. 7, 2015, which issued during the prosecution of U.S. Appl. No. 13/574,088.
Invitation to Pay Additional Fees dated Apr. 20, 2015, which issued during the prosecution of Applicant's PCT/IB2014/002351.
An International Search Report and a Written Opinion both dated Jun. 10, 2015, which issued during the prosecution of Applicant's PCT/IB2014/002351.
An Office Action dated Feb. 2, 2015, which issued during the prosecution of U.S. Appl. No. 14/143,355.
An English Translation of an Office Action dated Feb. 10, 2015 which issued during the prosecution of Chinese Patent Application No. 201180015301.6.
An Office Action dated Feb. 25, 2015, which issued during the prosecution of U.S. Appl. No. 13/574,088.
Notice of Allowance dated Sep. 24, 2015, which issued during the prosecution of U.S. Appl. No. 14/143,355.
Notice of Allowance dated Dec. 4, 2015, which issued during the prosecution of U.S. Appl. No. 14/143,355.
An Office Action dated Jul. 7, 2014, which issued during the prosecution of U.S. Appl. No. 13/485,145.
An English Translation of an Office Action dated Jun. 30, 2014 which issued during the prosecution of Chinese Patent Application No. 201180015301.6.
An Office Action dated Sep. 25, 2014, which issued during the prosecution of U.S. Appl. No. 13/485,145.
An English Translation of an Office Action dated Oct. 28, 2014,which issued Japanese Patent Application No. 2012-549463.
Notice of Allowance dated Dec. 9, 2014, which issued during the prosecution U.S. Appl. No. 13/485,145.
An International Search Report and a Written Opinion both dated Jun. 30, 2014, which issued during the prosecution of Applicant's PCT/IL2014/050233.
An International Search Report and a Written Opinion both dated Jan. 8 2016, 2014, which issued during the prosecution of Applicant's PCT/IB2015/001196.
Invitation to pay additional fees in PCT/IB2015/001196 dated Oct. 26, 2015.
Notice of Allowance dated Dec. 4, 2014, which issued during the prosecution of U.S. Appl. No. 13/ 188,175.
An Office Action dated Nov. 25, 2014, which issued during the prosecution of U.S. Appl. No. 13/553,081.
An Office Action dated Apr. 18, 2016, which issued during the prosecution of U.S. Appl. No. 14/584,286.
Spinal & Epidural Needles—downloaded on Feb. 18, 2016 from http://www.cothon.net/Anestesia_Obstetrica/Neuroaxial_needles.html.
An Office Action dated May 11, 2016, which issued during the prosecution of U.S. Appl. No. 13/574,088.
An International Search Report and a Written Opinion both dated Apr. 15, 2016, 2014, which issued during the prosecution of Applicant's PCT/IB2015/002354.
U.S. Appl. No. 62/167,660, filed May 28, 2015.
An English Translation of an Office Action dated Jun. 23, 2016 which issued during the prosecution of Chinese Patent Application No. 201480028044.3. (the relevant part only).
U.S. Appl. No. 62/086,269, filed Dec. 2, 2014.
Notice of Allowance dated Sep. 5, 2016, which issued during the prosecution of Chinese Patent Application No. 2014800280443.
An Office Action dated Sep. 14, 2016, which issued during the prosecution of U.S. Appl. No. 13/574,088.
Invitation to pay additional fees in PCT/IB2016/000840 dated Oct. 13, 2016.

* cited by examiner

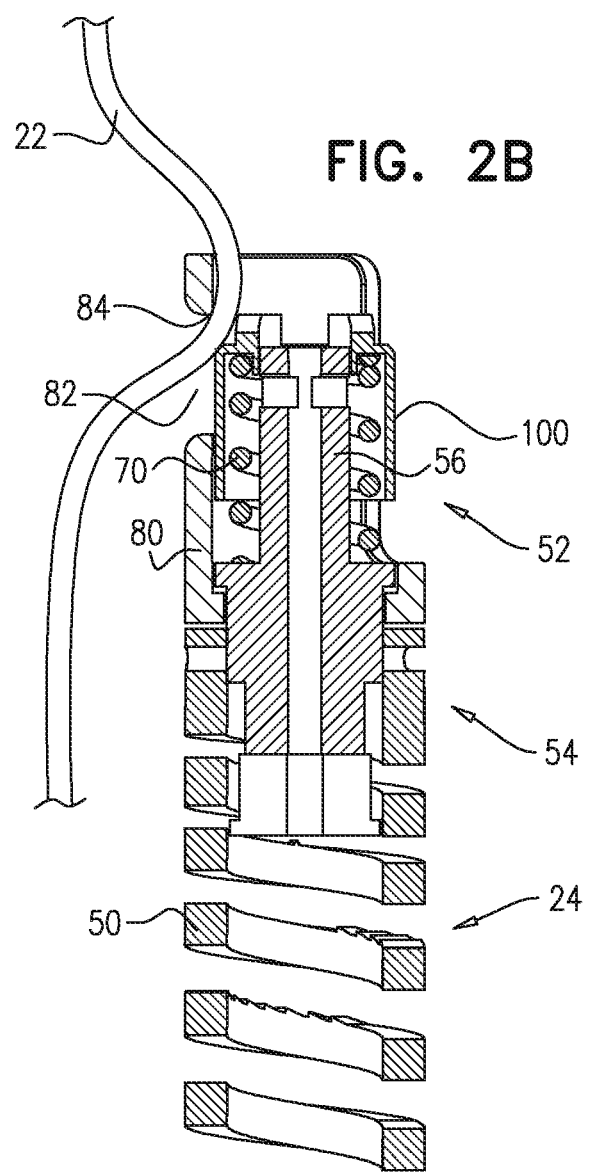

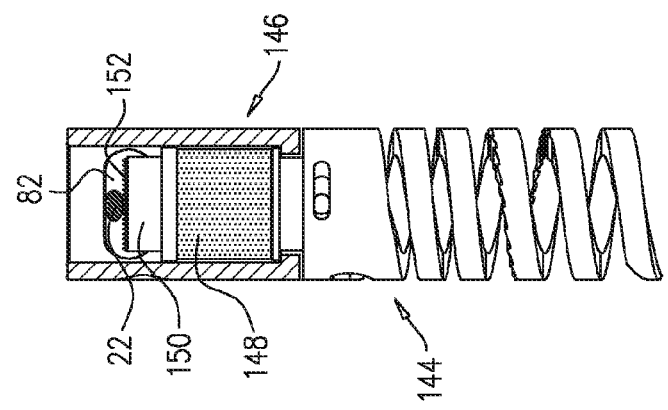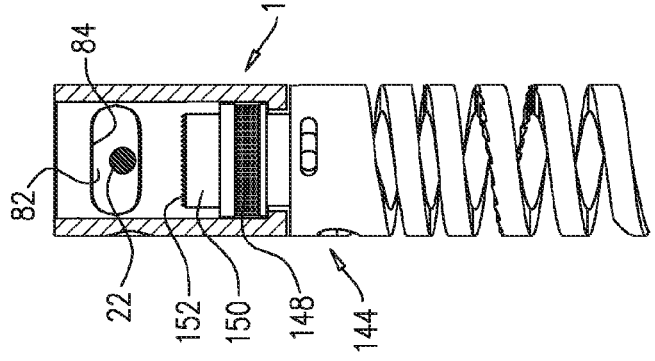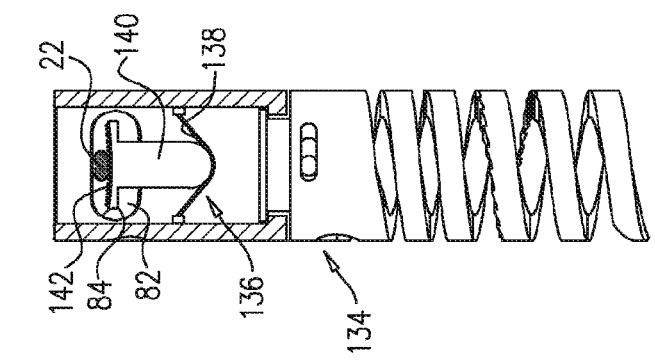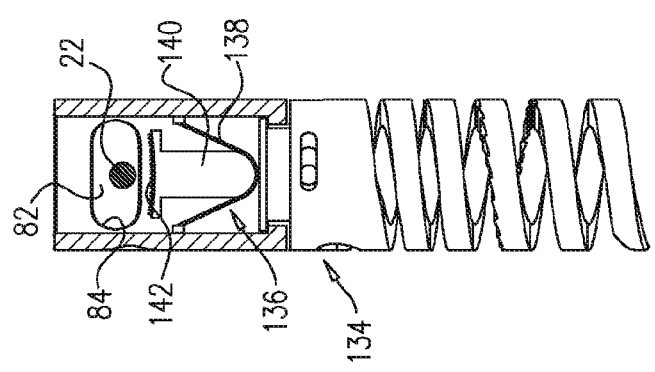

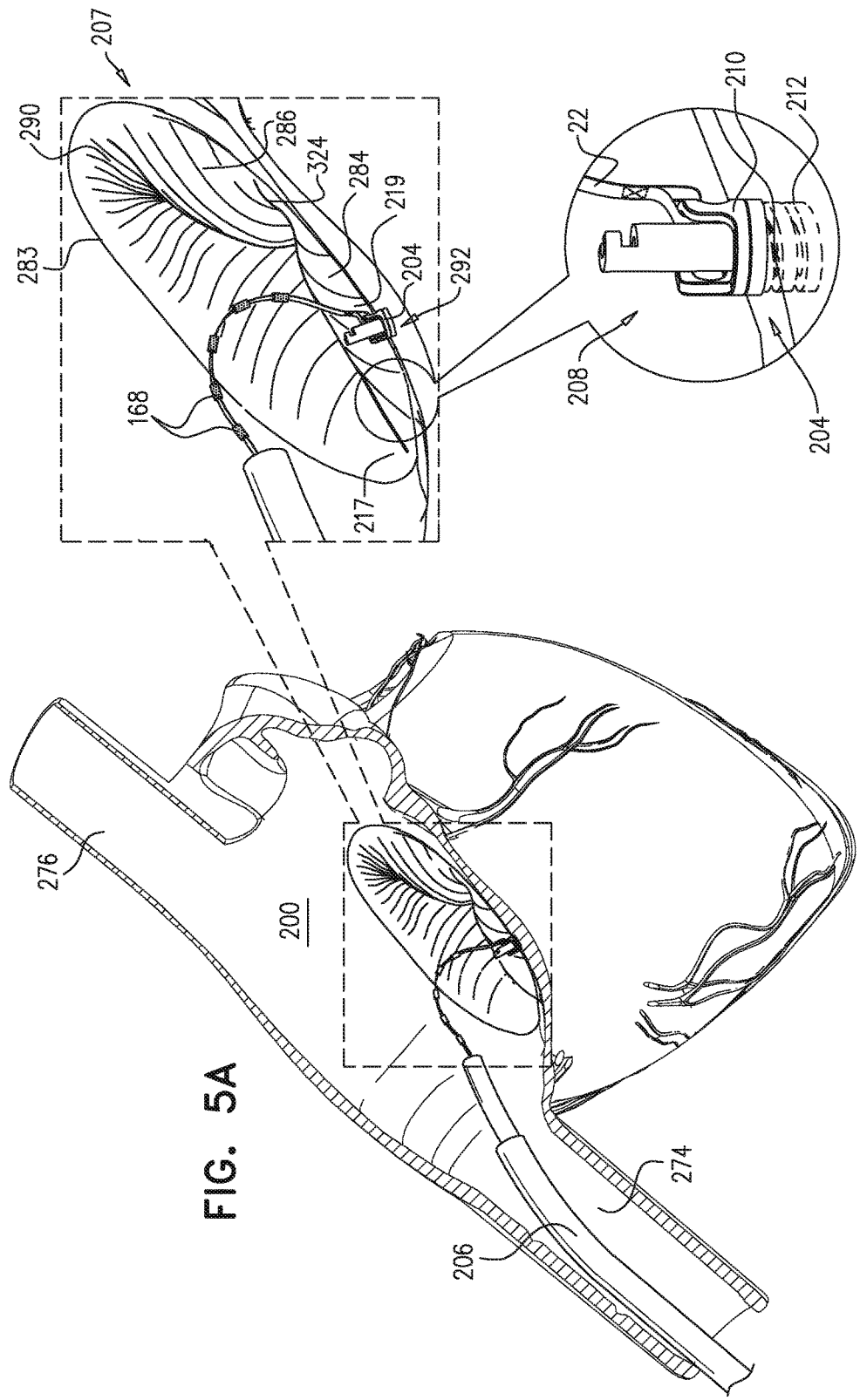

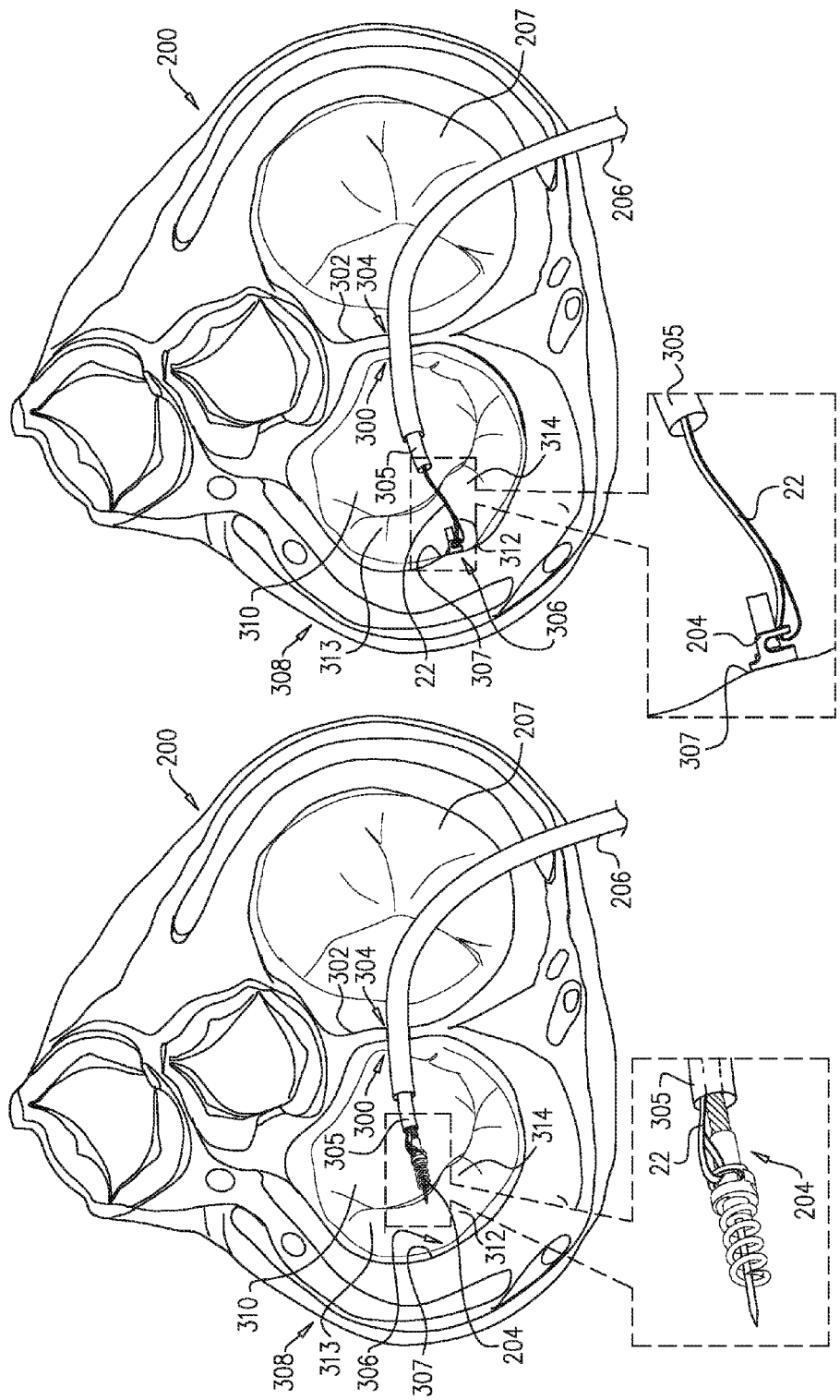

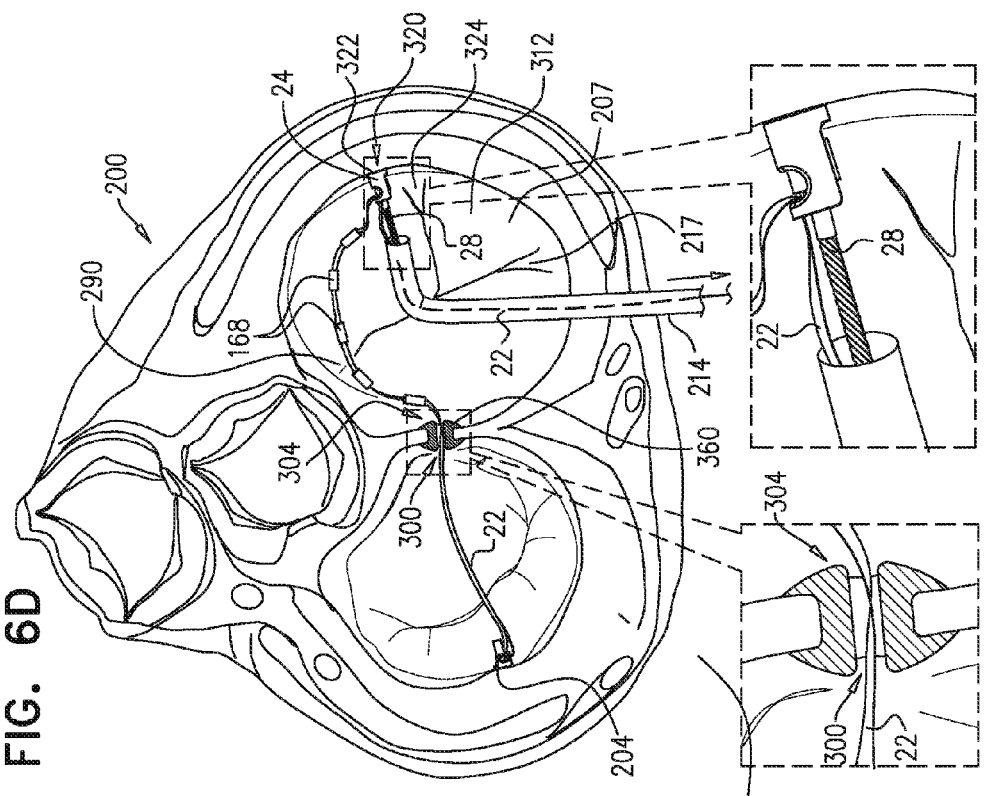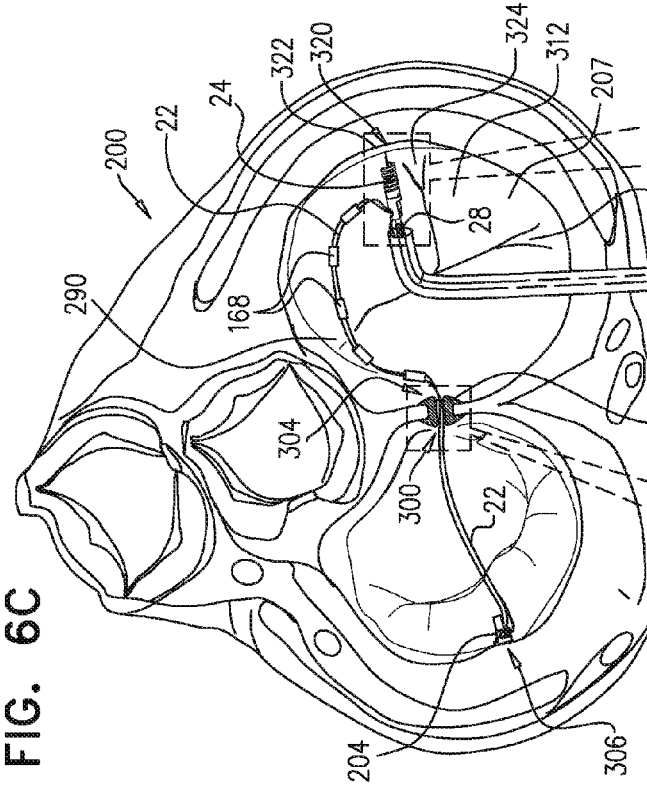
FIG. 6C
FIG. 6D

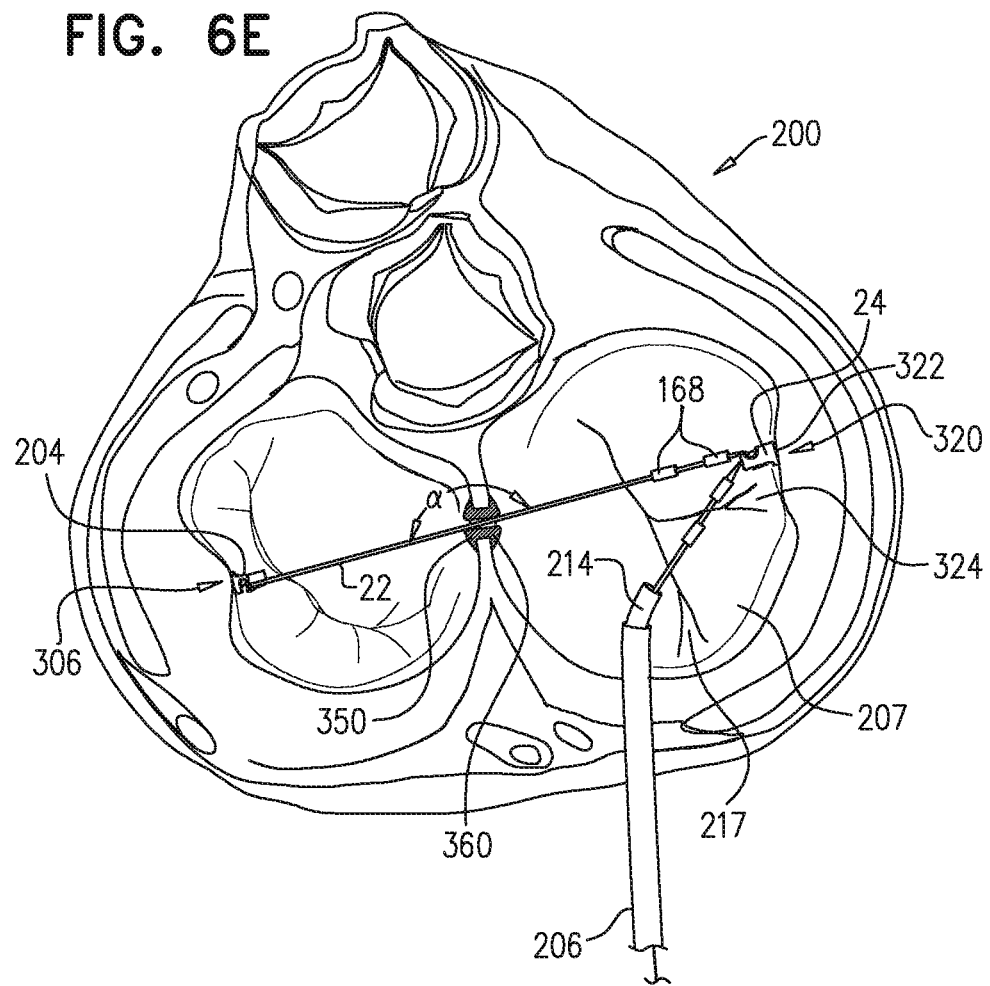

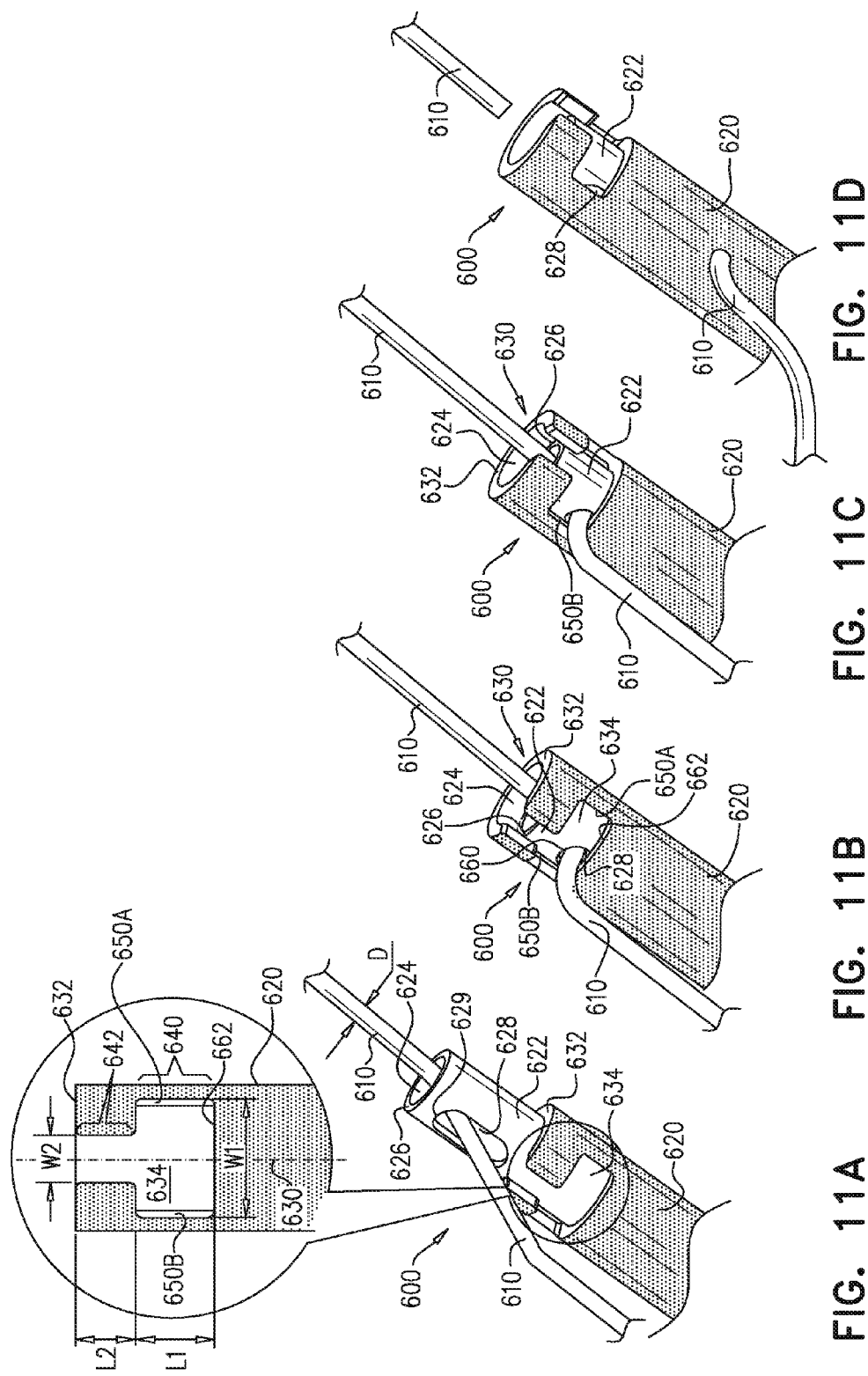

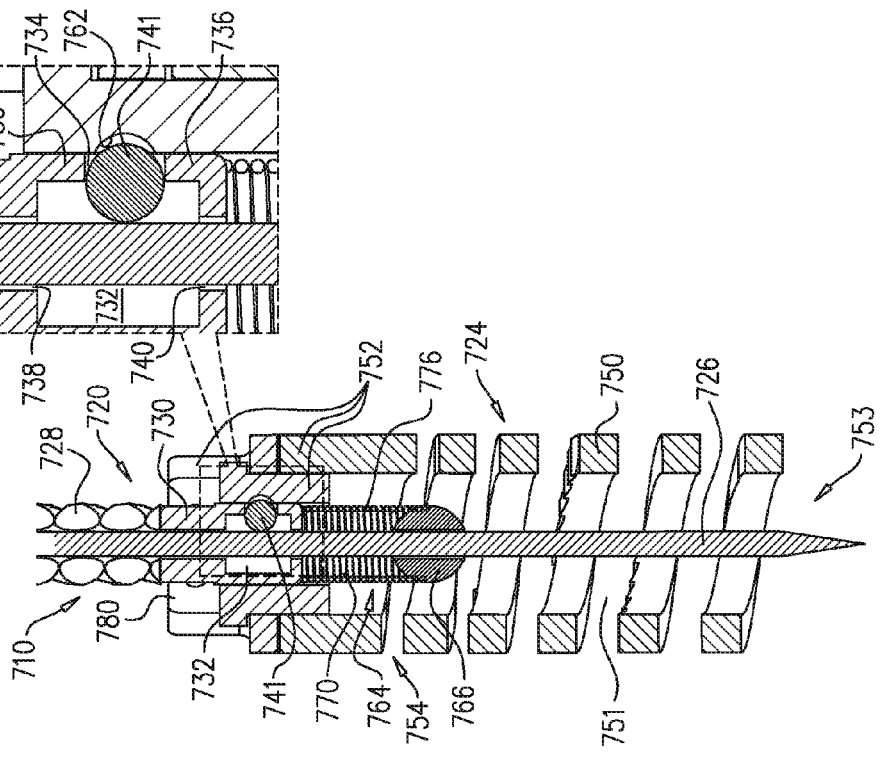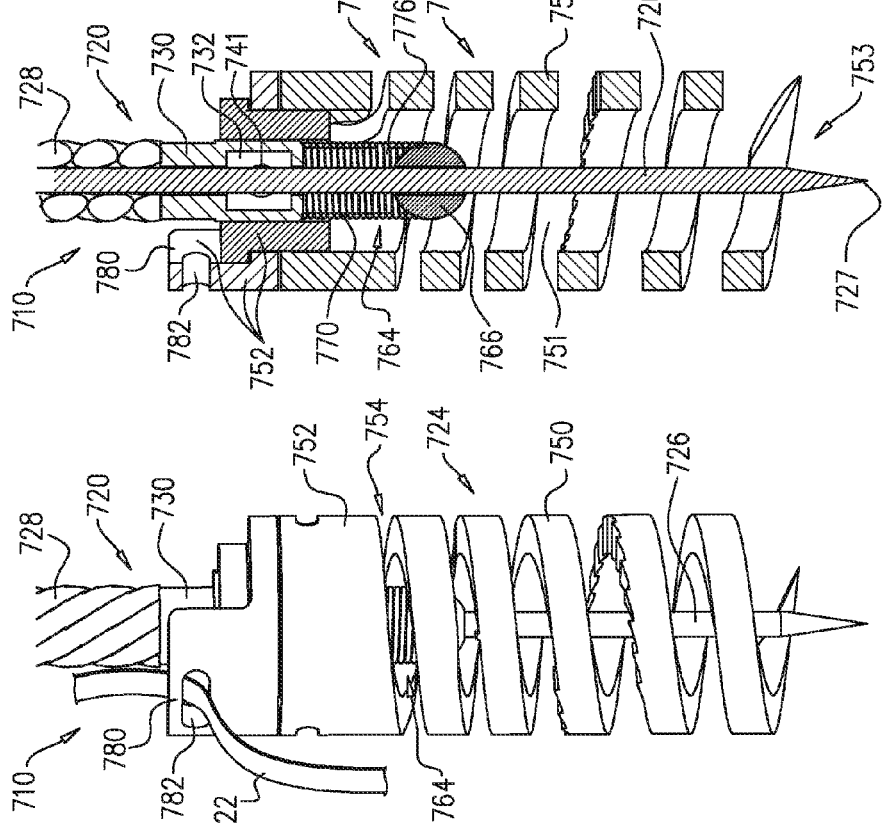

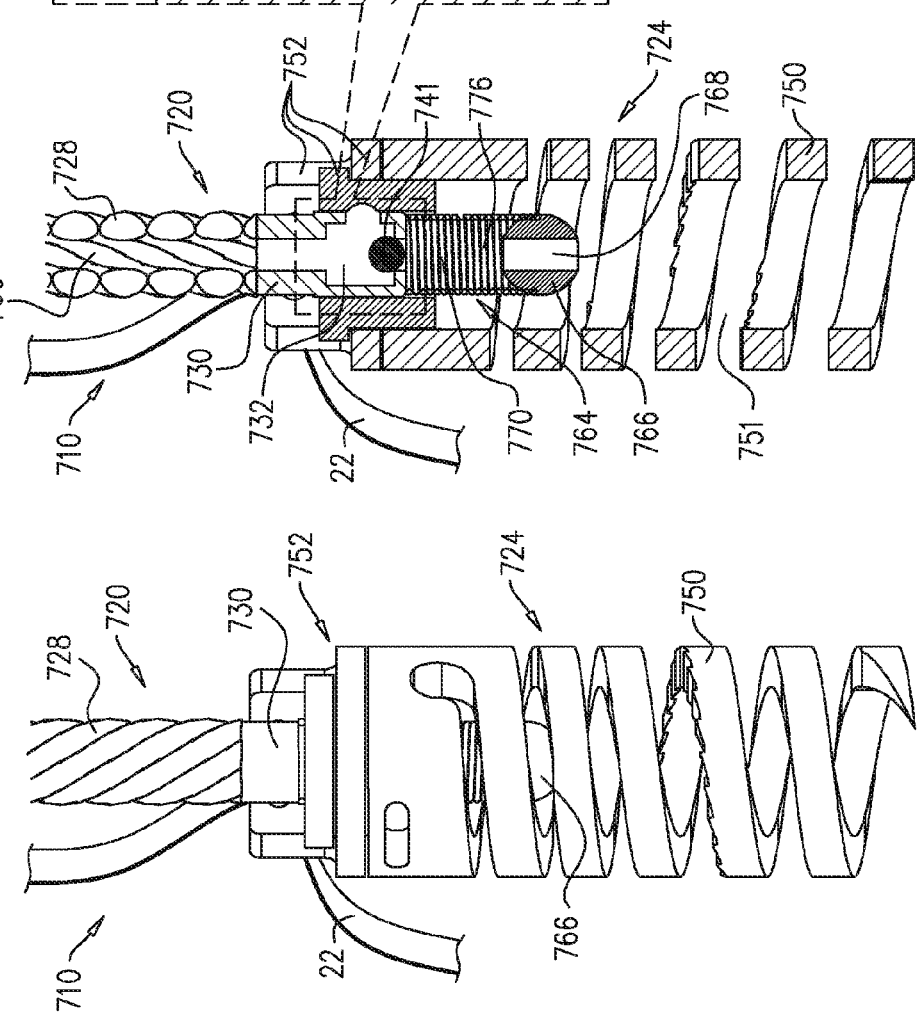

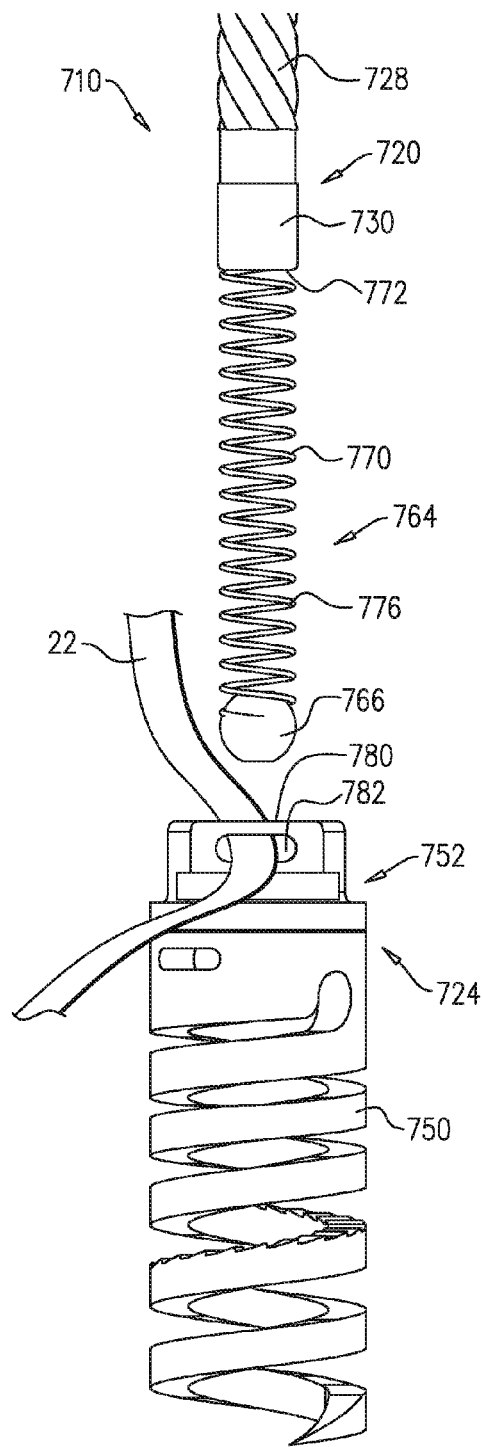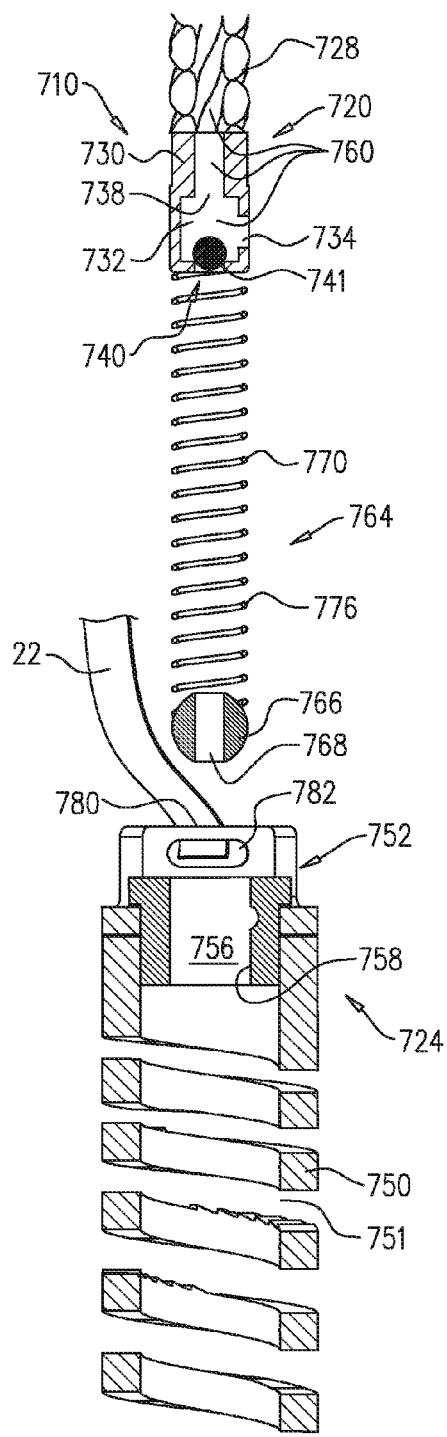

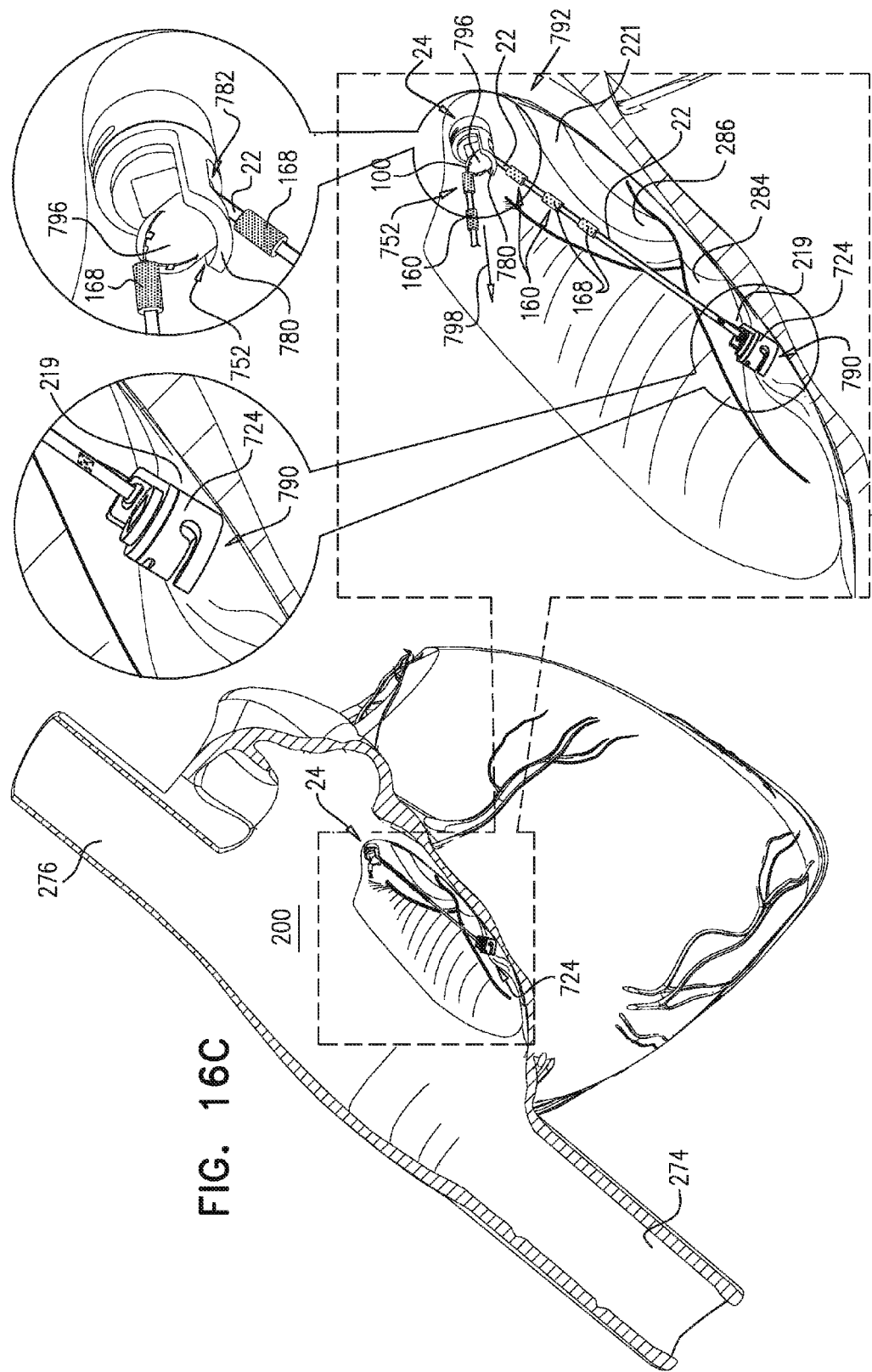

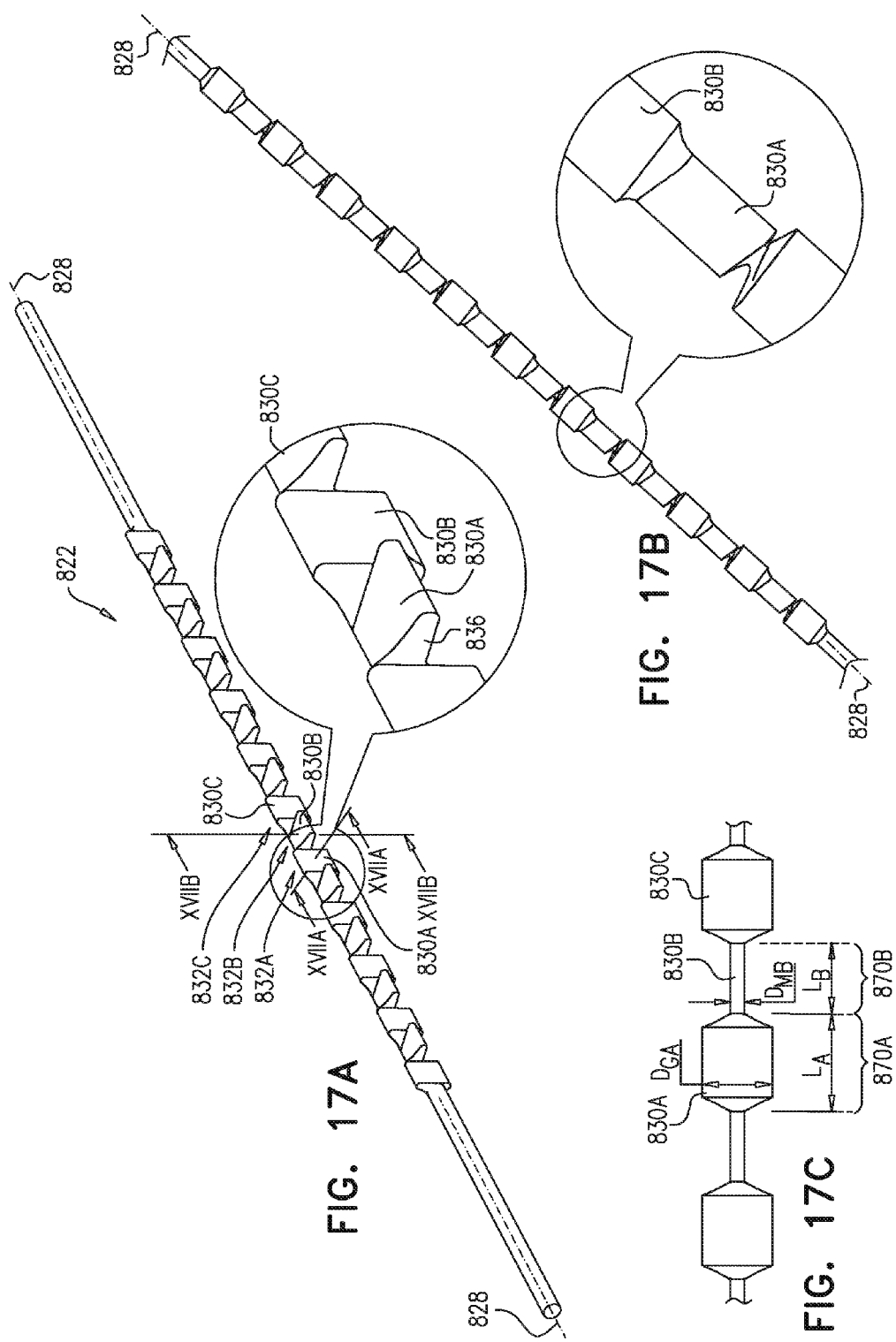

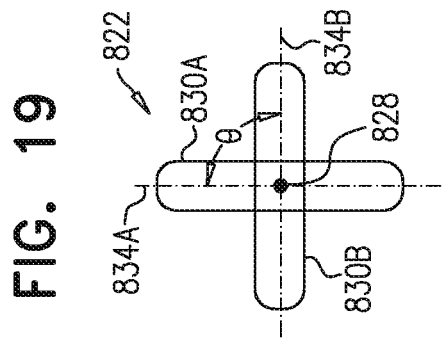
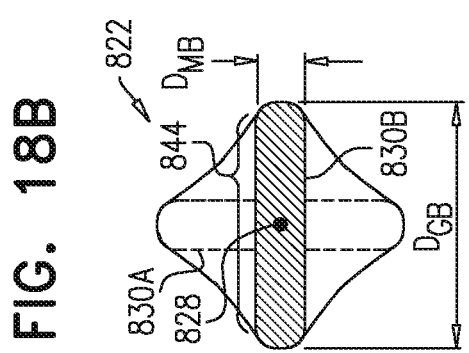
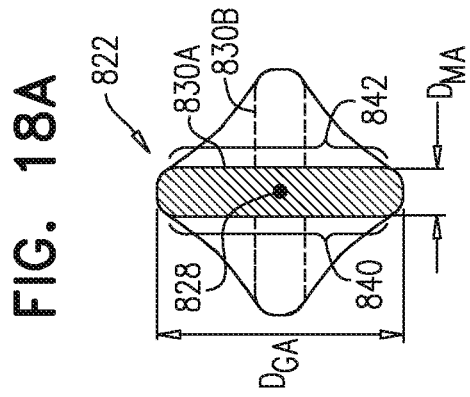

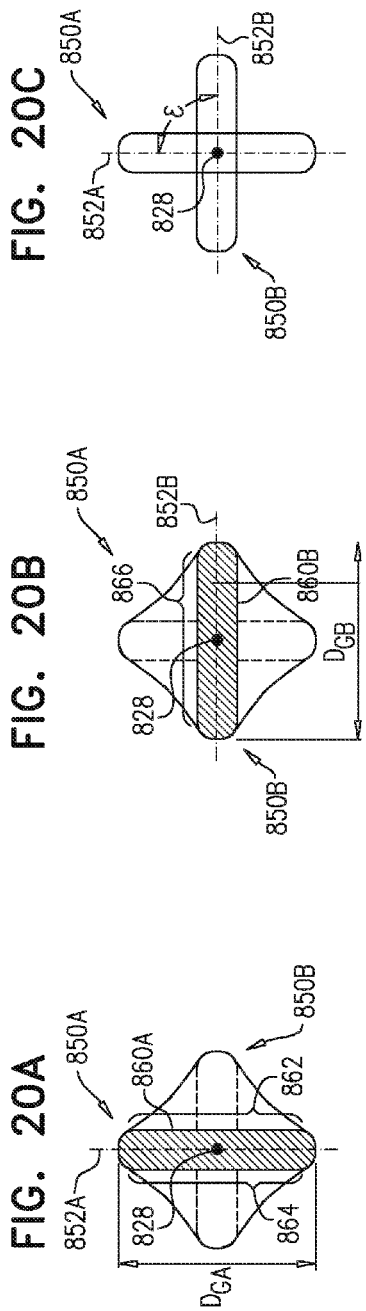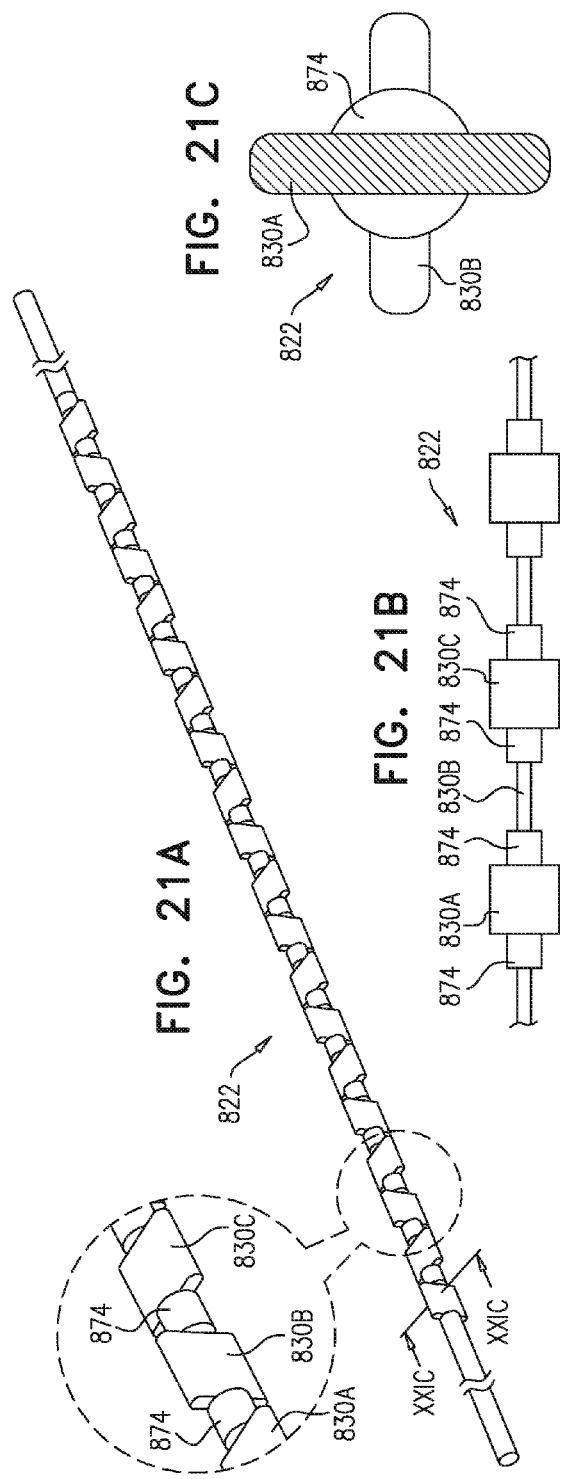

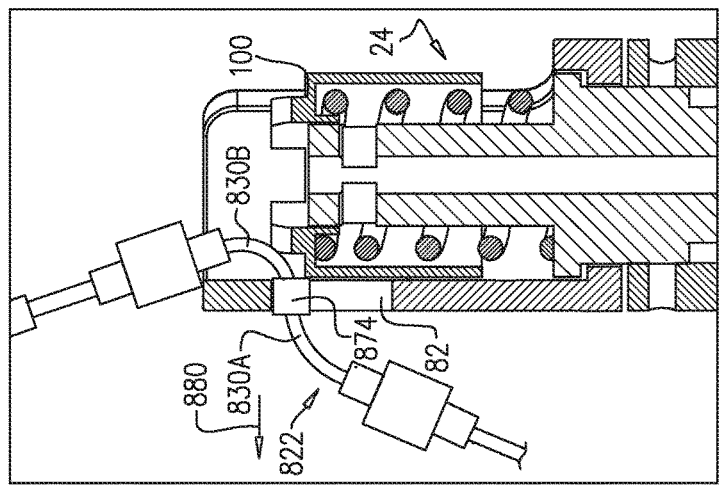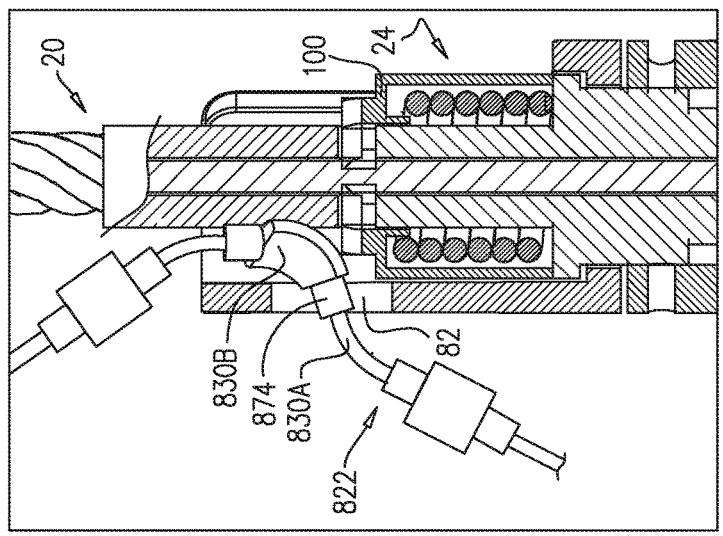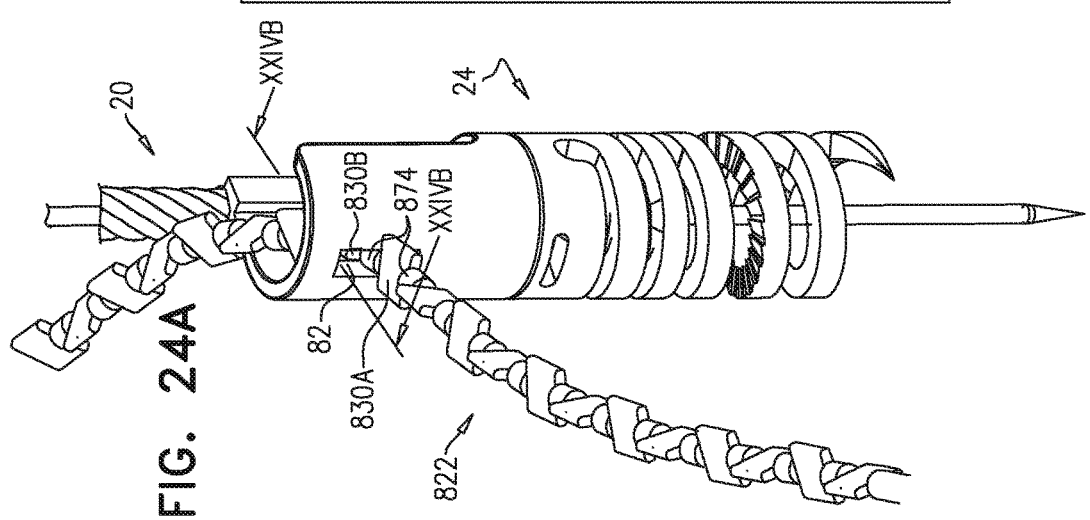

CARDIAC TISSUE CINCHING

CROSS-REFERENCE TO RELATED APPLICATIONS

The present application is the US national stage of International Application PCT/IB2015/001196, filed Jun. 14, 2015, which claims priority from (a) U.S. Provisional Application 62/014,397, filed Jun. 19, 2014, and (b) U.S. Provisional Application 62/131,636, filed Mar. 11, 2015, both of which are assigned to the assignee of the present application and are incorporated herein by reference.

FIELD OF THE APPLICATION

Some applications of the present invention relate in general to valve repair. More specifically, some applications of the present invention relate to repair of an atrioventricular valve of a patient.

BACKGROUND OF THE APPLICATION

Functional tricuspid regurgitation (FTR) is governed by several pathophysiologic abnormalities such as tricuspid valve annular dilatation, annular shape abnormality, pulmonary hypertension, left or right ventricle dysfunction, right ventricle geometry, and leaflet tethering. Treatment options for FTR are primarily surgical. The current prevalence of moderate-to-severe tricuspid regurgitation is estimated to be 1.6 million in the United States. Of these, only 8,000 patients undergo tricuspid valve surgeries annually, most of them in conjunction with left heart valve surgeries.

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

It has been reported that at least 30% of patients that suffer from mitral valve regurgitation have concurrent regurgitation of the tricuspid valve. See, for example, Di Mauro et al., "Mitral Valve surgery for functional mitral regurgitation: prognostic role of tricuspid regurgitation," European Journal of Cardio-thoratic Surgery (2009) 635-640, and King R M et al., "Surgery for tricuspid regurgitation late after mitral valve replacement," Circulation 1984; 70: I193-7.

SUMMARY OF THE APPLICATION

In some applications of the present invention, techniques are provided for tightening tethers of percutaneous implants transluminally, in order to enable percutaneous treatment of functional tricuspid and/or mitral regurgitation (FTR and/or FMR).

In some applications of the present invention, a tissue-anchor system comprises a torque-delivery tool, a tether, and a tissue anchor. The torque-delivery tool is configured to implant the tissue anchor in cardiac tissue, and thereafter to lock the tether to the tissue anchor, such that sliding of the tether with respect to the tissue anchor is inhibited. Typically, the tether is tensioned after the tissue anchor has been implanted in the cardiac tissue, and after the tether has been tensioned, the tether is locked to the tissue anchor.

The torque-delivery tool comprises (a) a torque-delivery cable, which comprises a distal torque-delivery head (b) a distal coupling element that is fixed to a distal end of the distal torque-delivery head, and (c) a distal spring depressor. The tissue anchor comprises (a) a tissue-coupling element, and (b) a proximal anchor head, which is attached to a proximal portion of the tissue-coupling element. The anchor head comprises an axially-stationary shaft and a tether-locking mechanism. The axially-stationary shaft has (a) a distal portion that is axially fixed with respect to the proximal portion of the tissue-coupling element, and (I)) a proximal end that comprises a proximal coupling element. The distal and proximal coupling elements are shaped so as to define corresponding interlocking surfaces, which facilitate coupling of the distal torque-delivery head to the axially-stationary shaft.

The tether-locking mechanism comprises a spring and an outer tether-securing element. The outer tether-securing element (i) is shaped so as to define a lateral opening through which the tether is disposed, and (ii) at least partially radially surrounds the axially-stationary shaft and the spring (and hammer cap, if provided, as described below). For some applications, at least a portion of the spring radially surrounds the axially-stationary shaft.

The tissue-anchor system is configured to assume:
an unlocked state, in which (a) the distal and proximal coupling elements are interlockedly coupled with one other, and (b) the distal spring depressor restrains the spring in an axially-compressed state, in which state the spring does not inhibit sliding of the tether through the lateral opening, and
a locked state, in which (b) the distal and proximal coupling elements are not coupled with one another, (b) the distal spring depressor does not restrain the spring in the axially-compressed state, and (c) the spring is in an axially-expanded state, in which state the spring inhibits the sliding of the tether through the lateral opening by pressing the tether against the outer tether-securing element, such as against a perimeter of the lateral opening.

When the tissue-anchor system is in the unlocked state, the tether-locking mechanism is also in an unlocked state, in which state the spring does not inhibit sliding of the tether through the lateral opening. When the tissue-anchor system is in the locked state, the tether-locking mechanism is also in a locked state, in which state the spring inhibits the sliding of the tether through the lateral opening by pressing the tether against the outer tether-securing element, such as against the perimeter of the lateral opening.

The tissue-anchor system is advanced into a chamber of the heart in the unlocked state. The tissue anchor is implanted in cardiac tissue, using the torque-delivery cable while the tissue-anchor system is in the unlocked state. After the tissue anchor is implanted, tension is applied to the tether. As tension is applied, the tether advances through the lateral opening of the outer tether-securing element of the anchor head. The application of tension occurs in the heart chamber, in which there is space to maneuver, and the physician has tactile and visual control. Thereafter, the distal torque-delivery head and cable is decoupled from the axially-stationary shaft of the tissue anchor, thereby allowing the spring to expand and press the tether against the outer tether-securing element. This pressing locks the tether with respect to the tissue anchor, and maintains the distance and tension between the tissue anchor and one or more other implanted tissue anchors.

The torque-delivery cable thus serves two functions:

implanting the tissue anchor in cardiac tissue, by applying a rotational force to the tissue anchor; and maintaining the tissue-anchor system in the unlocked state, in which state the tether can slide with respect to the tissue anchor, allowing tension to be applied to the tether (and adjusted as necessary).

Similarly, decoupling of the torque-delivery cable from the axially-stationary shaft of the anchor head of the tissue anchor simultaneously (1) releases the tissue anchor and (2) transitions tissue-anchor system to the locked state.

For some applications, the anchor head further comprises a hammer cap, which is fixed to the spring, and covers at least a portion of the spring, including a proximal end of the spring. When the tissue-anchor system is in the locked state, the spring presses the tether against the outer tether-securing element by pressing the hammer cap against the outer tether-securing element, such as the perimeter of the lateral opening. The hammer cap may prevent entanglement of the tether with the spring.

For some applications, the tissue-anchor system further comprises a locking wire. The torque-delivery cable (including the distal torque-delivery head), the distal coupling element, the proximal coupling element, and the axially-stationary shaft are shaped so as define respective channels therethrough, which are radially aligned with each other and coaxial with the tissue anchor. When the tissue-anchor system is in the unlocked state, a portion of the locking wire is disposed in the channels, thereby preventing decoupling of the distal and proximal coupling elements from one another. Proximal withdrawal and removal of the portion of the locking wire from the channels allows the decoupling of the distal and proximal coupling elements from one another.

For some applications, the tissue-anchor system is used in a procedure for repairing a tricuspid valve, or a mitral valve. The procedure is performed using a valve-tensioning implant system, which comprises the tissue-anchor system, including the torque-delivery tool, the tether, and the tissue anchor. In this procedure, the tissue anchor serves as a second tissue anchor. The valve-tensioning implant system further comprises a first tissue anchor, which typically comprises a helical tissue-coupling element, which punctures and screws into cardiac muscle tissue. The valve-tensioning implant system allows the first and second tissue anchors to be delivered separately and connected afterwards in situ. This simplifies the procedure for the operator, and allows an approach from two or more different blood vessels such as transfemoral, transjugular, transradial or transapical approaches, which may provide simpler access to the anchoring point.

In some applications of the present invention, a tissue-anchor system comprises a tissue anchor, a locking shaft having a sharp distal tip, a torque-delivery tool, and, optionally, a tether, which is coupled to the anchor head. The tissue anchor which comprises (a) a helical tissue-coupling element, which is shaped so as to define and surrounds a helical tissue-coupling element channel that extends to a distal end of the helical tissue-coupling element, and (b) an anchor head. The anchor head (i) is attached to a proximal portion of the helical tissue-coupling element, and (ii) is shaped so as to define a head-coupling channel, which has an internal wall. The torque-delivery tool is configured to implant the tissue anchor in cardiac tissue, and comprises a torque-delivery cable, a distal torque-delivery head, and a coupling element (which may be spherical). The distal torque-delivery head is fixed to the torque-delivery cable, and is shaped so as to define a chamber, which is shaped so as to define a fenestration through a lateral wall of the chamber, and proximal and distal chamber end openings. The coupling element is (i) not fixed to any elements of the tissue-anchor system, (ii) too large to pass through the fenestration, and (iii) too large to pass through the distal chamber end opening.

The torque-delivery cable and the distal torque-delivery head together are shaped so as to define a locking shaft-accepting channel, which (a) passes through (i) the torque-delivery cable, (ii) the chamber, and (iii) the proximal and the distal chamber end openings, and (b) is coaxial with the helical tissue-coupling element channel. The tissue-anchor system is configured to assume engaged and disengaged states, in which the distal torque-delivery head is engaged and not engaged to the anchor head, respectively.

The tissue-anchor system is in the engaged state when the locking shaft is removably disposed in the locking-wire-accepting channel and at least partially within the helical tissue-coupling element channel, with the locking shaft constraining the coupling element to partially protrude through the fenestration out of the chamber and against the internal wall of the head-coupling channel, thereby axially locking the distal torque-delivery head with respect to the head-coupling channel. The tissue-anchor system is in the disengaged state when the locking shaft is not disposed in the locking-wire-accepting channel and is not disposed in the helical tissue-coupling element channel, and does not constrain the coupling element.

For some applications, the internal wall of the head-coupling channel is shaped so as to define a coupling indentation, and the tissue-anchor system is in the engaged state when the locking shaft is removably disposed in the locking-wire-accepting channel and at least partially within the helical tissue-coupling element channel, with the locking shaft constraining the coupling element to partially protrude through the fenestration out of the chamber and into the coupling indentation of the internal wall of the head-coupling channel.

For some applications, the torque-delivery tool further comprises a depth-finding tool, which comprises a radiopaque bead shaped so as to define a hole therethrough. The bead is removably positioned within the helical tissue-coupling element channel. The locking shaft passes through the hole of the bead, such that the bead is slidable along the locking shaft and along the helical tissue-coupling element channel, when the locking shaft is removably disposed at least partially within the helical tissue-coupling element channel when the tissue-anchor system is in the engaged state.

In some applications of the present invention, a flexible tether is provided. The tether may be used, for example, to apply tension between two or more tissue anchors, such as tissue anchors described herein. When the tether is tensioned into a straight configuration, (a) the tether has a central longitudinal axis, and is shaped so as to define first and second blades, which are disposed (i) at first and second longitudinal locations, and (ii) within 10 mm of one another along the central longitudinal axis, and (b) the first and the second blades have respective best-fit planes, which intersect at an angle of at least 30 degrees, such as at least 60 degrees. For some applications, the central longitudinal axis falls in the first and the second best-fit planes, or is parallel to the first and the second best-fit planes.

In some applications of the present invention, a tricuspid-mitral valve repair procedure is provided. In this procedure, both the tricuspid and the mitral valves are repaired by simultaneously applying tension across both valves using a tether that passes through the atrial septum. This transcatheter repair procedure cinches both valves with a single valve-tensioning implant system. This offers a simple and cost-effective treatment for patients who otherwise would require multiple procedures or would be left at least partially untreated. For some applications, the valve-tensioning implant system comprises the tissue-anchor system described above, including the torque-delivery tool, the tether, and the tissue anchor. In this procedure, the tissue anchor described above serves as a second tissue anchor. The valve-tensioning implant system further comprises a first tissue anchor. Alternatively, other tissue-anchoring and/or tether tensioning techniques may be used.

In this tricuspid-mitral valve repair procedure, the valve-tensioning implant system is typically introduced transcatheterly and endovascularly (typically percutaneously), via a catheter, with the aid of a guidewire, through vasculature of the subject. The catheter is introduced into a right atrium, and an opening is made through an atrial septum at a septal site, which is typically at least 5 mm from the fossa ovalis, such as at least 10 mm from the fossa ovalis.

The first tissue anchor is endovascularly advanced to a left-atrial site of a left atrium, the site selected from the group of sites consisting of: a mitral annular site on an annulus of a mitral valve, and a wall of the left atrium above the mitral annular site. Typically, in order to advance the first tissue anchor into the left atrium, the catheter is advanced through the opening. An inner tube may be advanced through the catheter, and a delivery tool may be advanced through the inner tube.

The first tissue anchor is implanted at the left-atrial site. For some applications, the mitral annular site circumferentially corresponds to a posterior leaflet of the mitral valve. For example, the mitral annular site may circumferentially correspond to an annular site of the mitral valve within 1 cm of a lateral scallop (P1) and/or within 1 cm of a middle scallop (P2) of the posterior leaflet. The inner tube, if used, is removed from the catheter, and the catheter is withdrawn to the right atrium. Outside of the subject's body, the physician then threads the free end of the tether through the lateral opening of outer tether-securing element of second the tissue anchor, and through a lumen of a delivery tube of the tissue-anchor system. The tether thus connects the first and second tissue anchors.

The tissue-anchor system, including the second tissue anchor and the torque-delivery cable, is endovascularly introduced over the tether and through the delivery tube, which itself is advanced through the catheter. The tissue-anchor system is introduced in the unlocked state (the tether-locking mechanism is also in the unlocked state). The distal end of the delivery tube, and the second tissue anchor, are steered to a right-atrial site of the right atrium selected from the group of sites consisting of: a tricuspid annular site on an annulus of the tricuspid valve, and a wall of the right atrium above the tricuspid annular site. For some applications, the tricuspid annular site circumferentially corresponds to an annular site of the tricuspid valve between (a) 2 cm anterior to an anteroposterior commissure (APC) of the tricuspid valve and (b) a posteroseptal commissure of the tricuspid valve. The second tissue anchor is implanted at the tricuspid annular site by rotating the torque-delivery cable.

The size of the tricuspid valve orifice and the size of the mitral valve orifice are reduced by approximating the left-atrial site and the right-atrial site by tensioning the tether, so as to reduce regurgitation. Such tensioning may be performed by proximally pulling on the free end of the tether, such that a portion of the tether is pulled through the lateral opening of the outer tether-securing element of the second tissue anchor.

Once the tension has been applied, the torque-delivery cable (including the distal torque-delivery head) is decoupled from the axially-stationary shaft of the second tissue anchor, such as by removing the locking shaft. As a result, the spring expands and presses the tether against the outer tether-securing element. This pressing transitions the tissue anchor system to the locked state (and the tether-locking mechanism to the locked state), by locking the tether with respect to the tissue anchor. Such locking maintains the distance and tension between the second tissue anchor and the first tissue anchor.

For some applications, the procedure further comprises placing, in the opening of the atrial septum, an annular reinforcement element that is shaped so as to define an opening therethrough. The reinforcement element is typically delivered and placed after implanting the first tissue anchor; and before implanting the second tissue anchor. The tether passes through the opening of the reinforcement element. The reinforcement element distributes the force of the tether against the opening of the atrial septum, which may prevent damage to the atrial septum, such as caused by cutting by the tether.

There is therefore provided, in accordance with an application of the present invention, a method including:
making an opening through an atrial septum at a septal site at least 5 mm from a fossa ovalis;
endovascularly advancing a first tissue anchor to a left-atrial site selected from the group of sites consisting of: a mitral annular site on an annulus of a mitral valve, and a wall of a left atrium of a heart above the mitral annular site;
implanting the first tissue anchor at the left-atrial site;
endovascularly advancing a second tissue anchor to a right-atrial site selected from the group of sites consisting of: a tricuspid annular site on an annulus of a tricuspid valve, and a wall of a right atrium of the heart above the tricuspid annular site;
implanting the second tissue anchor at the right-atrial site; and
approximating the left-atrial site and the right-atrial site by tensioning a tether that passes through the opening of the atrial septum and connects the first and the second tissue anchors.

For some applications, endovascularly advancing the first and the second tissue anchors includes percutaneously advancing the first and the second tissue anchors to the left- and right-atrial sites, respectively.

For some applications, the mitral annular site circumferentially corresponds to a posterior leaflet of the mitral valve.

For some applications, the mitral annular site circumferentially corresponds to an annular site of the mitral valve, which is characterized by at least one of the following: the annular site is within 1 cm of a lateral scallop (P1) of the posterior leaflet, and the annular site is within 1 cm of a middle scallop (P2) of the posterior leaflet.

For some applications, the tricuspid annular site circumferentially corresponds to an annular site of the tricuspid valve that is (a) at or clockwise to a point on the tricuspid annulus 2 cm counterclockwise to an anteroposterior commissure (APC) of the tricuspid valve, and (b) at or counterclockwise to a posteroseptal commissure of the tricuspid valve, as viewed from the right atrium.

For some applications:

the mitral annular site circumferentially corresponds to a posterior leaflet of the mitral valve, and the tricuspid annular site circumferentially corresponds to an annular site of the tricuspid valve that is (a) at or clockwise to a point on the tricuspid annulus 2 cm counterclockwise to an anteroposterior commissure (APC) of the tricuspid valve, and (b) at or counterclockwise to a posteroseptal commissure of the tricuspid valve, as viewed from the right atrium.

For some applications, the septal site is at least 10 mm from the fossa ovalis. For some applications, the septal site is anterior to the fossa ovalis. For some applications, the septal site is apical to the fossa ovalis. For some applications, the septal site is between 3 and 20 mm superior and anterior to a coronary sinus orifice and between 3 and 10 mm posterior to an aorta.

For some applications, implanting the first and the second tissue anchors and tensioning the tether includes implanting the first and the second tissue anchors and tensioning the tether such that an angle formed in the tether at the opening of the atrial septum is at least 120 degrees, such as at least 135 degrees. For some applications, the angle is less than 180 degrees.

For some applications, if the tensioned tether were to be projected onto a coronal plane of the heart, the angle as projected would be at least 120 degrees, such as at least 135 degrees. For some applications, the angle as projected would be less than 180 degrees.

For some applications, if the tensioned tether were to be projected onto a transverse plane of the heart, the angle as projected would be at least 120 degrees, such as at least 135 degrees. For some applications, the angle as projected would be less than 180 degrees.

For some applications, implanting the first and the second tissue anchors and tensioning the tether includes implanting the first and the second tissue anchors and tensioning the tether such that (a) a portion of the tensioned tether in the left atrium between the opening of the atrial septum and the first tissue anchor and (b) a plane defined by the annulus of the mitral valve, form an angle of less than 30 degrees.

For some applications, implanting the first and the second tissue anchors and tensioning the tether includes implanting the first and the second tissue anchors and tensioning the tether such that (a) a portion of the tensioned tether in the right atrium between the opening of the atrial septum and the second tissue anchor and (b) a plane defined by the annulus of the tricuspid valve, form an angle of less than 30 degrees.

For some applications, the method further includes placing, in the opening of the atrial septum, an annular reinforcement element that is shaped so as to define an opening therethrough, and the tether passes through the opening of the reinforcement element.

For some applications, endovascularly advancing the second tissue anchor includes endovascularly advancing the second tissue anchor after implanting the first tissue anchor. For some applications, endovascularly advancing the first tissue anchor includes endovascularly advancing the first tissue anchor after implanting the second tissue anchor.

There is further provided, in accordance with an application of the present invention, apparatus including a tissue-anchor system, which includes:

a torque-delivery tool, which includes (a) a torque-delivery cable, which includes a distal torque-delivery head, (b) a distal coupling element that is fixed to a distal end of the distal torque-delivery head, and (c) a distal spring depressor;

a tether; and a tissue anchor, which includes (a) a tissue-coupling element, and (b) an anchor head, which (i) is attached to a proximal portion of the tissue-coupling element, and (ii) includes:

an axially-stationary shaft, which (a) has a distal portion that is axially fixed with respect to the proximal portion of the tissue-coupling element, and (b) has a proximal end that includes a proximal coupling element, wherein the distal and the proximal coupling elements are shaped so as to define corresponding interlocking surfaces;

a spring; and an outer tether-securing element, which (a) is shaped so as to define a lateral opening through which the tether is disposed, and (h) at least partially radially surrounds the axially-stationary shaft and the spring, wherein the tissue-anchor system is configured to assume:

an unlocked state, in which (a) the distal and the proximal coupling elements are interlockedly coupled with one other, and (b) the distal spring depressor restrains the spring in an axially-compressed state, in which state the spring does not inhibit sliding of the tether through the lateral opening, and a locked state, in which (b) the distal and the proximal coupling elements are not coupled with one another, (b) the distal spring depressor does not restrain the spring in the axially-compressed state, and (c) the spring is in an axially-expanded state, in which state the spring inhibits the sliding of the tether through the lateral opening by pressing the tether against the outer tether-securing element.

For some applications, at least a portion of the spring radially surrounds the axially-stationary shaft.

For some applications, at least a portion of the spring is helical.

For some applications, when the tissue-anchor system is in the locked state, the spring inhibits the sliding of the tether through the lateral opening by pressing the tether against a perimeter of the lateral opening of the outer tether-securing element.

For some applications:

the tissue-anchor system further includes a locking wire, the torque-delivery cable, including the distal torque-delivery head, the distal coupling element, the proximal coupling element, and the axially-stationary shaft are shaped so as define respective channels therethrough, which are radially aligned with each other and coaxial with the tissue anchor, and when the tissue-anchor system is in the unlocked state, a portion of the locking wire is disposed in the channels, thereby preventing decoupling of the distal and the proximal coupling elements from one another.

For some applications:

the anchor head further includes a hammer cap, which is fixed to the spring, and covers at least a portion of the spring, including a proximal end of the spring, and when the tissue-anchor system is in the locked state, the spring presses the tether against the outer tether-securing element by pressing the hammer cap against the outer tether-securing element.

For some applications, when the tissue-anchor system is in the locked state, the spring presses the hammer cap against a perimeter of the lateral opening of the outer tether-securing element.

For some applications, the outer tether-securing element is rotatable with respect to the tissue-coupling element and the axially-stationary shaft.

For some applications, the outer tether-securing element is shaped as a partial cylinder.

For some applications, the tissue anchor is a first tissue anchor, and the tissue-anchor system further includes a second tissue anchor, to which the tether is fixed.

For some applications:

the torque-delivery tool is a first torque-delivery tool,
the torque-delivery cable is a first torque-delivery cable,
the distal torque-delivery head is a first distal torque-delivery head,
the distal coupling element is a first distal coupling element,
the distal end of the distal torque-delivery head is a first distal end of the first torque-delivery head,
the distal spring depressor is a first distal spring depressor,
the tissue-coupling element is a first tissue-coupling element,
the anchor head is a first anchor head,
the proximal portion of the tissue-coupling element is a first proximal portion of the first tissue-coupling element,
the axially-stationary shaft is a first axially-stationary shaft,
the distal portion of the axially-stationary shaft is a first distal portion of the first axially-stationary shaft,
the proximal end of the axially-stationary shaft is a first proximal end of the first axially-stationary shaft,
the proximal coupling element is a first proximal coupling element,
the corresponding interlocking surfaces are first corresponding interlocking surfaces,
the spring is a first spring,
the outer tether-securing element is a first outer tether-securing element,
the lateral opening is a first lateral opening, and
the tissue-anchor system further includes:
a second torque-delivery tool, which includes (a) a second torque-delivery cable, which includes a second distal torque-delivery head, (b) a second distal coupling element that is fixed to a second distal end of the second distal torque-delivery head, and (c) a second distal spring depressor;
a third tissue anchor, which includes (a) a second tissue-coupling element, and (h) a second anchor head, which (i) is attached to a second proximal portion of the second tissue-coupling element, and (ii) includes:
a second axially-stationary shaft, which (a) has a second distal portion that is axially fixed with respect to the second proximal portion of the second tissue-coupling element, and (b) has a second proximal end that includes a second proximal coupling element, wherein the second distal and the second proximal coupling elements are shaped so as to define second corresponding interlocking surfaces;
a second spring; and
a second outer tether-securing element, which (a) is shaped so as to define a second lateral opening through which the tether is disposed, and (b) at least partially radially surrounds the second axially-stationary shaft and the second spring,
wherein the second tissue-anchor system is configured to assume:
an unlocked state, in which (a) the second distal and the second proximal coupling elements are interlockedly coupled with one other, and (b) the second distal spring depressor restrains the second spring in an axially-compressed state, in which state the second spring does not inhibit sliding of the tether through the second lateral opening, and
a locked state, in which (b) the second distal and the second proximal coupling elements are not coupled with one another, (b) the second distal spring depressor does not restrain the second spring in the axially-compressed state, and (c) the second spring is in an axially-expanded state, in which state the second spring inhibits the sliding of the tether through the second lateral opening by pressing the tether against the second outer tether-securing element.

There is still further provided, in accordance with an application of the present invention, apparatus including a tissue-anchor system, which includes:

a tissue anchor, which includes (a) a helical tissue-coupling element, which is shaped so as to define and surrounds a helical tissue-coupling element channel that extends to a distal end of the helical tissue-coupling element, and (b) an anchor head, which (i) is attached to a proximal portion of the helical tissue-coupling element, and (ii) is shaped so as to define a head-coupling channel, which has an internal wall;
a locking shaft having a sharp distal tip; and
a torque-delivery tool, which includes:
(a) a torque-delivery cable;
(b) a distal torque-delivery head, which:
(i) is fixed to the torque-delivery cable, and
(ii) is shaped so as to define a chamber, which is shaped so as to define:
(A) a fenestration through a lateral wall of the chamber, and
(B) proximal and distal chamber end openings; and
(c) a coupling element, which is:
(i) not fixed to any elements of the tissue-anchor system,
(ii) too large to pass through the fenestration; and
(iii) too large to pass through the distal chamber end opening,
wherein the torque-delivery cable and the distal torque-delivery head together are shaped so as to define a locking shaft-accepting channel, which:
(a) passes through (i) the torque-delivery cable, (ii) the chamber, and (iii) the proximal and the distal chamber end openings, and
(b) is coaxial with the helical tissue-coupling element channel,
wherein the tissue-anchor system is configured to assume engaged and disengaged states, in which the distal torque-delivery head is engaged and not engaged to the anchor head, respectively, and
wherein the tissue-anchor system is in:
the engaged state when the locking shaft is removably disposed in the locking-wire-accepting channel and at least partially within the helical tissue-coupling element channel, with the locking shaft constraining the coupling element to partially protrude through the fenestration out of the chamber and against the internal wall of the head-coupling channel, thereby axially locking the distal torque-delivery head with respect to the head-coupling channel, and
the disengaged state when the locking shaft is not disposed in the locking-wire-accepting channel and is not disposed in the helical tissue-coupling element channel, and does not constrain the coupling element.

For some applications, the tissue-anchor system further includes a tether, which is coupled to the anchor head.

For some applications, the tether is fixed to the anchor head.

For some applications, the coupling element is too large to pass through the proximal chamber end opening.

For some applications, the coupling element is spherical.

For some applications, the coupling element has a volume of between 0.3 and 8 mm3.

For some applications, the coupling element includes a metal.

For some applications, the coupling element includes a polymer.

For some applications, the polymer includes an elastomer.

For some applications, the locking shaft is shaped so as to define one or more longitudinally-extending grooves.

For some applications, the locking shaft is shaped so as to define one or more longitudinally-extending flat surfaces.

For some applications, the locking shaft is shaped so as to define a plurality of longitudinally-extending flat surfaces facing in respective different directions.

For some applications:

the internal wall of the head-coupling channel is shaped so as to define a coupling indentation, and the tissue-anchor system is in the engaged state when the locking shaft is removably disposed in the locking-wire-accepting channel and at least partially within the helical tissue-coupling element channel, with the locking shaft constraining the coupling element to partially protrude through the fenestration out of the chamber and into the coupling indentation of the internal wall of the head-coupling channel.

For some applications:

the torque-delivery tool further includes a depth-finding tool, which includes a radiopaque bead shaped so as to define a hole therethrough, the bead is removably positioned within the helical tissue-coupling element channel, and the locking shaft passes through the hole of the bead, such that the bead is slidable along the locking shaft and along the helical tissue-coupling element channel, when the locking shaft is removably disposed at least partially within the helical tissue-coupling element channel when the tissue-anchor system is in the engaged state.

For some applications, the depth-finding tool further includes a bead-coupling wire, which is at least partially disposed within the helical tissue-coupling element channel, and which is fixed to the bead and a distal portion of the distal torque-delivery head, thereby preventing the bead from exiting a distal end of the helical tissue-coupling element channel.

For some applications, the bead-coupling wire is shaped as a helical spring.

There is additionally provided, in accordance with an application of the present invention, apparatus including a sterile flexible tether, wherein, when the tether is tensioned into a straight configuration:

the tether has a central longitudinal axis, and is shaped so as to define first and second blades, which are disposed (a) at first and second longitudinal locations, and (h) within 10 mm of one another along the central longitudinal axis, and the first and the second blades have respective best-fit planes, which intersect at an angle of at least 30 degrees.

For some applications, the central longitudinal axis falls in the first and the second best-fit planes.

For some applications, the central longitudinal axis is parallel to the first and the second best-fit planes.

For some applications, the angle is at least 60 degrees, such as at least 85 degrees.

For some applications, the first and the second blades have respective first and second greatest dimensions perpendicular to the central longitudinal axis, each of which is between 0.25 and 5 mm.

For some applications:

the first and the second blades have respective first and second greatest major dimensions perpendicular to the central longitudinal axis, the first and the second blades have respective first and second greatest minor dimensions, which are measured perpendicular to (a) the first and the second greatest major dimensions, respectively, and (b) the central longitudinal axis, and the first and the second greatest minor dimensions equal no more than 50% of the first and the second greatest major dimensions, respectively.

For some applications, each of the first and the second major dimensions is between 0.25 and 5 mm. For some applications, each of the first and the second greatest minor dimensions is at least 0.05 mm.

For some applications, when the tether is tensioned into the straight configuration:

the tether is shaped so as to define a third blade, which is disposed (a) at a third longitudinal location, and (b) within 10 mm of the second blade along the central longitudinal axis, wherein the second longitudinal location is longitudinally between the first and the third longitudinal locations along the central longitudinal axis, the third blade has a third best-fit plane, which intersects the second best-fit plane at an angle of at least 30 degrees.

For some applications, the first blade is shaped so as to define at least one flat planar surface portion having a cross-sectional area of at least 0.25 mm2.

For some applications, the first blade is shaped so as to define at least two non-coplanar flat planar surface portions, each of which has the area of at least 0.25 mm2.

For some applications, the at least two flat planar surface portions are parallel to one another.

For some applications, the second blade is shaped so as to define at least one flat planar surface portion having a cross-sectional area of at least 0.25 mm2.

For some applications, the first and the second blades have a same shape, which has different rotational orientations about the central longitudinal axis at the first and the second longitudinal locations.

For some applications, the tether includes a polymer.

For some applications, the tether includes a polymer/metal composite material.

For some applications, the first and the second blades have respective first and second greatest cross-sectional areas, measured perpendicular to central longitudinal axis, each of which is between 0.1 and 20 mm2.

For some applications, the first and the second blades have respective first and second volumes, each of which is between 0.05 and 150 mm3.

For some applications, an average cross-sectional area of the tether is less than 20 mm2.

For some applications, a greatest cross-sectional area of the tether is less than 20 mm2.

For some applications, a plane defined by a longitudinal edge of the first blade forms an angle with the central longitudinal axis of at least 60 degrees.

For some applications, the first and the second blades are separated by a blade-free longitudinal gap, which has a length of at least 0.25 mm.

For some applications, the apparatus further includes a tissue anchor, which includes a tissue-coupling element and an anchor head, which is shaped so as to define an opening through which the tether passes.

For some applications, the tissue anchor further includes a spring, which is configured to inhibit sliding of the tether through the opening.

There is yet additionally provided, in accordance with an application of the present invention, apparatus including a sterile flexible tether, wherein, when the tether is tensioned into a straight, untwisted configuration:

the tether has a central longitudinal axis, and is shaped so as to define first and second cross sections perpendicular to the central longitudinal axis, at first and second different longitudinal locations that are within 10 mm of one another along the central longitudinal axis, the first and the second cross sections have respective first and second greatest dimensions, which define respective first and second lines, and if the first and the second cross sections were to be projected onto one another while preserving rotation about the central longitudinal axis, (a) the first and the second lines would intersect at an angle of at least 30 degrees, and (b) the first and the second cross sections would not coincide.

For some applications, the angle is at least 60 degrees.

For some applications, the angle is at least 85 degrees.

For some applications, each of the first and the second greatest dimensions is between 0.25 and 5 mm.

For some applications:

the first and the second greatest dimensions are first and second greatest major dimensions, the first and the second cross sections have respective first and second greatest minor dimensions, which are measured perpendicular to the first and the second greatest major dimensions, respectively, and the first and the second greatest minor dimensions equal no more than 50% of the first and the second greatest major dimensions, respectively.

For some applications, when the tether is tensioned into the straight, untwisted configuration:

the tether is shaped so as to define a third cross section perpendicular to the central longitudinal axis, at a third longitudinal location, wherein the second longitudinal location is longitudinally between the first and the third longitudinal locations along the central longitudinal axis, the third second cross section has a third greatest dimension, which defines a third line, and if the second and the third cross sections were to be projected onto one another while preserving rotation about the central longitudinal axis, (a) the second and the third lines would intersect at an angle of at least 30 degrees, and (b) the second and the third cross sections would not coincide.

For some applications, a first perimeter of the first cross section is shaped so as to define at least one straight line segment having a length of at least 0.5 mm.

For some applications, the first perimeter is shaped so as to define at least two non-coaxial straight line segments, each of which has the length of at least 0.5 mm.

For some applications, the at least two non-coaxial straight line segments are parallel to one another.

For some applications, a second perimeter of the second cross section is shaped so as to define at least one straight line segment having a length of at least 0.5 mm.

For some applications, the first and the second cross sections have a same shape, which has different rotational orientations about the central longitudinal axis at the first and the second longitudinal locations.

For some applications, when the tether is tensioned into the straight, untwisted configuration:

the tether is shaped so as to define a first longitudinal segment that includes the first longitudinal location and has a first length, measured along the central longitudinal axis, of at least 0.25 mm, the first longitudinal segment, at every longitudinal location therealong, has first cross sections, which (a) include the first cross section, and (b) have respective first greatest dimensions, which define respective first lines, which include the first line, and if the first cross sections were to be projected onto the second cross section while preserving rotation about the central longitudinal axis: (a) the first lines would intersect the second line at respective angles, each of at least 30 degrees, and (b) the first cross sections would not coincide with the second cross section.

For some applications, the first cross sections have a same shape.

For some applications, the shape has a same rotational orientation about the central longitudinal axis along the first longitudinal segment.

For some applications, the shape has different rotational orientations about the central longitudinal axis at at least two longitudinal locations along the first longitudinal segment.

For some applications, when the tether is tensioned into the straight, untwisted configuration:

the tether is shaped so as to define a second longitudinal segment that includes the second longitudinal location and has a second length, measured along the central longitudinal axis, of at least 0.25 mm, the second longitudinal segment, at every longitudinal location therealong, has second cross sections, which (a) include the second cross section, and (b) have respective second greatest dimensions, which define respective second lines, which include the second line, and if the second cross sections were to be projected onto the first cross section while preserving rotation about the central longitudinal axis: (a) the second lines would intersect the first line at respective angles, each of at least 30 degrees, and (b) the second cross sections would not coincide with the first cross section.

For some applications, the tether includes a polymer.

For some applications, the tether includes a polymer/metal composite material.

For some applications, the first and the second cross sections have first and second areas, respectively, each of which is between 0.1 and 20 mm2

For some applications, the tether is shaped so as to define at least three blades, which (a) include the first and the second blades, and (b) are disposed along a longitudinal portion of the tether, and an average cross-sectional area of the tether along the longitudinal portion is less than 20 mm2.

For some applications, the tether is shaped so as to define at least three blades, which (a) include the first and the second blades, and (b) are disposed along a longitudinal portion of the tether, and a greatest cross-sectional area of the tether is less than 20 mm2.

For some applications, the apparatus further includes a tissue anchor, which includes a tissue-coupling element and an anchor head, which is shaped so as to define an opening through which the tether passes.

For some applications, the tissue anchor further includes a spring, which is configured to inhibit sliding of the tether through the opening.

There is also provided, in accordance with an application of the present invention, a method including:

providing a torque-delivery tool of a tissue-anchor system, which torque-delivery tool includes (a) a torque-delivery cable, which includes a distal torque-delivery head, (b) a distal coupling element that is fixed to a distal end of the distal torque-delivery head, and (c) a distal spring depressor;

providing a tether of the tissue-anchor system; and providing a tissue anchor of the tissue-anchor system, which tissue anchor includes (a) a tissue-coupling element; and (b) an anchor head, which (i) is attached to a proximal portion of the tissue-coupling element, and (ii) includes:

an axially-stationary shaft, which (a) has a distal portion that is axially fixed with respect to the proximal portion of the tissue-coupling element, and (b) has a proximal end that includes a proximal coupling element, wherein the distal and the proximal coupling elements are shaped so as to define corresponding interlocking surfaces;

a spring; and an outer tether-securing element, which (a) is shaped so as to define a lateral opening through which the tether is disposed, and (b) at least partially radially surrounds the axially-stationary shaft and the spring, advancing the tissue-anchor system into a body of a subject, while the tissue-anchor system is in an unlocked state, in which (a) the distal and the proximal coupling elements are interlockedly coupled with one other, and (b) the distal spring depressor restrains the spring in an axially-compressed state, in which state the spring does not inhibit sliding of the tether through the lateral opening;

thereafter, using the torque-delivery cable, implanting the tissue anchor in tissue of the subject;

thereafter, applying tension to the tether; and thereafter, transitioning the tissue-anchor system to a locked state, in which (b) the distal and the proximal coupling elements are not coupled with one another, (b) the distal spring depressor does not restrain the spring in the axially-compressed state, and (c) the spring is in an axially-expanded state, in which state the spring inhibits the sliding of the tether through the lateral opening by pressing the tether against the outer tether-securing element.

For some applications, at least a portion of the spring radially surrounds the axially-stationary shaft.

For some applications, at least a portion of the spring is helical.

For some applications, when the tissue-anchor system is in the locked state, the spring inhibits the sliding of the tether through the lateral opening by pressing the tether against a perimeter of the lateral opening of the outer tether-securing element.

For some applications:

the tissue-anchor system further includes a locking wire, the torque-delivery cable, including the distal torque-delivery head, the distal coupling element, the proximal coupling element, and the axially-stationary shaft are shaped so as define respective channels therethrough, which are radially aligned with each other and coaxial with the tissue anchor, advancing the tissue-anchor system includes advancing the tissue-anchor system in the unlocked state while a portion of the locking wire is disposed in the channels, thereby preventing decoupling of the distal and the proximal coupling elements from one another, and transitioning the tissue-anchor system to the locked state includes withdrawing the locking wire from the channels.

For some applications:

the anchor head further includes a hammer cap, which is fixed to the spring, and covers at least a portion of the spring, including a proximal end of the spring, and when the tissue-anchor system is in the locked state, the spring presses the tether against the outer tether-securing element by pressing the hammer cap against the outer tether-securing element.

For some applications, when the tissue-anchor system is in the locked state, the spring presses the hammer cap against a perimeter of the lateral opening of the outer tether-securing element.

For some applications, the outer tether-securing element is rotatable with respect to the tissue-coupling element and the axially-stationary shaft.

For some applications, the outer tether-securing element is shaped as a partial cylinder.

There is further provided, in accordance with an application of the present invention, a method including:

endovascularly advancing and implanting a first tissue anchor at a first ventricular wall site selected from the group consisting of: a site on an anterior ventricular wall, and a site on a posterior ventricular wall;

endovascularly advancing and implanting a second tissue anchor at a second ventricular wall site on the anterior ventricular wall;

thereafter, approximating the first and the second ventricular wall sites by tensioning a tether between the first and the second tissue anchors;

thereafter, endovascularly advancing and implanting a third tissue anchor at a third ventricular wall site on an interventricular septum; and thereafter, approximating (a) the approximated first and second ventricular wall sites, collectively, and (b) the third ventricular wall site, by tensioning the tether between the second and the third tissue anchors.

For some applications, endovascularly advancing the first, the second, and the third tissue anchors includes percutaneously advancing the first, the second, and the third tissue anchors to the first, the second, and the third ventricular wall sites, respectively.

For some applications, the first ventricular wall site is on the anterior ventricular wall.

For some applications, the first ventricular wall site is below a level of papillary muscles.

For some applications, the second ventricular wall site is above a level of or at a junction of a natural moderator band and the anterior wall.

For some applications, the second ventricular wall site is no more than 2.5 cm from the first ventricular wall site.

For some applications, the third ventricular wall site is between a ventricular outflow tract (RVOT) and a junction of a natural moderator band and an interventricular septal wall.

For some applications, approximating the first and the second ventricular wall sites includes locking a tether-locking mechanism of the second tissue anchor after tensioning the tether between the first and the second tissue anchors.

For some applications, approximating (a) the approximated first and second ventricular wall sites, collectively, and (b) the third ventricular wall site includes locking a tether-locking mechanism of the third tissue anchor after tensioning the tether between the second and the third tissue anchors.

For some applications, the tether is electrically conductive.

For some applications, the tether is elastic.

There is still further provided, in accordance with an application of the present invention, a method including:

providing a tissue anchor of a tissue-anchor system, which tissue anchor includes (a) a helical tissue-coupling element, which is shaped so as to define and surrounds a helical tissue-coupling element channel that extends to a distal end of the helical tissue-coupling element, and (b) an anchor head, which (i) is attached to a proximal portion of the helical tissue-coupling element, and (ii) is shaped so as to define a head-coupling channel, which has an internal wall;

providing a locking shaft of the tissue-anchor system, which locking shaft has a sharp distal tip;

providing a torque-delivery tool of the tissue-anchor system, which torque-delivery tool includes (a) a torque-delivery cable, (b) a distal torque-delivery head, which (i) is fixed to the torque-delivery cable, and (ii) is shaped so as to define a chamber, which is shaped so as to define (A) a fenestration through a lateral wall of the chamber, and (B) proximal and distal chamber end openings, and (c) a coupling element, which is (i) not fixed to any elements of the tissue-anchor system, (ii) too large to pass through the fenestration, and (iii) too large to pass through the distal chamber end opening, wherein the torque-delivery cable and the distal torque-delivery head together are shaped so as to define a locking shaft-accepting channel, which (a) passes through (i) the torque-delivery cable, (ii) the chamber, and (iii) the proximal and the distal chamber end openings, and (b) is coaxial with the helical tissue-coupling element channel, and wherein the tissue-anchor system is configured to assume engaged and disengaged states, in which the distal torque-delivery head is engaged and not engaged to the anchor head, respectively;

advancing the tissue-anchor system into a body of a subject, while the tissue-anchor system is in the engaged state, while the locking shaft is removably disposed in the locking-wire-accepting channel and at least partially within the helical tissue-coupling element channel, with the locking shaft constraining the coupling element to partially protrude through the fenestration out of the chamber and against the internal wall of the head-coupling channel, thereby axially locking the distal torque-delivery head with respect to the head-coupling channel;

thereafter, using the torque-delivery cable, implanting the tissue anchor in tissue of the subject; and thereafter, transitioning the tissue-anchor system to the disengaged state by removing the locking shaft from the locking-wire-accepting channel and from the helical tissue-coupling element channel, such that the locking shaft does not constrain the coupling element.

For some applications, the method further includes providing a tether of the tissue-anchor system, which tether is coupled to the anchor head.

For some applications, the tether is fixed to the anchor head.

For some applications, providing the torque-delivery tool includes providing the torque-delivery tool in which the coupling element is too large to pass through the proximal chamber end opening.

For some applications, providing the torque-delivery tool includes providing the torque-delivery tool in which the coupling element is spherical.

For some applications, providing the torque-delivery tool includes providing the torque-delivery tool in which the coupling element has a volume of between 0.3 and 8 mm3.

For some applications, providing the torque-delivery tool includes providing the torque-delivery tool in which the coupling element includes a metal.

For some applications, providing the torque-delivery tool includes providing the torque-delivery tool in which the coupling element includes a polymer.

For some applications, providing the torque-delivery tool includes providing the torque-delivery tool in which the polymer includes an elastomer.

For some applications, providing the locking shaft includes providing the locking shaft that is shaped so as to define one or more longitudinally-extending grooves.

For some applications, providing the locking shaft includes providing the locking shaft that the locking shaft is shaped so as to define one or more longitudinally-extending flat surfaces.

For some applications, providing the locking shaft includes providing the locking shaft that the locking shaft is shaped so as to define a plurality of longitudinally-extending flat surfaces facing in respective different directions.

For some applications:

providing the tissue anchor includes providing the tissue anchor in which the internal wall of the head-coupling channel is shaped so as to define a coupling indentation, and the tissue-anchor system is in the engaged state when the locking shaft is removably disposed in the locking-wire-accepting channel and at least partially within the helical tissue-coupling element channel, with the locking shaft constraining the coupling element to partially protrude through the fenestration out of the chamber and into the coupling indentation of the internal wall of the head-coupling channel.

For some applications:

the method further includes providing a depth-finding tool of the torque-delivery tool, which depth-finding tool includes a radiopaque bead shaped so as to define a hole therethrough, advancing the tissue-anchor system into the body includes advancing the tissue-anchor system into the body while (a) the bead is removably positioned within the helical tissue-coupling element channel, and (b) the locking shaft passes through the hole of the bead, such that the bead is slidable along the locking shaft and along the helical tissue-coupling element channel, when the locking shaft is removably disposed at least partially within the helical tissue-coupling element channel when the tissue-anchor system is in the engaged state, and implanting the tissue anchor includes advancing the tissue-coupling element into the tissue, such that the bead comes in contact with and remains in contact with a surface of the tissue until removal of the depth-finding tool from the tissue anchor.

For some applications, providing the depth-finding tool includes providing the depth-finding tool that further includes a bead-coupling wire, which is at least partially disposed within the helical tissue-coupling element channel, and which is fixed to the bead and a distal portion of the distal torque-delivery head, thereby preventing the bead from exiting a distal end of the helical tissue-coupling element channel.

For some applications, the bead-coupling wire is shaped as a helical spring.

There is additionally provided, in accordance with an application of the present invention, a method including:

providing a sterile flexible tether, wherein, when the tether is tensioned into a straight configuration (1) the tether has a central longitudinal axis, and is shaped so as to define first and second blades, which are disposed (a) at first and second longitudinal locations, and (b) within 10 mm of one another along the central longitudinal axis, and (2) the first and the second blades have respective best-fit planes, which intersect at an angle of at least 30 degrees; and implanting the tether in a body of a subject.

For some applications, implanting the tether includes:

providing a tissue anchor, which includes a tissue-coupling element and an anchor head, which is shaped so as to define an opening through which the tether passes; and implanting the tissue anchor in tissue of the body.

For some applications, the tissue anchor further includes a spring, which is configured to inhibit sliding of the tether through the opening.

For some applications:

the first and the second blades are separated by a blade-free longitudinal gap, which has a length of at least 0.25 mm, and the method further includes advancing the tether with respect to the opening of the anchor head, by (a) pulling the tether until the gap is in the opening, (b) rotating the tether, and (c) pulling the tether in a desired direction of advancement.

For some applications, the central longitudinal axis falls in the first and the second best-fit planes.

For some applications, the central longitudinal axis is parallel to the first and the second best-fit planes.

For some applications, the angle is at least 60 degrees, such as at least 85 degrees.

For some applications, the first and the second blades have respective first and second greatest dimensions perpendicular to the central longitudinal axis, each of which is between 0.25 and 5 mm.

For some applications:

the first and the second blades have respective first and second greatest major dimensions perpendicular to the central longitudinal axis, the first and the second blades have respective first and second greatest minor dimensions, which are measured perpendicular to (a) the first and the second greatest major dimensions, respectively, and (b) the central longitudinal axis, and the first and the second greatest minor dimensions equal no more than 50% of the first and the second greatest major dimensions, respectively.

For some applications, each of the first and the second major dimensions is between 0.25 and 5 mm.

For some applications, each of the first and the second greatest nor dimensions is at least 0.05 mm.

For some applications, when the tether is tensioned into the straight configuration:

the tether is shaped so as to define a third blade, which is disposed (a) at a third longitudinal location, and (b) within 10 mm of the second blade along the central longitudinal axis, wherein the second longitudinal location is longitudinally between the first and the third longitudinal locations along the central longitudinal axis, the third blade has a third best-fit plane, which intersects the second best-fit plane at an angle of at least 30 degrees.

For some applications, the first blade is shaped so as to define at least one flat planar surface portion having a cross-sectional area of at least 0.25 mm2.

For some applications, the first blade is shaped so as to define at least two non-coplanar flat planar surface portions, each of which has the area of at least 0.25 mm2.

For some applications, the at least two flat planar surface portions are parallel to one another.

For some applications, the second blade is shaped so as to define at least one flat planar surface portion having a cross-sectional area of at least 0.25 mm2.

For some applications, the first and the second blades have a same shape, which has different rotational orientations about the central longitudinal axis at the first and the second longitudinal locations.

For some applications, the tether includes a polymer.

For some applications, the tether includes a polymer/metal composite material.

For some applications, the first and the second blades have respective first and second greatest cross-sectional areas, measured perpendicular to central longitudinal axis, each of which is between 0.1 and 20 mm2.

For some applications, the first and the second blades have respective first and second volumes, each of which is between 0.05 and 150 mm3.

For some applications, an average cross-sectional area of the tether is less than 20 mm2.

For some applications, a greatest cross-sectional area of the tether is less than 20 mm2.

For some applications, a plane defined by a longitudinal edge of the first blade forms an angle with the central longitudinal axis of at least 60 degrees.

For some applications, the first and the second blades are separated by a blade-free longitudinal gap, which has a length of at least 0.25 mm.

There is yet additionally provided, in accordance with an application of the present invention, a method including:

providing a sterile flexible tether, wherein, when the tether is tensioned into a straight, untwisted configuration (1) the tether has a central longitudinal axis, and is shaped so as to define first and second cross sections perpendicular to the central longitudinal axis, at first and second different longitudinal locations that are within 10 mm of one another along the central longitudinal axis, (2) the first and the second cross sections have respective first and second greatest dimensions, which define respective first and second lines, and (3) if the first and the second cross sections were to be projected onto one another while preserving rotation about the central longitudinal axis, (a) the first and the second lines would intersect at an angle of at least 30 degrees, and (b) the first and the second cross sections would not coincide; and implanting the tether in a body of a subject.

For some applications, implanting the tether includes:

providing a tissue anchor, which includes a tissue-coupling element and an anchor head, which is shaped so as to define an opening through which the tether passes; and implanting the tissue anchor in tissue of the body.

For some applications, the tissue anchor further includes a spring, which is configured to inhibit sliding of the tether through the opening.

For some applications:

the first and the second blades are separated by a blade-free longitudinal gap, which has a length of at least 0.25 mm, and the method further includes advancing the tether with respect to the opening of the anchor head, by (a) pulling the tether until the gap is in the opening, (b) rotating the tether, and (c) pulling the tether in a desired direction of advancement.

For some applications, the angle is at least 60 degrees, such as at least 85 degrees.

For some applications, s, each of the first and the second greatest dimensions is between 0.25 and 5 mm.

For some applications:
the first and the second greatest dimensions are first and second greatest major dimensions,
the first and the second cross sections have respective first and second greatest minor dimensions, which are measured perpendicular to the first and the second greatest major dimensions, respectively, and
the first and the second greatest minor dimensions equal no more than 50% of the first and the second greatest major dimensions, respectively.

For some applications, when the tether is tensioned into the straight, untwisted configuration:
the tether is shaped so as to define a third cross section perpendicular to the central longitudinal axis, at a third longitudinal location, wherein the second longitudinal location is longitudinally between the first and the third longitudinal locations along the central longitudinal axis,
the third second cross section has a third greatest dimension, which defines a third line, and
if the second and the third cross sections were to be projected onto one another while preserving rotation about the central longitudinal axis, (a) the second and the third lines would intersect at an angle of at least 30 degrees, and (b) the second and the third cross sections would not coincide.

For some applications, a first perimeter of the first cross section is shaped so as to define at least one straight line segment having a length of at least 0.5 mm.

For some applications, the first perimeter is shaped so as to define at least two non-coaxial straight line segments, each of which has the length of at least 0.5 mm.

For some applications, the at least two non-coaxial straight line segments are parallel to one another.

For some applications, a second perimeter of the second cross section is shaped so as to define at least one straight line segment having a length of at least 0.5 mm.

For some applications, the first and the second cross sections have a same shape, which has different rotational orientations about the central longitudinal axis at the first and the second longitudinal locations.

For some applications, when the tether is tensioned into the straight, untwisted configuration:
the tether is shaped so as to define a first longitudinal segment that includes the first longitudinal location and has a first length, measured along the central longitudinal axis, of at least 0.25 mm,
the first longitudinal segment, at every longitudinal location therealong, has first cross sections, which (a) include the first cross section, and (b) have respective first greatest dimensions, which define respective first lines, which include the first line, and
if the first cross sections were to be projected onto the second cross section while preserving rotation about the central longitudinal axis: (a) the first lines would intersect the second line at respective angles, each of at least 30 degrees, and (b) the first cross sections would not coincide with the second cross section.

For some applications, the first cross sections have a same shape.

For some applications, the shape has a same rotational orientation about the central longitudinal axis along the first longitudinal segment.

For some applications, the shape has different rotational orientations about the central longitudinal axis at at least two longitudinal locations along the first longitudinal segment.

For some applications, when the tether is tensioned into the straight, untwisted configuration:
the tether is shaped so as to define a second longitudinal segment that includes the second longitudinal location and has a second length, measured along the central longitudinal axis, of at least 0.25 mm,
the second longitudinal segment, at every longitudinal location therealong, has second cross sections, which (a) include the second cross section, and (b) have respective second greatest dimensions, which define respective second lines, which include the second line, and
if the second cross sections were to be projected onto the first cross section while preserving rotation about the central longitudinal axis: (a) the second lines would intersect the first line at respective angles, each of at least 30 degrees, and (b) the second cross sections would not coincide with the first cross section.

For some applications, the tether includes a polymer.

For some applications, the tether includes a polymer/metal composite material.

For some applications, the first and the second cross sections have first and second areas, respectively, each of which is between 0.1 and 20 mm2.

For some applications, the tether is shaped so as to define at least three blades, which (a) include the first and the second blades, and (b) are disposed along a longitudinal portion of the tether, and an average cross-sectional area of the tether along the longitudinal portion is less than 20 mm2.

For some applications, the tether is shaped so as to define at least three blades, which (a) include the first and the second blades, and (b) are disposed along a longitudinal portion of the tether, and a greatest cross-sectional area of the tether is less than 20 mm2.

The present invention will be more fully understood from the following detailed description of embodiments thereof, taken together with the drawings, in which:

BRIEF DESCRIPTION OF THE DRAWINGS

FIGS. 2A-B are schematic illustrations of the tissue-anchor system of FIGS. 1A-F in a locked state, in accordance with an application of the present invention;

FIGS. 3B-C are schematic illustrations of another tissue anchor in unlocked and locked states, respectively, in accordance with an application of the present invention;

FIGS. 3D-E are schematic illustrations of yet another tissue anchor in unlocked and locked states, respectively, in accordance with an application of the present invention;

FIGS. 5A-D are schematic illustrations of a tricuspid valve repair procedure using the tissue-anchor system of FIGS. 1A-F and 2A-B in a right atrium, in accordance with an application of the present invention;

FIGS. 6A-E are schematic illustrations of a tricuspid-mitral valve repair procedure, in accordance with an application of the present invention;

FIGS. 11A-D are schematic illustrations of a cutting tool, in accordance with an application of the present invention;

FIGS. 12A-C are schematic illustrations of a tissue anchor system in an engaged state, in accordance with an application of the present invention;

FIGS. 13A-B and 14A-B are schematic illustrations of the tissue anchor system of FIGS. 12A-C in a disengaged state, in accordance with an application of the present invention;

FIGS. 16A-C are schematic illustrations of two exemplary deployments of a tissue anchor of the tissue anchor system of FIGS. 12A-14B using a torque-delivery tool of the tissue anchor system of FIGS. 12A-14B, in accordance with respective applications of the present invention;

FIGS. 17A-19 are schematic illustrations of a flexible tether, in accordance with an application of the present invention;

FIGS. 20A-C are schematic illustrations of cross sections of the flexible tether of FIGS. 17A-19, in accordance with an application of the present invention;

FIGS. 21A-C are schematic illustrations of another configuration of the flexible tether of FIGS. 17A-19, in accordance with an application of the present invention;

FIGS. 24A-C are schematic illustrations of one use of the tether described hereinabove with reference to FIG. 21A-C, in accordance with an application of the present invention.

DETAILED DESCRIPTION OF APPLICATIONS

Figure 1A:
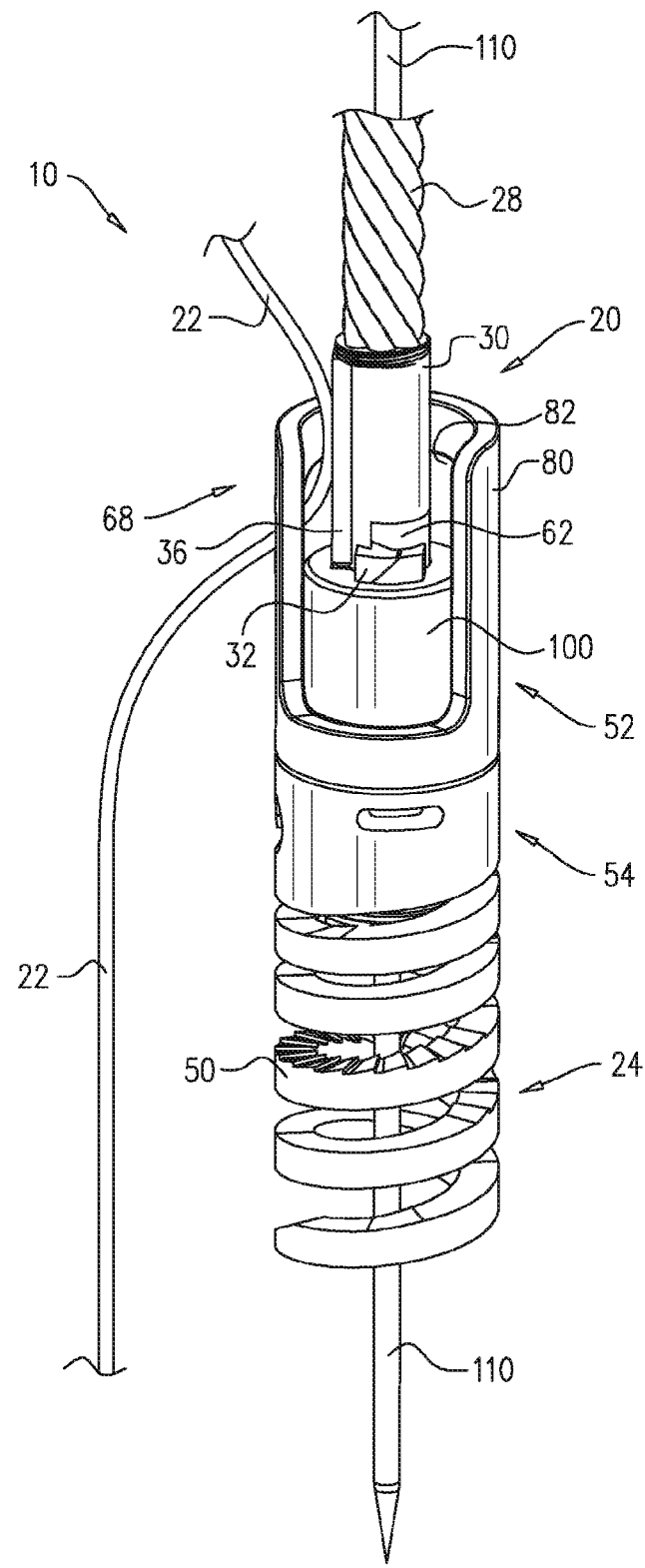
FIGS. 1A-F are schematic illustrations of a tissue-anchor system in an unlocked state, in accordance with an application of the present invention.
Figure 1B:
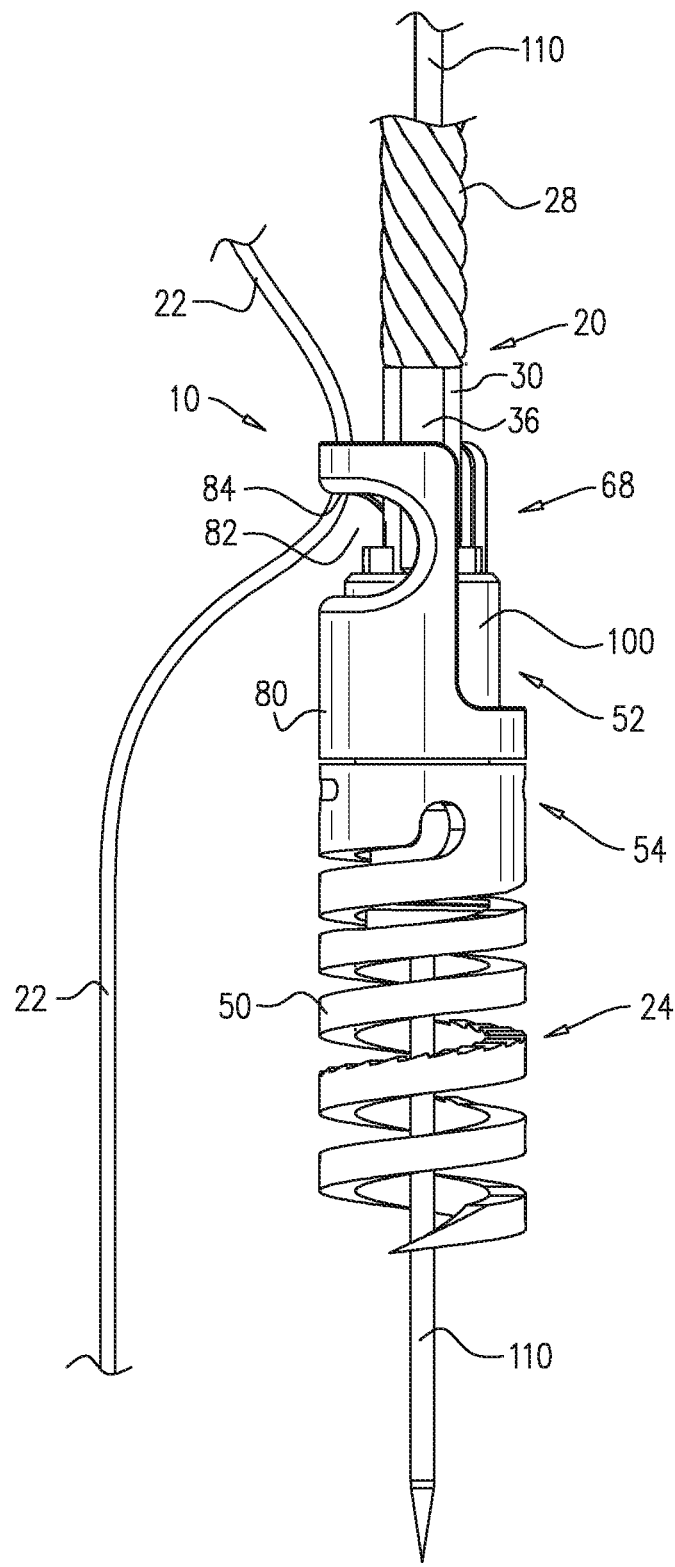
Figure 1C:
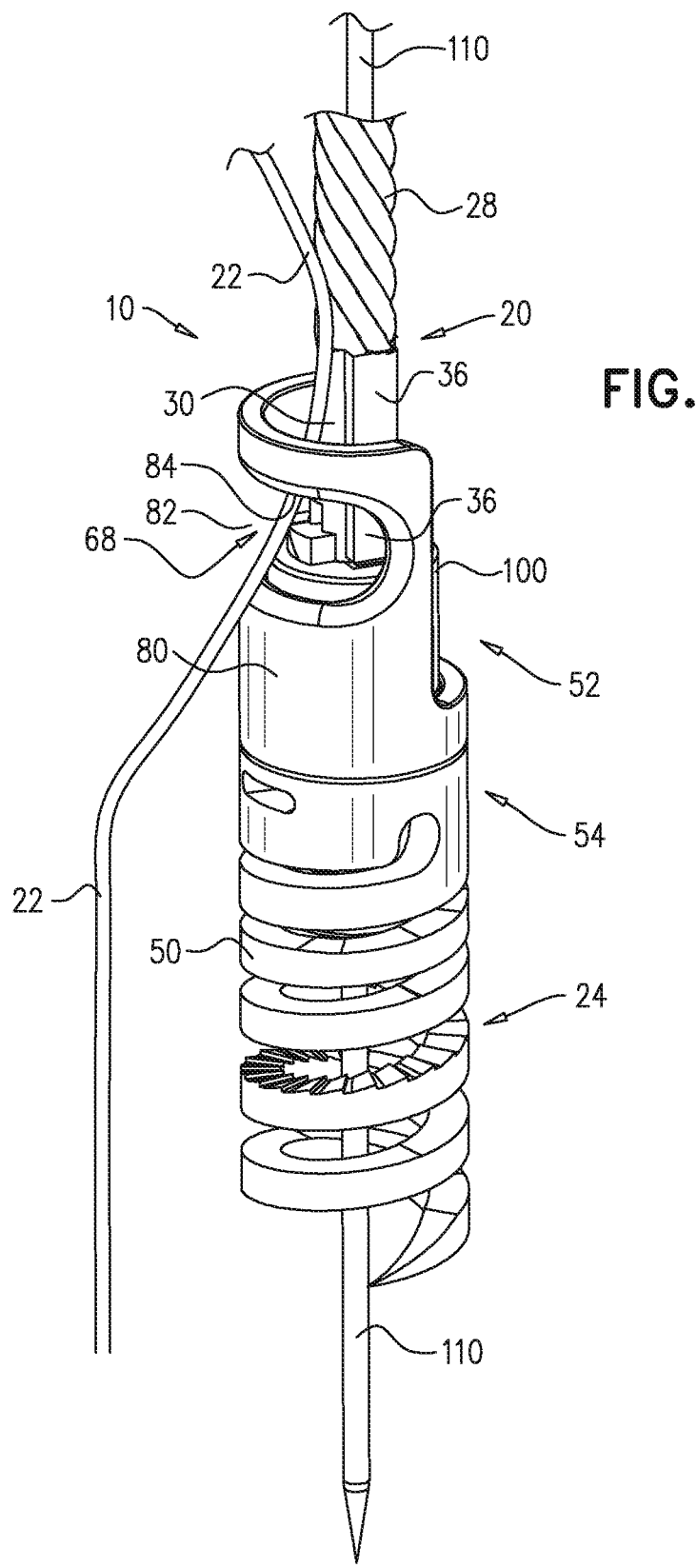

FIGS. 1A-F are schematic illustrations of a tissue-anchor system 10 in an unlocked state, in accordance with an application of the present invention. FIGS. 2A-B are schematic illustrations of tissue-anchor system 10 in a locked state, in accordance with an application of the present invention. Tissue-anchor system 10 comprises a torque-delivery tool 20, a tether 22, and a tissue anchor 24. Torque-delivery tool 20 is configured to implant tissue anchor 24 in cardiac tissue, and to thereafter lock tether 22 to tissue anchor 24, such that sliding of tether 22 with respect to tissue anchor 24 is inhibited. Typically, tether 22 is tensioned after tissue anchor 24 has been implanted in the cardiac tissue, and after the tether has been tensioned, tether 22 is locked to tissue anchor 24.

Torque-delivery tool 20 comprises (a) a torque-delivery cable 28, which comprises a distal torque-delivery head 30, (b) a distal coupling element 32 that is fixed to a distal end 34 of distal torque-delivery head 30, and (c) a distal spring depressor 36.

Tissue anchor 24 comprises (a) a tissue-coupling element 50, and (b) a proximal anchor head 52, which is attached to a proximal portion 54 of tissue-coupling element 50. For some applications, tissue-coupling element 50 comprises a helical tissue-coupling element, which punctures and screws into cardiac tissue. For some applications, tissue-coupling element 50 implements features of one or more of the tissue-coupling elements described in PCT Application PCT/IL2014/050027, filed Jan. 9, 2014, which published as PCT Publication WO 2014/108903 and is incorporated herein by reference.

Anchor head 52 comprises an axially-stationary shaft 56 and a tether-locking mechanism 68. Axially-stationary shaft 56 (which can best be seen in FIGS. 1D-F) has (a) a distal portion 58 that is axially fixed with respect to proximal portion 54 of tissue-coupling element 50, and (b) a proximal end 60 that comprises a proximal coupling element 62. Distal and proximal coupling elements 32 and 62 are shaped so as to define corresponding interlocking surfaces, which facilitate coupling of distal torque-delivery head 30 to axially-stationary shaft 56.

Tether-locking mechanism 68 comprises:
a spring 70 (which can best be seen in FIG. 1D) (for clarity of illustration of other elements, spring 70 is not shown in FIGS. 1E-F; the spring is actually present); and
an outer tether-securing element 80, which (a) is shaped so as to define a lateral opening 82 through which tether 22 is disposed, and (b) at least partially radially surrounds axially-stationary shaft 56 and spring 70 (and hammer cap 100, if provided, as described below). For some applications, as shown in the figures, outer tether-securing element 80 is shaped as a partial cylinder.

Figure 1D:
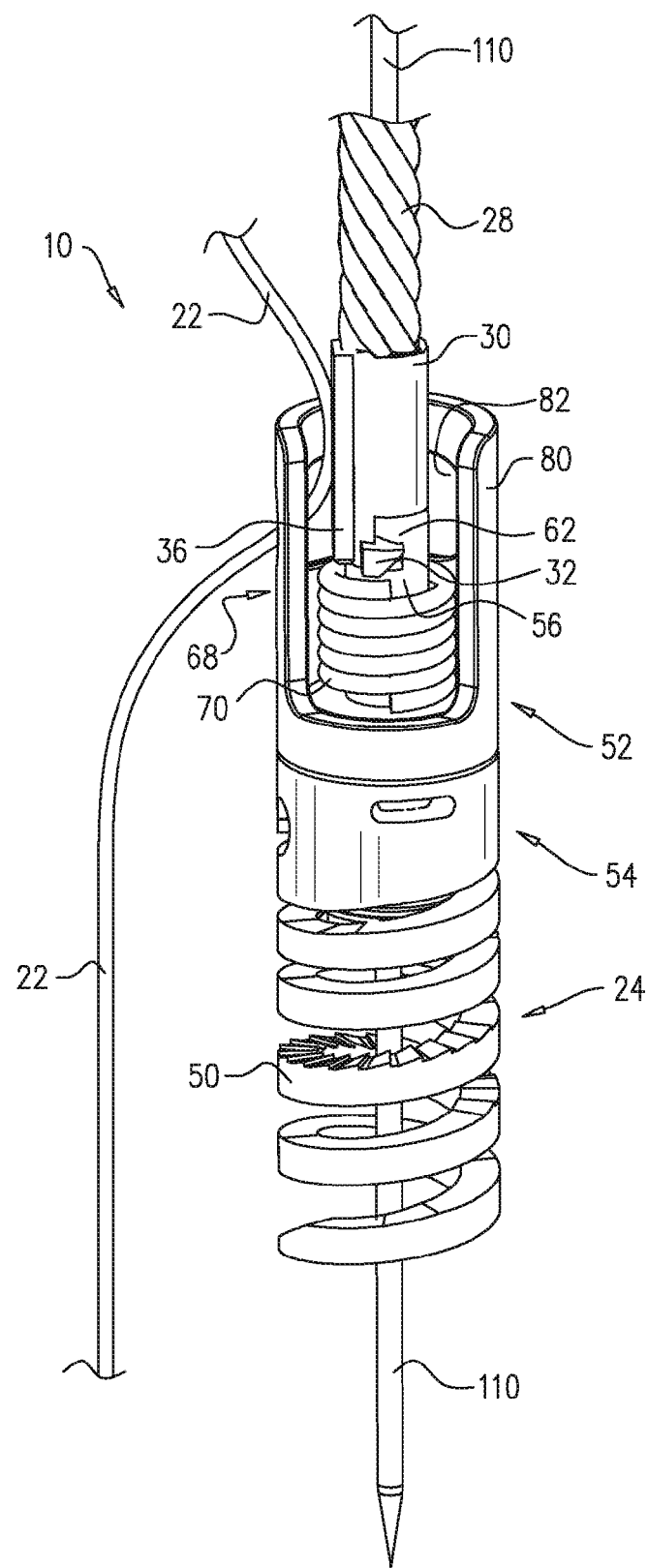
Figure 1E:
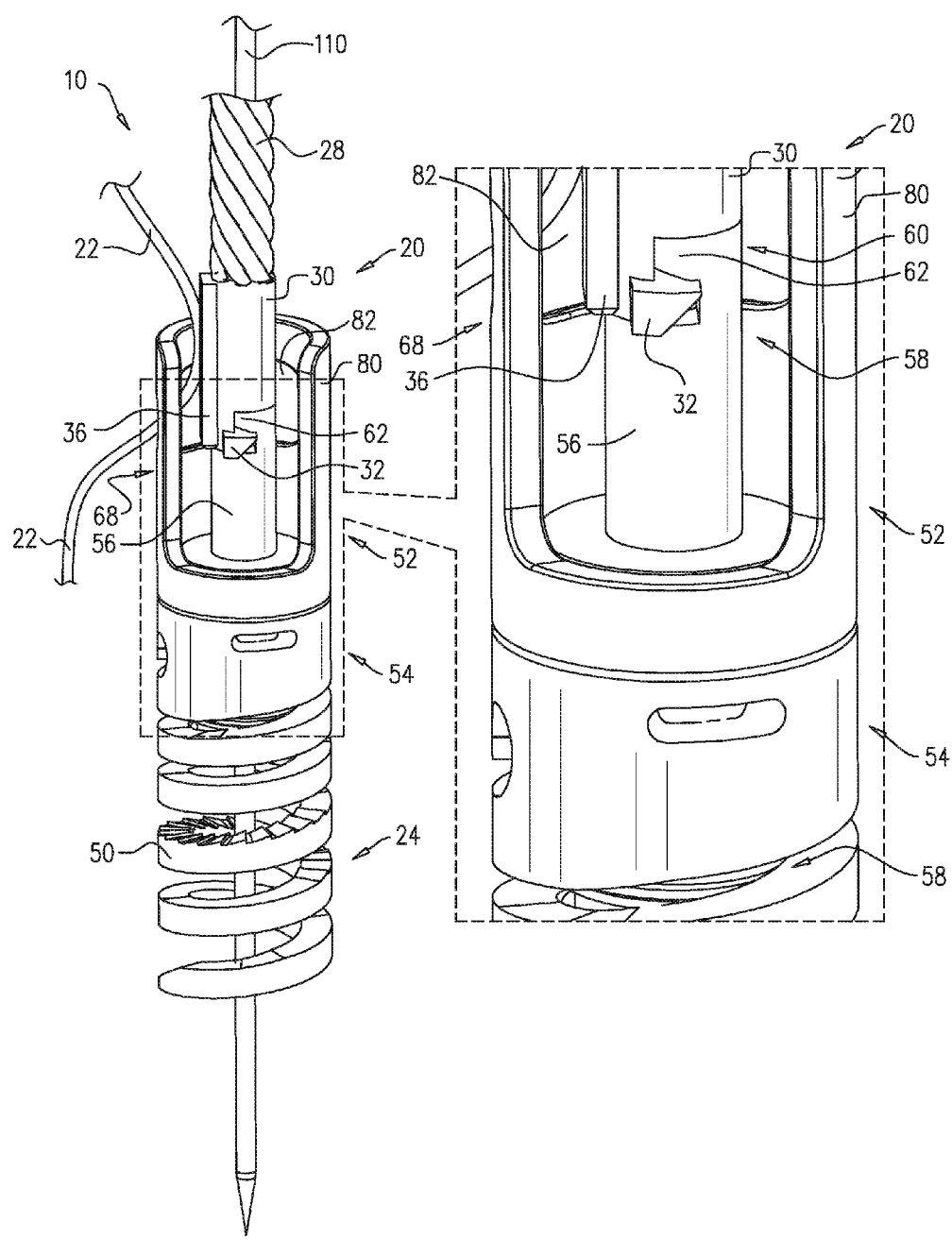
Figure 1F:
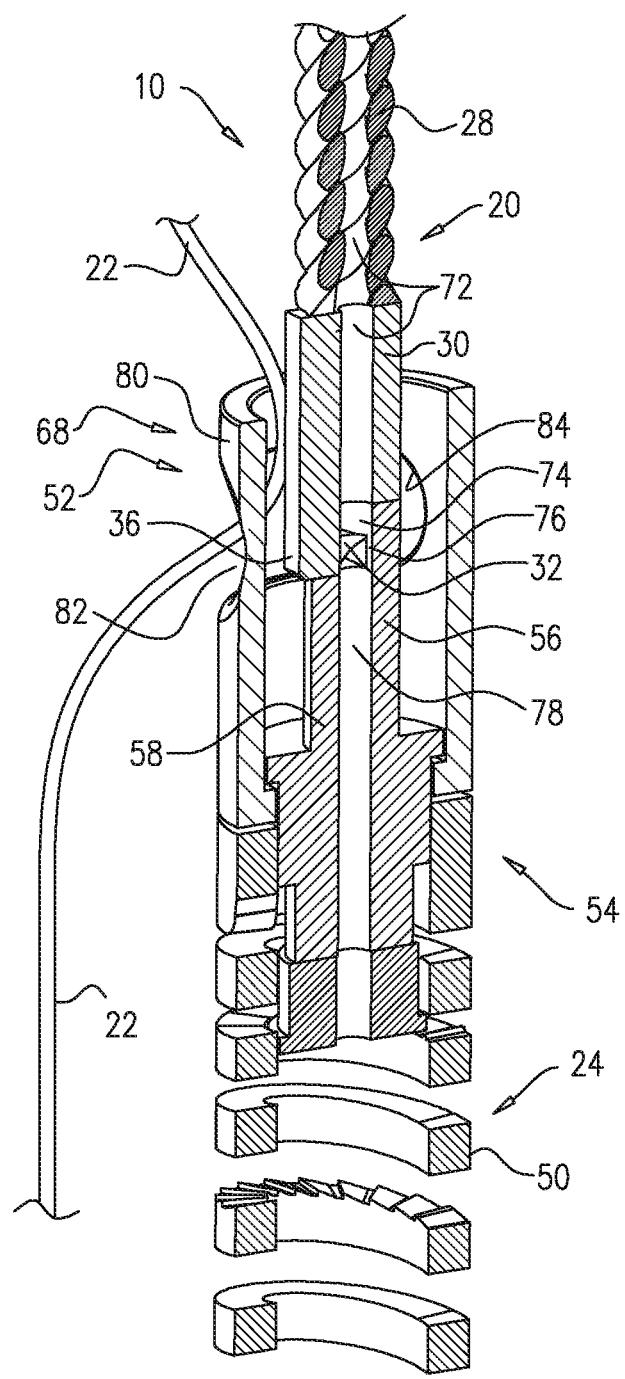
Figure 2A:
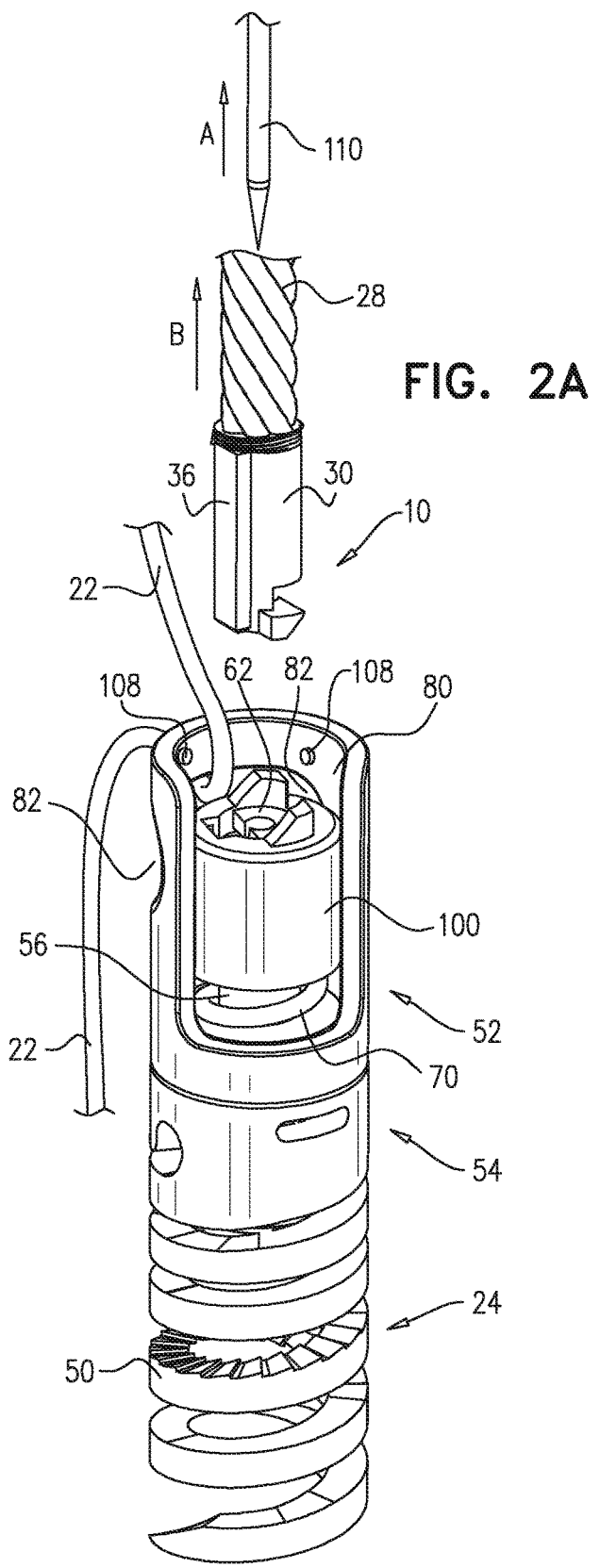

For some applications, at least a portion of spring 70 radially surrounds axially-stationary shaft 56, such as shown in FIG. 1D. For some applications, at least a portion of spring 70 is helical, such as shown in FIGS. 1D, 2A-B, and 3A (e.g., the entire spring is helical, such as shown in FIGS. 1D and 2A-B), while for other applications, spring 70 is not helical, such as described hereinbelow with reference to FIGS. 3B-E.

Tissue-anchor system 10 is configured to assume:
an unlocked state, as shown in FIGS. 1A-F, in which (a) distal and proximal coupling elements 32 and 62 are interlockedly coupled with one other, and (b) distal spring depressor 36 restrains spring 70 in an axially-compressed state, in which state spring 70 does not inhibit sliding of tether 22 through lateral opening 82, and
a locked state, as shown in FIGS. 2A-B, in which (a) distal and proximal coupling elements 32 and 62 are not coupled with one another, (b) distal spring depressor 36 does not restrain spring 70 in the axially-compressed state, and (c) spring 70 is in an axially-expanded state, in which state spring 70 inhibits the sliding of tether 22 through lateral opening 82 by pressing tether 22 against outer tether-securing element 80, such as against a perimeter 84 of lateral opening 82, and/or an inner surface of outer tether-securing element 80.

When tissue-anchor system 10 is in the unlocked state, tether-locking mechanism 68 is also in an unlocked state, in which state spring 70 does not inhibit sliding of tether 22 through lateral opening 82. When tissue-anchor system 10 is in the locked state, tether-locking mechanism 68 is also in a locked state, in which state spring 70 inhibits the sliding of tether 22 through lateral opening 82 by pressing tether 22 against outer tether-securing element 80, such as against perimeter 84 of lateral opening 82, and/or an inner surface of outer tether-securing element 80.

Tissue-anchor system 10 is advanced into the heart in the unlocked state. Tissue anchor 24 is implanted in cardiac tissue, using torque-delivery cable 28 while tissue-anchor system 10 is in the unlocked state. After tissue anchor 24 is implanted, tension is applied to tether 22. Thereafter, torque-delivery cable 28 (including distal torque-delivery head 30) is decoupled from axially-stationary shaft 56 of tissue anchor 24, thereby allowing spring 70 to expand and press tether 22 against outer tether-securing element 80. This pressing locks tether 22 with respect to tissue anchor 24, and maintains the distance and tension between tissue anchor 24 and one or more other implanted tissue anchors, such as described hereinbelow with reference to FIGS. 5C and 6E. Alternatively, tissue-anchor system 10 is used to implant tissue anchor 24 in non-cardiac tissue of a subject, in which case tissue-anchor system 10 is advanced into another location in the subject's body.

Torque-delivery cable 28 (including distal torque-delivery head 30) thus serves two functions:
- implanting tissue anchor 24 in cardiac tissue, by applying a rotational force to tissue anchor 24; and
- maintaining tissue-anchor system 10 in the unlocked state, in which state tether 22 can slide with respect to tissue anchor 24, allowing tension to be applied to the tether (and adjusted as necessary).

Similarly, decoupling of torque-delivery cable 28 (including distal torque-delivery head 30) from axially-stationary shaft 56 of anchor head 52 of tissue anchor 24 simultaneously (1) releases tissue anchor 24 and (2) transitions tissue-anchor system to the locked state.

For some applications, as can be seen in FIGS. 1A-C and FIGS. 2A-B, anchor head 52 further comprises a hammer cap 100, which is fixed to spring 70, and covers at least a portion 102 of spring 70, including a proximal end 104 of spring 70. (For clarity of illustration of other elements, hammer cap 100 is not shown in FIGS. 1D-F; the hammer cap is optionally present.) When tissue-anchor system 10 is in the locked state, spring 70 presses tether 22 against outer tether-securing element 80 by pressing hammer cap 100 against outer tether-securing element 80, such as perimeter 84 of lateral opening 82, and/or an inner surface of outer tether-securing element 80. Hammer cap 100 may prevent entanglement of tether 22 with spring 70. In addition, providing hammer cap 100 may obviate the need to weld a distal end of spring 70 to anchor head 52, because the hammer cap surrounds at least a portion of the spring and thereby couples the spring to the anchor head. For some applications, tether 22 prevents hammer cap 100 from proximally exiting outer tether-securing element 80. Alternatively or additionally, for some applications, one or more small pins 108 (shown in FIG. 2A) are provided that extend radially inward from an inner surface of outer tether-securing element 80; the pins prevent the hammer cap from proximally exiting the outer tether-securing element.

For some applications, tissue-anchor system 10 further comprises a locking wire 110. Torque-delivery cable 28 (including distal torque-delivery head 30), distal coupling element 32, proximal coupling element 62, and axially-stationary shaft 56 are shaped so as define respective channels 72, 74, 76, and 78 therethrough, which are radially aligned with each other and coaxial with tissue anchor 24. When tissue-anchor system 10 is in the unlocked state, a portion of locking wire 110 is disposed in the channels, thereby preventing decoupling of distal and proximal coupling elements 32 and 62 from one another. Proximal withdrawal and removal of the portion of locking wire 110 from the channels allows the decoupling of distal and proximal coupling elements 32 and 62 from one another.

For some applications, locking wire 110 is shaped so as to define a sharp distal tip 727. For these applications, tissue-coupling element 50 typically is helical, and locking wire 110 is initially removably positioned within a channel defined by the helix. As tissue-coupling element 50 is screwed into tissue, locking wire 110 penetrates and advances into the tissue along with the anchor to a certain depth in the tissue. For some applications, when the locking wire penetrates to the certain depth, the locking wire is withdrawn slightly. Typically, after tissue-coupling element 50 has been fully implanted, locking wire 110 is withdrawn entirely from the tissue, and removed from the subject's body. Optionally, sharp distal tip 727 of locking wire 110 is inserted into the tissue slightly, even before insertion of tissue-coupling element 50, in order to inhibit sliding of the tissue-coupling element on the surface of the tissue before commencement of insertion of the tissue-coupling element into the tissue.

For some applications, outer tether-securing element 80 is rotatable with respect to tissue-coupling element 50 and axially-stationary shaft 56, in order to provide rotational freedom of movement to tether 22 after implantation of tissue anchor 24, particularly during tensioning of tether 22. This rotational freedom of movement avoids twisting of the tether around the anchor head, and facilitates ideal orientation of the tether with another tissue anchor.

For some applications, outer tether-securing element 80 has an outer diameter of at least 1 mm, no more than 6 mm, and/or between 1 and 6 mm. For some applications, tissue anchor 24 has an outer diameter of at least 2 mm, no more than 8 mm, and/or between 2 and 8 mm.

Figure 3A:
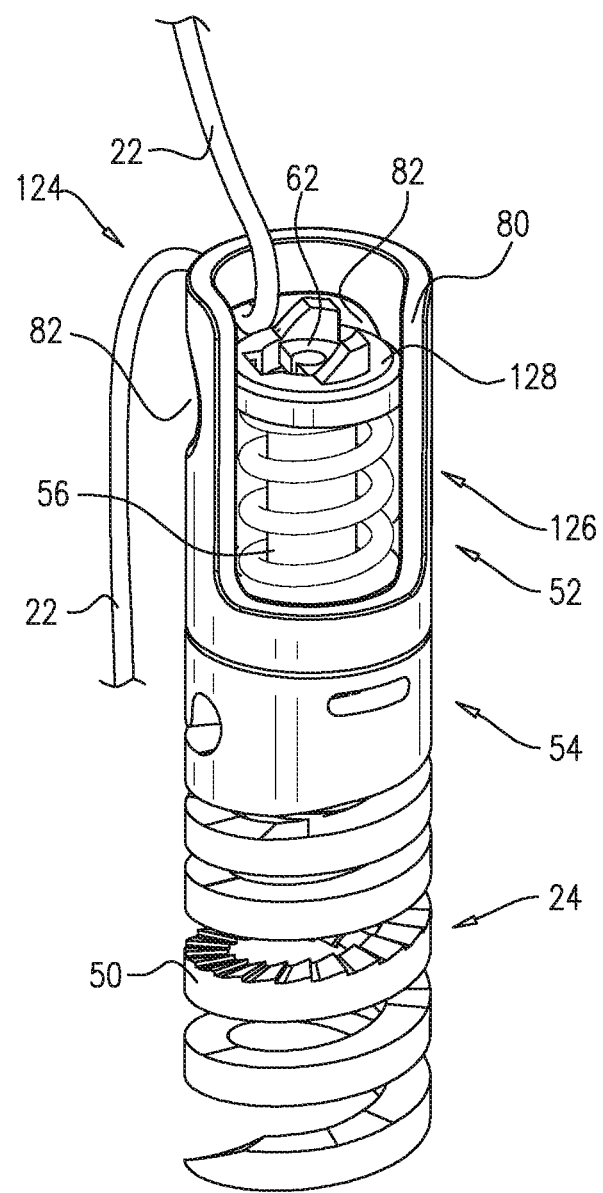
FIG. 3A is a schematic illustration of a tissue anchor, in accordance with an application of the present invention.

Reference is now made to FIG. 3A, which is a schematic illustration of a tissue anchor 124, in accordance with an application of the present invention. Except as described below, tissue anchor 124 is generally similar to tissue anchor 24, and may be used in tissue-anchor system 10 instead of tissue anchor 24 in any of the applications described herein. Tissue anchor 124 comprises a spring 126, which is shaped to provide a proximal surface 128 that presses tether 22 against outer tether-securing element 80, such as against perimeter 84 of lateral opening 82, and/or an inner surface of outer tether-securing element 80, when tissue-anchor system 10 is in the locked state, such as shown in FIG. 3A. Typically, at least a portion of spring 126 that does not provide proximal surface 128 is helical. For some applications, proximal surface 128 is circular. Proximal surface 128 may serve as a hammer head that presses tether 22 against outer tether-securing element 80 when tissue-anchor system 10 is in the locked state.

Reference is now made to FIGS. 3B-C, which are schematic illustrations of a tissue anchor 134 in unlocked and locked states, respectively, in accordance with an application of the present invention. Except as described below, tissue anchor 134 is generally similar to tissue anchor 24, and may be used in tissue-anchor system 10 instead of tissue anchor 24 in any of the applications described herein. Tissue anchor 134 comprises (a) a spring 136, which comprises an elastic band 138, and (b) a hammer element 140. Hammer element 140 is shaped to provide a proximal surface 142 that presses tether 22 against outer tether-securing element 80, such as against perimeter 84 of lateral opening 82, and/or an inner surface of outer tether-securing element 80, when tissue-anchor system 10 is in the locked state, as shown in FIG. 3C. Elastic band 138 of spring 136 and hammer element 140 are arranged such that elastic band 138 applies a proximal force on a distal end of hammer element 140. For some applications, proximal surface 142 is circular. Proximal surface 142 may serve as a hammer head that presses tether 22 against outer tether-securing element 80 when tissue-anchor system 10 is in the locked state.

Reference is now made to FIGS. 3D-E, which are schematic illustrations of a tissue anchor 144 in unlocked and locked states, respectively, in accordance with an application of the present invention. Except as described below, tissue anchor 144 is generally similar to tissue anchor 24, and may be used in tissue-anchor system 10 instead of tissue anchor 24 in any of the applications described herein. Tissue anchor 144 comprises (a) a spring 146, which comprises an expandable material 148, and (b) a hammer element 150. For example, expandable material 148 may comprise an expandable elastomeric material, a foam (e.g., foamed silicone), or a sponge, as is known in the materials arts. Hammer element 150 is shaped to provide a proximal surface 152 that presses tether 22 against outer tether-securing element 80, such as against perimeter 84 of lateral opening 82, and/or an inner surface of outer tether-securing element 80, when tissue-anchor system 10 is in the locked state, as shown in FIG. 3E. Expandable material 148 of spring 146 and hammer element 150 are arranged such that expandable material 148 applies a proximal force on a distal end of hammer element 150. For some applications, proximal surface 142 is circular. Proximal surface 152 may serve as a hammer head that presses tether 22 against outer tether-securing element 80 when tissue-anchor system 10 is in the locked state.

Reference is now made to FIGS. 4A-E, which are schematic illustrations of friction-enhancing features of tether 22, in accordance with respective applications of the present invention. These features may be used with tether 22 in any of the configurations described herein. The friction-enhancing features enhance friction between the tether and outer tether-securing element 80, when tissue-anchor system 10 is in the locked state (and tether-locking mechanism 68 is in the locked state). For some applications, these friction-enhancing features enable one-way ratcheting of tether 22 through lateral opening 82 of outer tether-securing element 80.

In these configurations, tether 22 typically defines a plurality of securement protrusions 160 spaced at intervals (I) along tether 22, which protrusions serve as the friction-enhancing features. For some applications, an average interval of securement protrusions 160 along tether 22 is at least 1 mm, no more than 18 mm, and/or between 1 and 18 mm, e.g., at least 3 mm, no more than 18 mm, and/or between 3 and 18 mm. For some applications, securement protrusions 160 have an outer diameter of at least 0.3 mm (e.g., at least 0.4 mm, such as at least 1 mm), no more than 6 mm (such as no more than 1.25 mm), and/or between 0.3 mm and 6 mm, such as between 0.4 mm and 1.25 mm. The outer diameter is typically less than the greatest dimension of lateral opening 82. For some applications, tether 22 comprises between 2 and 20 securement protrusions 160.

Figure 4A:
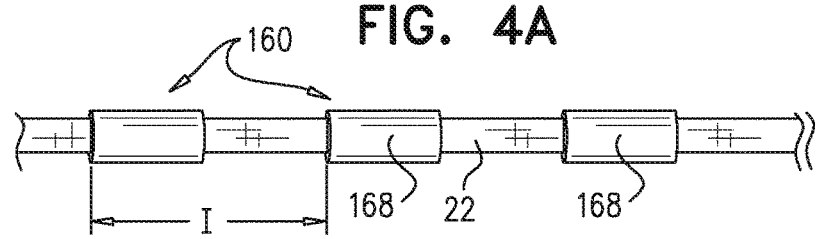
FIGS. 4A-E are schematic illustrations of friction-enhancing features of a tether of the tissue-anchor system of FIGS. 1A-F and 2A-B, in accordance with respective applications of the present invention.
Figure 4B:
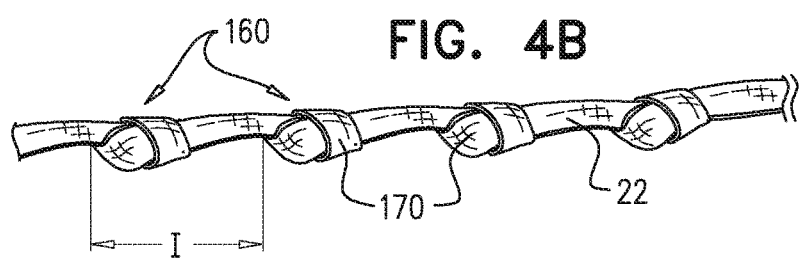
Figure 4C:
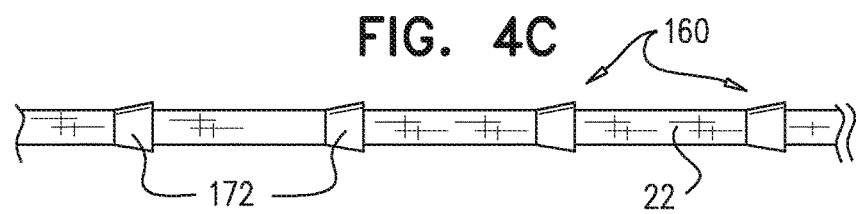
Figure 4D:
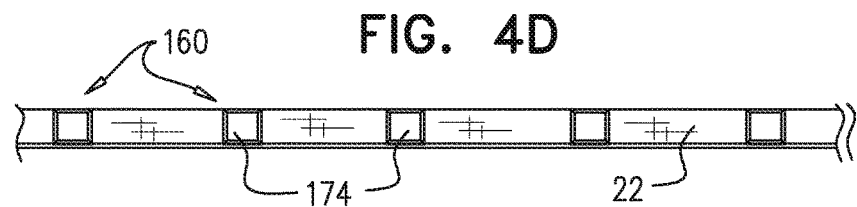
Figure 4E:
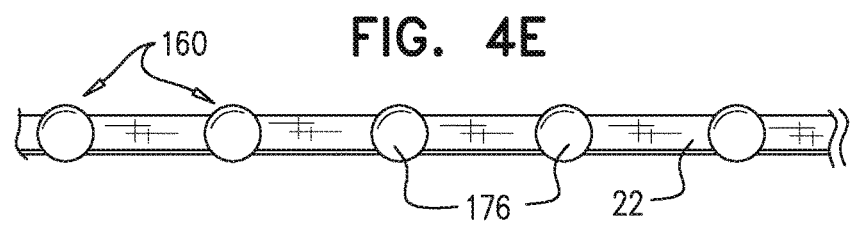

For some applications, protrusions 160 comprise respective cylinders 168 on tether 22, such as shown in FIG. 4A. For some applications, protrusions 160 are defined by respective knots 170 in tether 22, such as shown in FIG. 4B. For some applications, protrusions 160 comprise respective cones 172 on tether 22, such as shown in FIG. 4C; this configuration may restrict retrograde movement of the tether through outer tether-securing element 80, while allowing antegrade movement. For some applications, protrusions 160 comprise respective scales 174 on tether 22, such as shown in FIG. 4D. For some applications, protrusions 160 comprise respective beads 176 on tether 22, such as shown in FIG. 4E. For some of the applications described with reference to FIGS. 4A, 4C, 4D, and 4E, the elements the protrusions comprise are crimped to an outer surface of the tether. For some of the applications described with reference to FIGS. 4A, 4C, 4D, and 4E, protrusions 160 comprise a radiopaque material; which enhances fluoroscopy feedback to the user, particularly as the protrusions 160 are advanced through lateral opening 82 during application of tension to tether 22.

Reference is now made to FIGS. 5A-D, which are schematic illustrations of a tricuspid valve repair procedure using tissue-anchor system 10 in a right atrium 200, in accordance with an application of the present invention. The procedure is performed using a valve-tensioning implant system 202. Valve-tensioning implant system 202 comprises tissue-anchor system 10, including torque-delivery tool 20, tether 22, and tissue anchor 24, as described hereinabove with reference to FIGS. 1A-4E. In this procedure, tissue anchor 24 serves as a second tissue anchor 24. Valve-tensioning implant system 202 further comprises a first tissue anchor 204, which typically comprises a helical tissue-coupling element, which punctures and screws into cardiac muscle tissue. For some applications, first tissue anchor 204 implements techniques of one or more of the tissue anchors described in International Application PCT/IL2014/050027, filed Jan. 9, 2014, which published as PCT Publication WO 2014/108903 and is incorporated herein by reference. Alternatively, first tissue anchor 204 comprises a clip, jaws, or a clamp which grips and squeezes a portion of cardiac muscle tissue and does not puncture the cardiac muscle tissue. For some applications, a head 208 of first tissue anchor 204 comprises an interface 210 that is configured to rotate with respect to a helical tissue-coupling element 212 of tissue anchor 204, in order to provide rotational freedom of movement to tether 22 after implantation of the tissue anchor. Tether 22 is typically fixed to interface 210, such that tether 22 cannot slide with respect to interface 210.

Valve-tensioning implant system 202 further comprises a catheter 206 and a tool for delivering first tissue anchor 204. For some applications, the tool implements techniques described with reference to FIGS. 21 and 22A-D of PCT Publication WO 2013/011502, which is incorporated herein by reference, mutatis mutandis. For some applications, catheter 206 comprises a steering mechanism, as is known in the catheter art.

Valve-tensioning implant system 202 is typically introduced transcatheterly and endovascularly (typically percutaneously), via catheter 206, with the aid of a guidewire, through vasculature of the subject, such as (a) via the femoral vein, through inferior vena cava 274, and into right atrium 200, (b) via the basilic vein, through the subclavian vein through superior vena cava 276, and into right atrium 200, or (c) via the external jugular vein, through the subclavian vein through superior vena cava 276, and into right atrium 200. The procedure is typically performed with the aid of imaging, such as fluoroscopy, transesophageal, transthoratic echocardiography, ICE, and/or echocardiography. The procedure may be performed using techniques described in US Patent Application Publication 2012/0035712, which is assigned to the assignee of the present application and is incorporated herein by reference, with reference to FIGS. 1A-D thereof, mutatis mutandis.

As shown in FIG. 5A, first tissue anchor 204 is implanted at a first atrial site 292. Typically, first atrial site 292 is selected from the group of sites consisting of: an annulus 283 of a tricuspid valve 207; and a wall of right atrium 200 above annulus 283 of tricuspid valve 207. For some applications, first atrial site 292 is located within 1 cm of a site on annulus 283 that circumferentially corresponds to a location that is (a) at or counterclockwise to a point on the annulus that is 1 cm septal (i.e., clockwise) to a posteroseptal commissure 217, and (b) at or clockwise to a point on the annulus that is 1 cm anterior (i.e., counterclockwise) to an anteroposterior commissure (APC) 324, as viewed from the right atrium. For some applications, the location is (a) at posteroseptal commissure 217, (b) at anteroposterior commissure 324, or (c) along posterior leaflet 284; in other words, the location is (a) at or counterclockwise to posteroseptal commissure 217, and (b) at or clockwise to anteroposterior commissure 324, as viewed from the right atrium. For example, the location may be at:

a circumferential middle 219 of posterior leaflet 284 of a tricuspid valve 207, as shown in FIG. 5A, posteroseptal commissure 217 (configuration not shown), or anteroposterior commissure 324 (configuration not shown).

The direction of the 1 cm from the described anatomical sites may be either circumferentially around the annulus, up the wall of right atrium 200 above annulus 283, or a combination of circumferentially around the annulus and up the wall of the atrium.

Alternatively, for some applications, first tissue anchor 204 is implanted at a ventricular site below the level of the valve, typically up to 3 cm below the level of the valve. In this case, tether 22 may pass through tricuspid valve 207, such as through a commissure of the valve.

After first tissue anchor 204 has been implanted at first atrial site 292, the implantation tool is removed from the subject's body, typically leaving catheter 206 in situ.

Figure 5B:
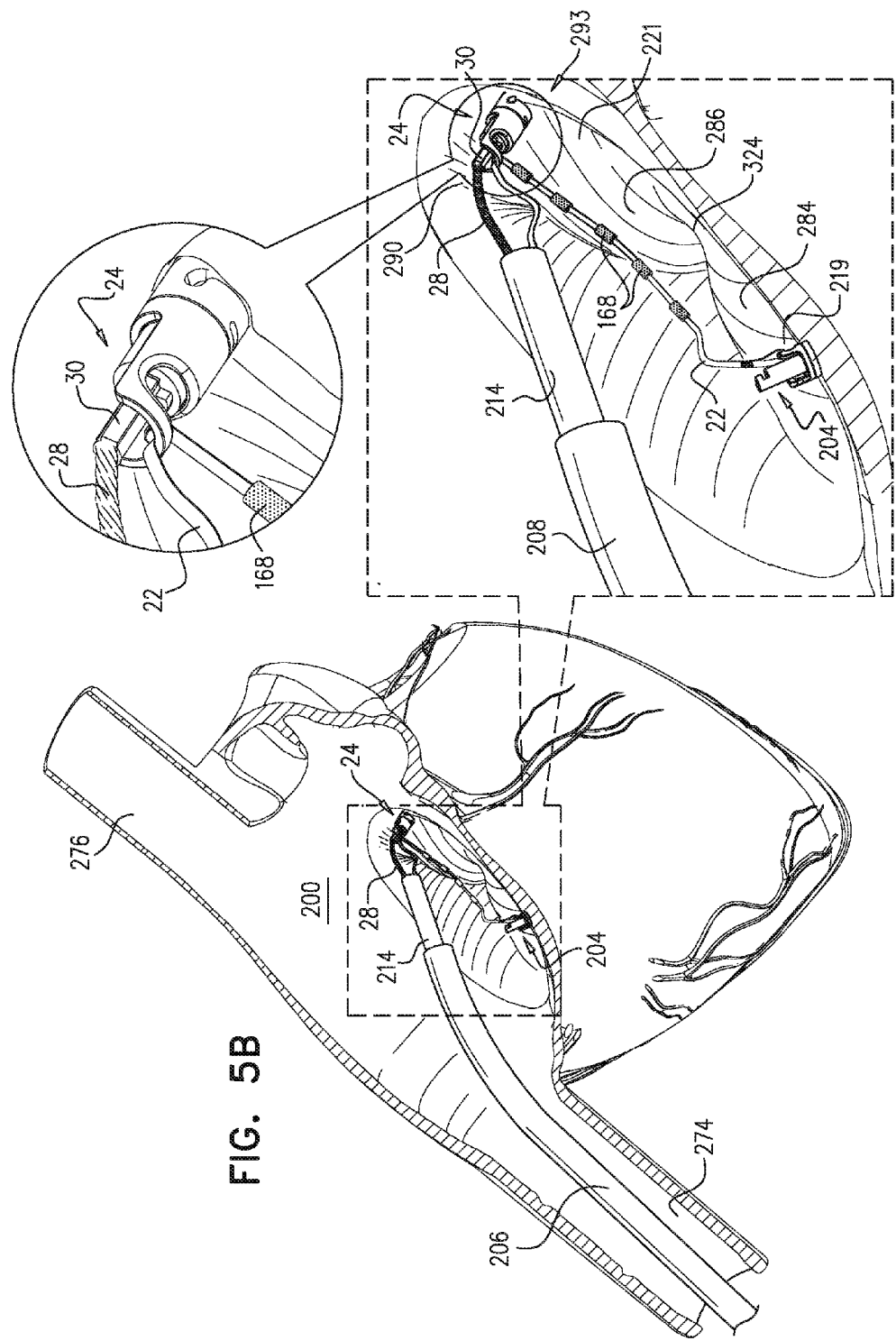

Outside the subject's body, the physician threads a free end 213 of tether 22 through lateral opening 82 of outer tether-securing element 80 of second tissue anchor 24, and then through a lumen of a delivery tube 214 of tissue-anchor system 10 (shown in FIG. 5B). Tether 22 thus connects first and second tissue anchors 204 and 24. Valve-tensioning implant system 202 enables this remote coupling of the anchors to one another via catheter 206.

As shown in FIG. 5B, second tissue anchor 24 is implanted at a second atrial site 293 using torque-delivery cable 28 of torque-delivery tool 20. Tissue-anchor system 10, including second tissue anchor 24 and torque-delivery cable 28, is introduced over tether 22 and through delivery tube 214, which itself is advanced through catheter 206. Tissue-anchor system 10 is introduced in the unlocked state (tether-locking mechanism 68 is also in the unlocked state), as described hereinabove with reference to FIGS. 1A-F. Second atrial site 293 is selected from the group of sites consisting of: annulus 283, and a wall of right atrium 200 above annulus 283. For some applications, second atrial site 293 is located within 1 cm of a site on annulus 283 that circumferentially corresponds to a location that is (a) at or clockwise to a point on the annulus 1 cm septal (i.e., counterclockwise) to a septoanterior commissure (SAC) 290, and (b) at or counterclockwise to a point on the annulus 1 cm posterior (i.e., clockwise) to anteroposterior commissure (APC) 324, as viewed from the right atrium. For some applications, the location is (a) at septoanterior commissure (SAC) 290, (b) at anteroposterior commissure (APC) 324, or (c) along anterior leaflet 286; in other words, the location is (a) at or clockwise to septoanterior commissure (SAC) 290, and (b) at or counterclockwise to anteroposterior commissure (APC) 324, as viewed from the right atrium. For example, the location may be at:

a circumferential middle 221 of anterior leaflet 286 shown in FIG. 5B, septoanterior commissure 290 (configuration not shown), or anteroposterior commissure 324 (configuration not shown).

The direction of the 1 cm from the described anatomical sites may be either circumferentially around the annulus, up the wall of right atrium 200 above annulus 283, or a combination of circumferentially around the annulus and up the wall of the atrium.

The locations of first and second atrial sites 292 and 293 may be inverted, such as when an approach from superior vena cava 276 is used.

Second tissue anchor 24 is implanted at second atrial site 293 by rotating torque-delivery cable 28 (including distal torque-delivery head 30).

The size of the tricuspid valve orifice is reduced by tensioning tether 22, so as to reduce regurgitation. Such tensioning may be performed by proximally pulling on free end 213 tether 22, such that a portion of tether 22 is pulled through lateral opening 82 of outer tether-securing element 80 of second tissue anchor 24. Tissue-anchor system 10 enables this tension to be applied remotely, i.e., via catheter 206.

Figure 5C:
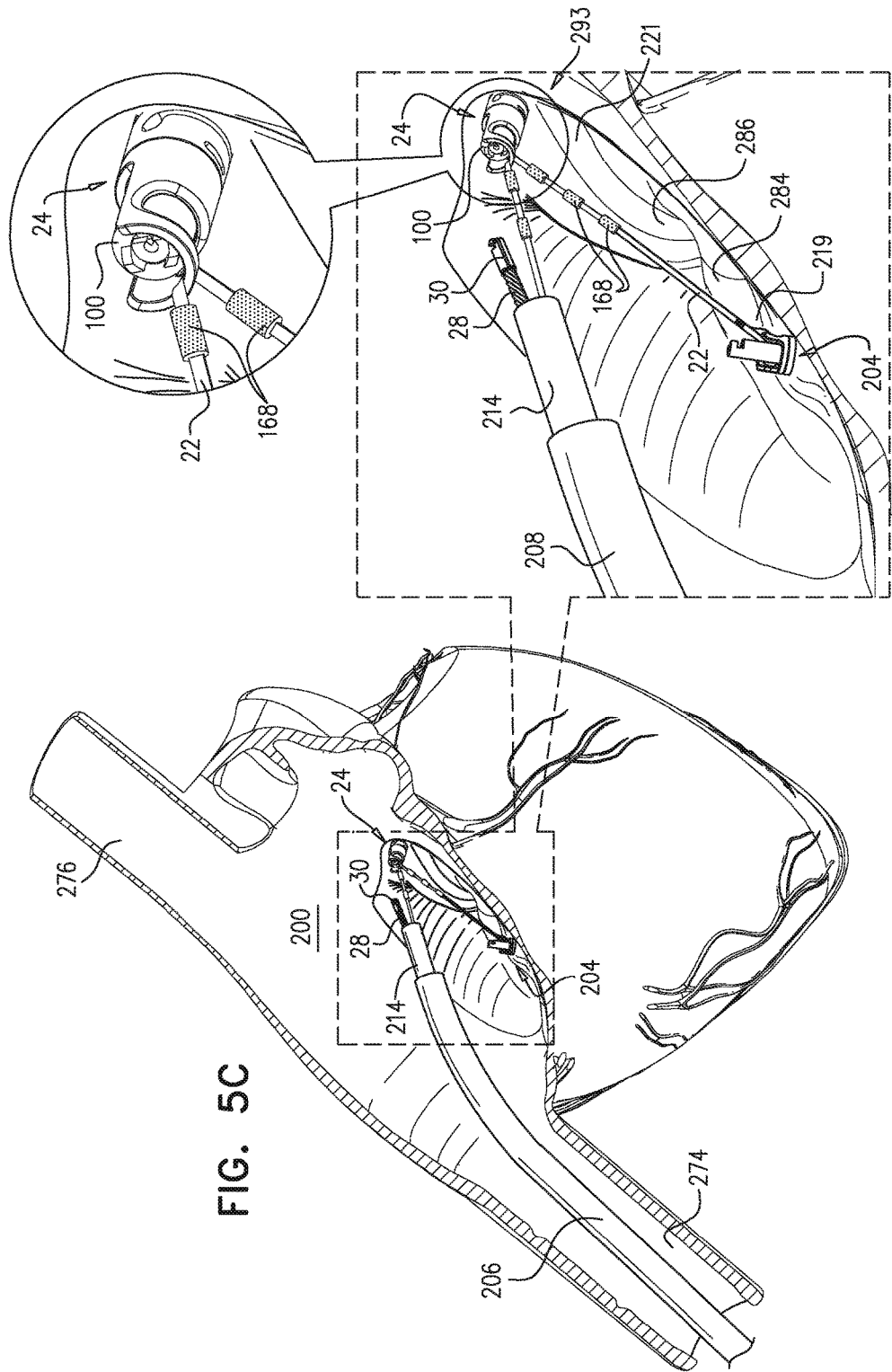

As shown in FIG. 5C, once the tension has been applied, torque-delivery cable 28 (including distal torque-delivery head 30) is decoupled from axially-stationary shaft 56 of second tissue anchor 24, such as by removing locking wire 110. As a result, spring 70 expands and presses tether 22 against outer tether-securing element 80. This pressing transitions tissue-anchor system 10 to the locked state (and tether-locking mechanism 68 to the locked state), by locking tether 22 with respect to tissue anchor 24. Such locking maintains the distance and tension between second tissue anchor 24 and first tissue anchor 204.

Figure 5D:
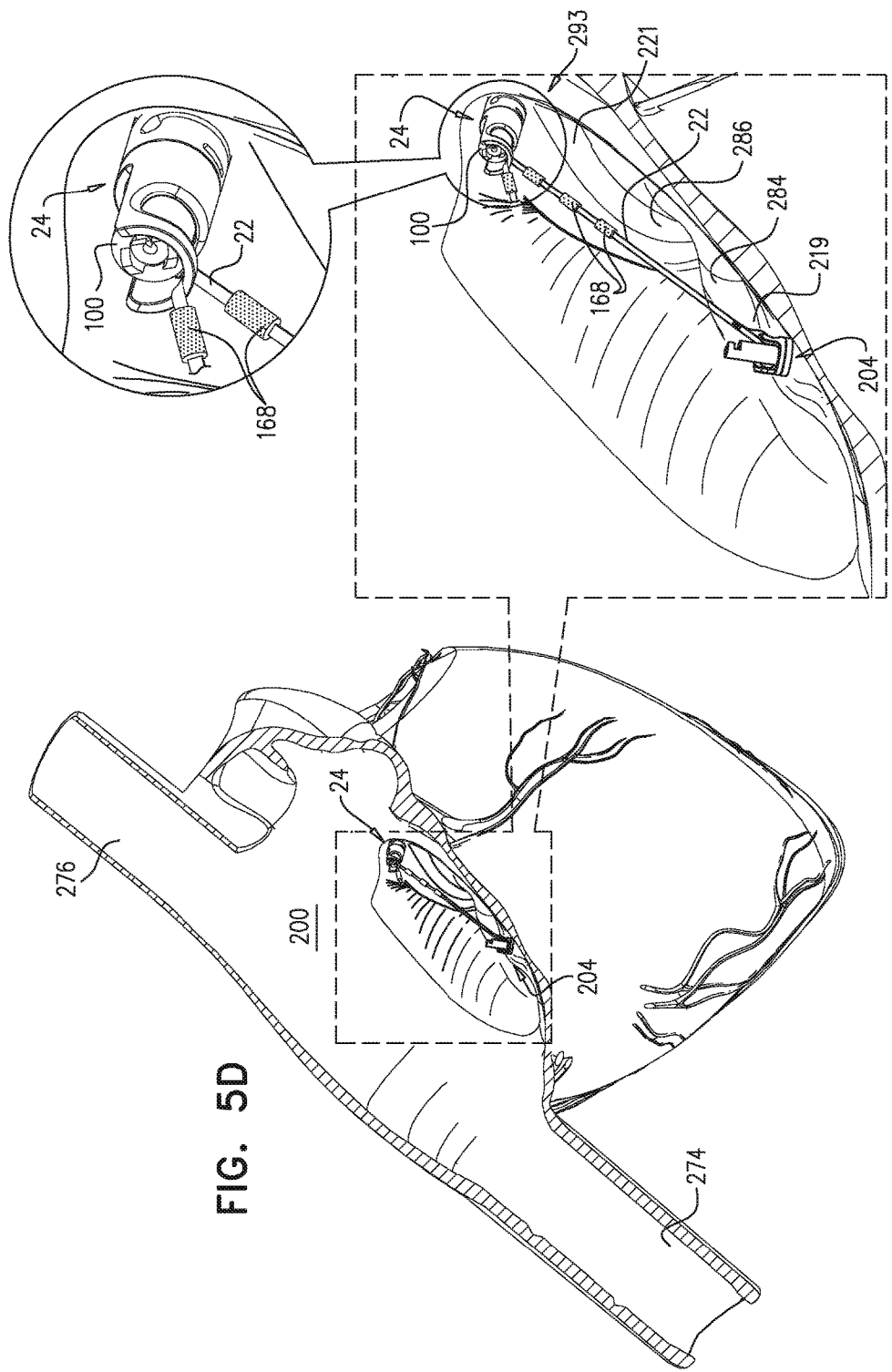

As shown in FIG. 5D, after tether 22 has been tensioned, an excess portion 294 of tether 22 remains free in right atrium 200. It is generally undesirable to leave this excess portion free to move around in the atrium. For some applications, excess portion 294 of tether 22 is cut and removed from the atrium, using a cutting tool 498, such as thoracoscopic scissors, as known in the art. Alternatively, the excess portion is cut using cutting tool 600, described hereinbelow with reference to FIGS. 11A-D. Further alternatively, for some applications, excess portion 294 is secured in a desired disposition in the vasculature of right atrium 200, such as in inferior vena cava 274, superior vena cava 276, or a coronary sinus.

Valve-tensioning implant system 202 allows first and second anchors 204 and 24 to be delivered separately and connected afterwards in situ. This simplifies the procedure for the operator, and allows an approach from two or more different blood vessels such as transfemoral, transjugular, transradial or transapical approaches, which may provide simpler access to the anchoring point.

Although valve-tensioning implant system 202 and tissue-anchor system 10 have been described hereinabove as being used to remodel the tricuspid valve, they may also be used to remodel the mitral valve, unions mutandis, such as using multiple tissue-anchor system 400, described hereinbelow with reference to FIG. 8 (for example, with a plurality of tissue anchors implanted along the posterior annulus).

Reference is now made to FIGS. 6A-E, which are schematic illustrations of a tricuspid-mitral valve repair procedure, in accordance with an application of the present invention. In this procedure, both the tricuspid and the mitral valves are repaired by simultaneously applying tension across both valves using a tether that passes through the atrial septum.

For some applications, the procedure is performed using valve-tensioning implant system 202, described hereinabove with reference to FIGS. 5A-D. Alternatively, other tissue-anchoring and/or tether tensioning techniques may be used. For applications in which valve-tensioning implant system 202 is used, tissue anchor 24 serves as a second tissue anchor 24, and valve-tensioning implant system 202 further comprises first tissue anchor 204, as described hereinabove with reference to FIGS. 5A-D. Alternatively, tissue anchor 724, described hereinbelow with reference to FIGS. 12A-14B, or another tissue anchor, may be used as the first tissue anchor. Valve-tensioning implant system 202 is typically introduced transcatheterly and endovascularly (typically percutaneously), via catheter 206, with the aid of a guidewire, through vasculature of the subject, such as (a) via the femoral vein, through the inferior vena cava, and into right atrium 200, (b) via the basilic vein, through the subclavian vein through the superior vena cava, and into right atrium 200, or (c) via the external jugular vein, through the subclavian vein through the superior vena cava, and into right atrium 200. The procedure is typically performed with the aid of imaging, such as fluoroscopy, transesophageal, transthoracic echocardiography, ICE, and/or echocardiography. The procedure may be performed using techniques described in above-mentioned US Patent Application Publication 2012/0035712, with reference to FIGS. 1A-D thereof, mutatis mutandis.

Figure 7:
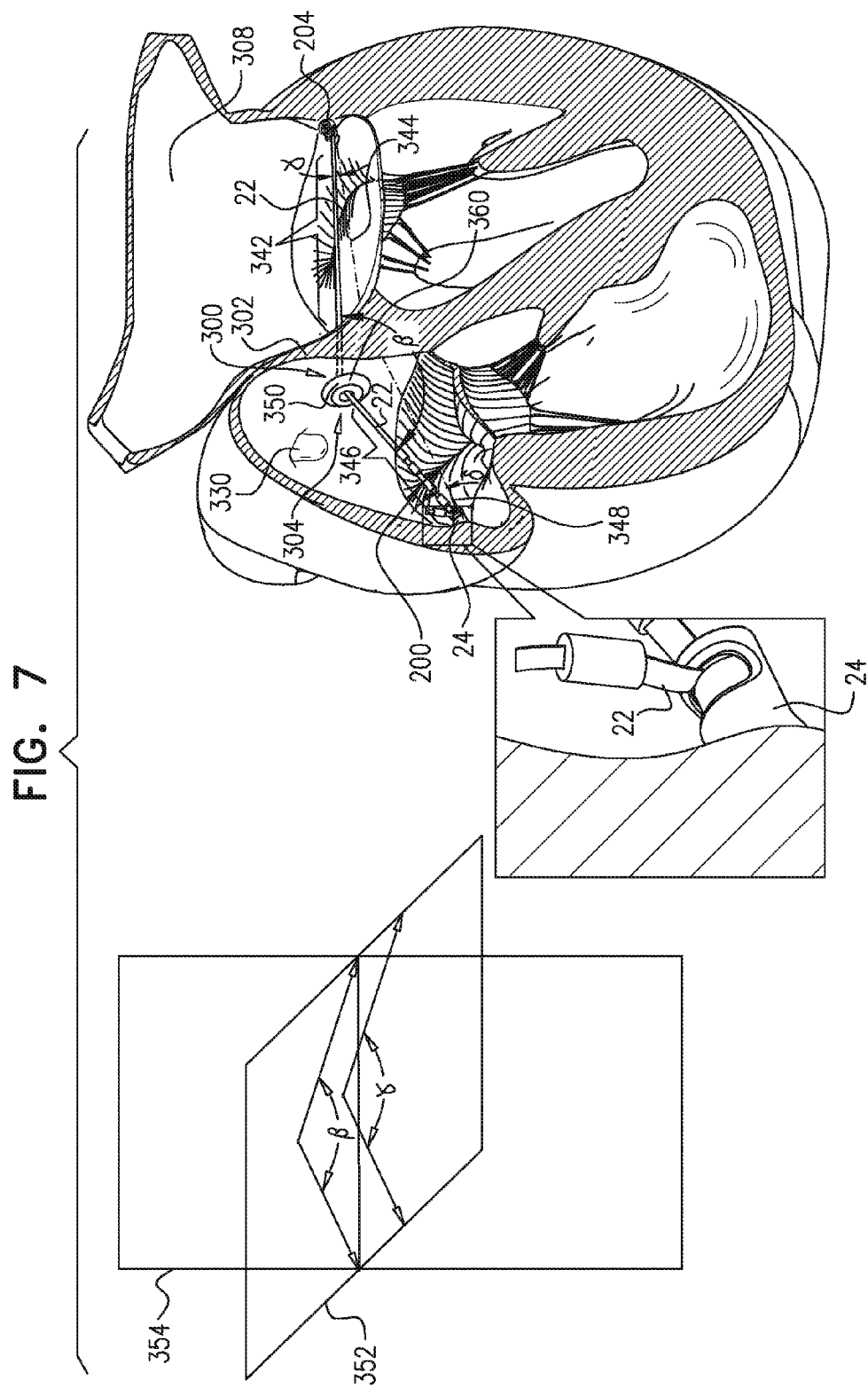
FIG. 7 is a schematic illustration of a heart upon conclusion of the tricuspid-mitral valve repair procedure of FIGS. 6A-E, in accordance with an application of the present invention.

After catheter 206 has been introduced into right atrium 200, an opening 300 is made through an atrial septum 302 at a septal site 304, which is typically at least 5 mm from the fossa ovalis, such as at least 10 mm from the fossa ovalis (shown in FIG. 7).

As shown in FIG. 6A, first tissue anchor 204 is endovascularly advanced to a left-atrial site 306 of a left atrium 308, the site selected from the group of sites consisting of: a mitral annular site 307 on an annulus of a mitral valve 310, and a wall of left atrium 308 above the mitral annular site. Typically, in order to advance first tissue anchor 204 into left atrium 308, catheter 206 is advanced through opening 300. An inner tube 305 may be advanced through catheter 206, and a delivery tool may be advanced through inner tube 305.

As shown in FIG. 69, first tissue anchor 204 is implanted at left-atrial site 306. For some applications, mitral annular site 307 circumferentially corresponds to a posterior leaflet 312 of the mitral valve. For example, mitral annular site 307 may circumferentially correspond to an annular site of the mitral valve within 1 cm of a lateral scallop (P1) 313 and/or within 1 cm of a middle scallop (P2) 314 of posterior leaflet 312. Alternatively, first tissue anchor 204 is implanted at any site on the lateral wall of the left side of the heart, atrium, annulus, papillary or any other structure of the left side of the heart or valve that can be used as an anchoring site to move the left lateral wall of the heart septally.

Inner tube 305, if used, is removed from catheter 206, and catheter 206 is withdrawn to right atrium 200. Outside of the subject's body, the physician threads free end 213 of tether 22 through lateral opening 82 of outer tether-securing element 80 of second tissue anchor 24, and then through a lumen of a delivery tube 214 of tissue-anchor system 10 (shown in FIG. 5B), as described hereinabove. Tether 22 thus connects first and second tissue anchors 204 and 24. Valve-tensioning implant system 202 enables this remote coupling of the anchors to one another via catheter 206.

As shown in FIG. 6C, tissue-anchor system 10, including second tissue anchor 24 and torque-delivery cable 28, is endovascularly introduced over tether 22 and through delivery tube 214, which itself is advanced through catheter 206. Tissue-anchor system 10 is introduced in the unlocked state (tether-locking mechanism 68 is also in the unlocked state), as described hereinabove with reference to FIGS. 1A-F. The distal end of delivery tube 214, and second tissue anchor 24, are steered to a right-atrial site 320 of right atrium 200 selected from the group of sites consisting of: a tricuspid annular site 322 on an annulus of tricuspid valve 207, and a wall of right atrium 200 above tricuspid annular site 322. For some applications, tricuspid annular site 322 circumferentially corresponds to an annular site of the tricuspid valve that is (a) at or clockwise to a point on the tricuspid annulus 2 cm anterior (i.e., counterclockwise) to anteroposterior commissure (APC) 324 of tricuspid valve 207, and (b) at or 1 cm counterclockwise to posteroseptal commissure 217 of tricuspid valve 207, as viewed from the right atrium. Alternatively, the annular site is (a) at or clockwise to septoanterior commissure (SAC) 290, and (b) at or counterclockwise to posteroseptal commissure 217. Alternatively, second tissue anchor 24 is implanted at any site on the lateral wall of the right side of the heart, atrium, annulus, papillary or any other structure of the right side of the heart or valve that can be used as an anchoring site to move the right lateral wall of the heart septally.

As shown in FIG. 6D, second tissue anchor 24 is implanted at tricuspid annular site 322 by rotating torque-delivery cable 28 (including distal torque-delivery head 30).

The size of the tricuspid valve orifice and the size of the mitral valve orifice are reduced by approximating left-atrial site 306 and right-atrial site 320 by tensioning tether 22, so as to reduce regurgitation. Such tensioning may be performed by proximally pulling on free end 213 of tether 22, such that a portion of tether 22 is pulled through lateral opening 82 of outer tether-securing element 80 of second tissue anchor 24, as indicated by the arrow in FIG. 6D. Tissue-anchor system 10 enables this tension to be applied remotely, i.e., via catheter 206.

As shown in FIG. 6E, once the tension has been applied, torque-delivery cable 28 (including distal torque-delivery head 30) is decoupled from axially-stationary shaft 56 of second tissue anchor 24, such as by removing locking wire 110. As a result, spring 70 expands and press tether 22 against outer tether-securing element 80. This pressing transitions tissue-anchor system 10 to the locked state (and tether-locking mechanism 68 to the locked state), by locking tether 22 with respect to second tissue anchor 24. Such locking maintains the distance and tension between second tissue anchor 24 and first tissue anchor 204.

As described hereinabove with reference to FIG. 5D, after tether 22 has been tensioned, an excess portion 294 of tether 22 remains free in right atrium 200. It is generally undesirable to leave this excess portion free to move around in the atrium. For some applications, excess portion 294 of tether 22 is cut and removed from the atrium, using a cutting tool 498, such as thoracoscopic scissors, as known in the art. Alternatively, the excess portion is cut using cutting tool 600, described hereinbelow with reference to FIGS. 11A-D. Further alternatively, for some applications, excess portion is secured in a desired disposition in the vasculature of right atrium 200, such as in inferior vena cava 274, superior vena cava 276, or a coronary sinus.

For some applications, as described above with reference to FIGS. 6A-E, second tissue anchor 24 is endovascularly advanced to right-atrial site 320 after first tissue anchor 204 has been implanted. Alternatively, for some applications, first tissue anchor 204 is endovascularly advanced to left-atrial site 306 after second tissue anchor 24 has been implanted. For example, a multiple-anchor delivery tool may be used with tether 22 pre-threaded through second tissue anchor 24.

Reference is made to FIG. 7, which is a schematic illustration of a heart upon conclusion of the tricuspid-mitral valve repair procedure of FIGS. 6A-E (after implantation of tether 22 across both atria), in accordance with an application of the present invention. As can be seen, tether 22 passes through opening 300 through atrial septum 302 at septal site 304. Typically, septal site 304 is typically at least 5 mm from a fossa ovalis 330, such as at least 10 mm from fossa ovalis 330. Typically, septal site 304 is anterior to, and/or apical to, and/or toward the aorta from, fossa ovalis 330 as shown in FIG. 7, such as near or at the septum secundum and/or septum primum. As used in the present application, including in the claims, "apical to" means "in a direction towards the apex of the heart."

Typically, septal site 304 is at least 3 mm, no more than 20 mm, and/or between 3 and 20 mm (e.g., 10 mm) superior and anterior to a coronary sinus orifice, and/or at least 3 mm, no more than 15 mm, and/or between 3 and 15 mm (e.g., 5 mm) posterior to an aorta.

Reference is made to FIGS. 6E and 7. The location of opening 300 is selected such that, after the tissue anchors are implanted and tether 22 has been tensioned, an angle of tether 22 at opening 300 of atrial septum 302 is ideally as close as possible to 180 degrees. In practice, the angle should be at least 120 degrees to avoid excessive force on the atrial septum, such as at least 135 degrees, or at least 150 degrees, and/or less than 180 degrees (in other words, the tether is not straight as it passes through opening 300), such as less than 170 degrees, e.g., no more than 150 degrees, such as between 140 and 150 degrees. Thus, the location of opening 300 should not be too superior and posterior on atrial septum 302, for example, should not be at fossa ovalis 330. A vertex 350 of the angle of tether 22 at opening 300 typically points at least partially in a posterior direction (as can be seen in FIG. 6E), at least partially in a superior direction, and/or in at least partially an away-from-apical direction (as can be seen in FIG. 7).

For some applications, if tensioned tether 22 were to be projected onto a transverse plane 352 of the heart (as shown schematically in FIG. 7), the angle as projected (labeled α (alpha) in FIGS. 6E and 7), would be at least 120 degrees, such as at least 135 degrees, or at least 140 degrees. Ideally, the angle as projected is as close as possible to 180 degrees, but in practice the angle as projected is typically less than 180 degrees (i.e., tether 22 is not straight), such as no more than 170 degrees, generally between 140 and 150 degrees.

For some applications, if tensioned tether 22 were to be projected onto a coronal plane 354 of the heart (as shown schematically in FIG. 7), the angle as projected (labeled β (beta) in FIG. 7), would be at least 120 degrees, such as at least 135 degrees, e.g., at least 140 degrees. Ideally, the angle as projected is as close as possible to 180 degrees, but in practice the angle as projected is typically less 180 degrees (i.e., tether 22 is not straight), such as no more than 170 degrees, generally between 150 and 170 degrees.

For some applications, as shown in FIG. 7, (a) a portion 342 of tensioned tether 22 in left atrium 308 between opening 300 of atrial septum 302 (apex 340) and first tissue anchor 204 and (b) a plane 344 defined by the annulus of mitral valve 310, form an angle γ (gamma) of less than 30 degrees. Similarly, for some applications, as shown in FIG. 7, (a) a portion 346 of tensioned tether 22 in right atrium 200 between opening 300 of atrial septum 302 (apex 340) and second tissue anchor 24 and (b) a plane 348 defined by the annulus of tricuspid valve 207, form an angle δ (delta) of less than 30 degrees.

For some applications, the procedure described with reference to FIGS. 6A-E further comprises placing, in opening 300 of atrial septum 302, an annular reinforcement element 360 that is shaped so as to define an opening therethrough. Reinforcement element 360 is typically delivered and placed after implanting first tissue anchor 204, and before implanting second tissue anchor 24. For example, reinforcement element 360 may be delivered using a balloon-expandable device, or reinforcement element 360 may be self-expanding. Tether 22 passes through the opening of reinforcement element 360. Reinforcement element 360 is typically annular.

Reinforcement element 360 distributes the force of tether 22 against opening 300 of atrial septum 302, which may prevent damage to the atrial septum, such as caused by cutting by the tether. For some applications, reinforcement element 360 is stiffer in one direction, and is placed in opening 300 of atrial septum 302 with the stiffer direction facing away from vertex 350, i.e., in the direction in which tether 22 applies the greatest force to opening 300 of atrial septum 302. Reinforcement element 360 may optionally also be configured to close opening 300 of atrial septum 302, and/or to reduce a size of opening 300 upon withdrawal of catheter 206 from the opening. For example, a radially inner surface of reinforcement element 360 may comprise a material configured to promote tissue growth.

For some applications, annular reinforcement element 360 comprises a locking mechanism, which is configured to inhibit sliding of tether 22 through annular reinforcement element 360 when in a locked state. The locking mechanism is transitioned from an unlocked state to the locked state after tether 22 has been tensioned, as described above. This locking has the effect of fixing the respective distances between opening 300 of atrial septum 302 and the first and the second tissue anchors, and preventing dilation of the annulus of one of the atrioventricular valves and the corresponding reduction in size of the other atrioventricular valve. Typically, at least 75% of the load in tether 22 is borne by the first and the second tissue anchors, and no more than 25% of the load is borne by locked annular reinforcement element 360, thereby reducing the likelihood that annular reinforcement element 360 might tear or otherwise damage atrial septum 302.

Although this tricuspid-mitral valve repair procedure has been described with reference to FIGS. 6A-B as being performed using valve-tensioning implant system 202, alternatively other tissue-anchoring and/or tether tensioning techniques may be used. For example, tissue anchors and/or tensioning techniques may be used that are described in one or more of the patent applications listed and incorporated by reference hereinbelow.

Figure 8:
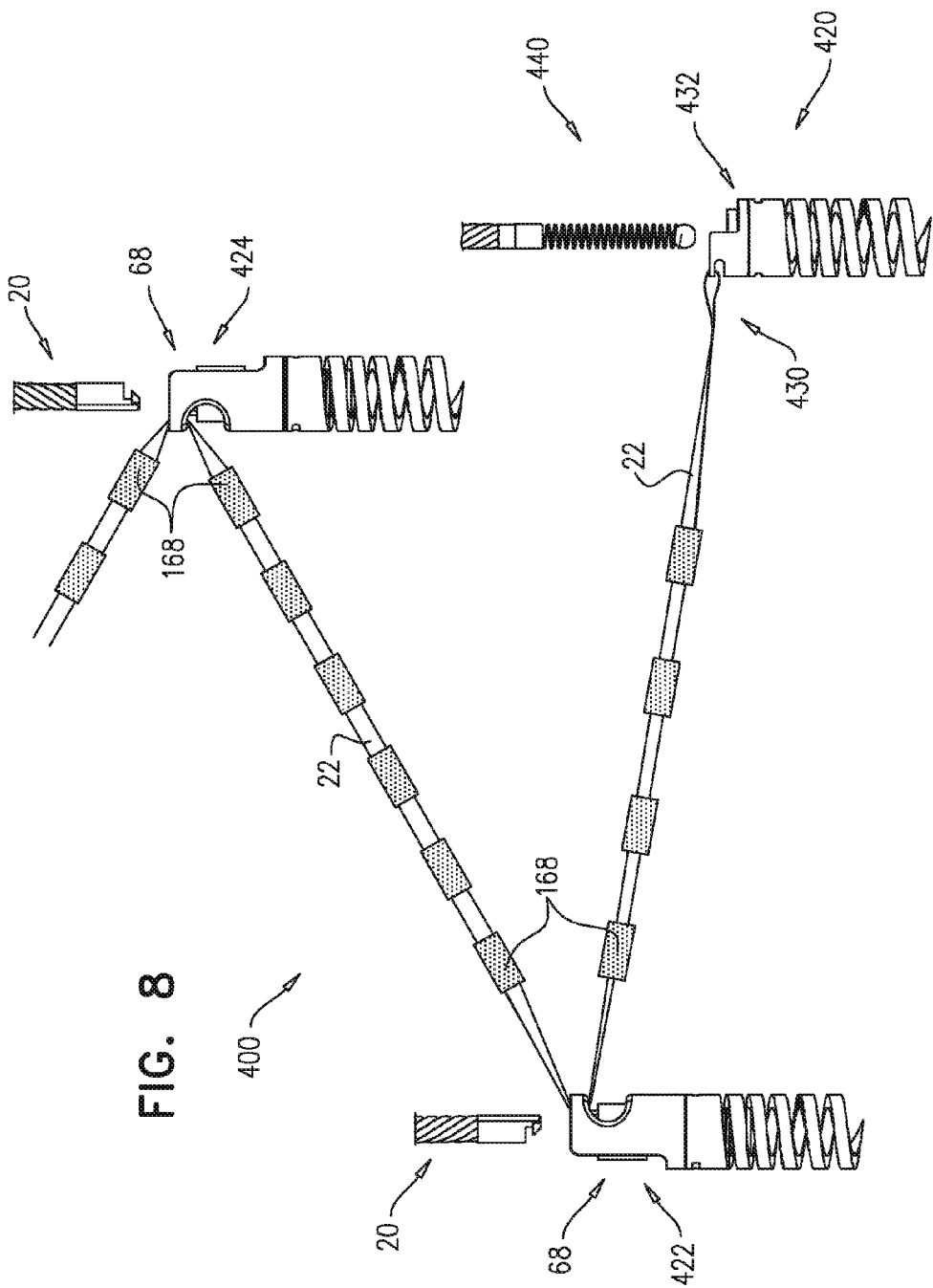
FIG. 8 is a schematic illustration of a multiple tissue-anchor system, in accordance with an application of the present invention.

Reference is now made to FIG. 8, which is a schematic illustration of a multiple tissue-anchor system 400, in accordance with an application of the present invention. Multiple tissue-anchor system 400 comprises three or more tissue anchors, which are coupled together by tether 22 and cinched together in situ. For example, such as shown in FIG. 8, multiple tissue-anchor system 400 may comprise first, second, and third tissue anchors 420, 422, and 424, arranged such that second tissue anchor 422 is positioned along tether 22 between first and third tissue anchors 420 and 424.

For some applications, an end portion 430 of tether 22 is fixed to a head 432 of first tissue anchor 420, and first tissue anchor 420 does not comprise tether-locking mechanism 68, described hereinabove with reference to FIGS. 1A-F, 2A-B, and 3A-E. First tissue anchor 420 may, for example, implement any of the features of (a) tissue anchor 204, described hereinabove with reference to FIG. 5A-D (configuration not shown in FIG. 8), or (b) tissue anchor 724, described hereinbelow with reference to FIGS. 12A-14B (configuration shown in FIG. 8). Second tissue anchor 422 comprises a tissue anchor 24 (including tether-locking mechanism 68), described hereinabove with reference to FIGS. 1A-F, 2A-B, and 3A-E, and/or third tissue anchor 424 comprises a tissue anchor 24 (including tether-locking mechanism 68), described hereinabove with reference to FIGS. 1A-F, 2A-B, and 3A-E.

Typically, each of the tissue anchors is delivered using a separate, respective delivery tool. The tissue anchor(s) that comprise tether-locking mechanism 68 may be delivered using torque-delivery tool 20, described hereinabove with reference to FIGS. 1A-F, 2A-B, and 5B-C, and the tissue anchor(s) that do not comprise tether-locking mechanism 68 may be delivered using a tool 440, which implements the features of the tool described hereinabove with reference to FIG. 5A.

Figure 9:
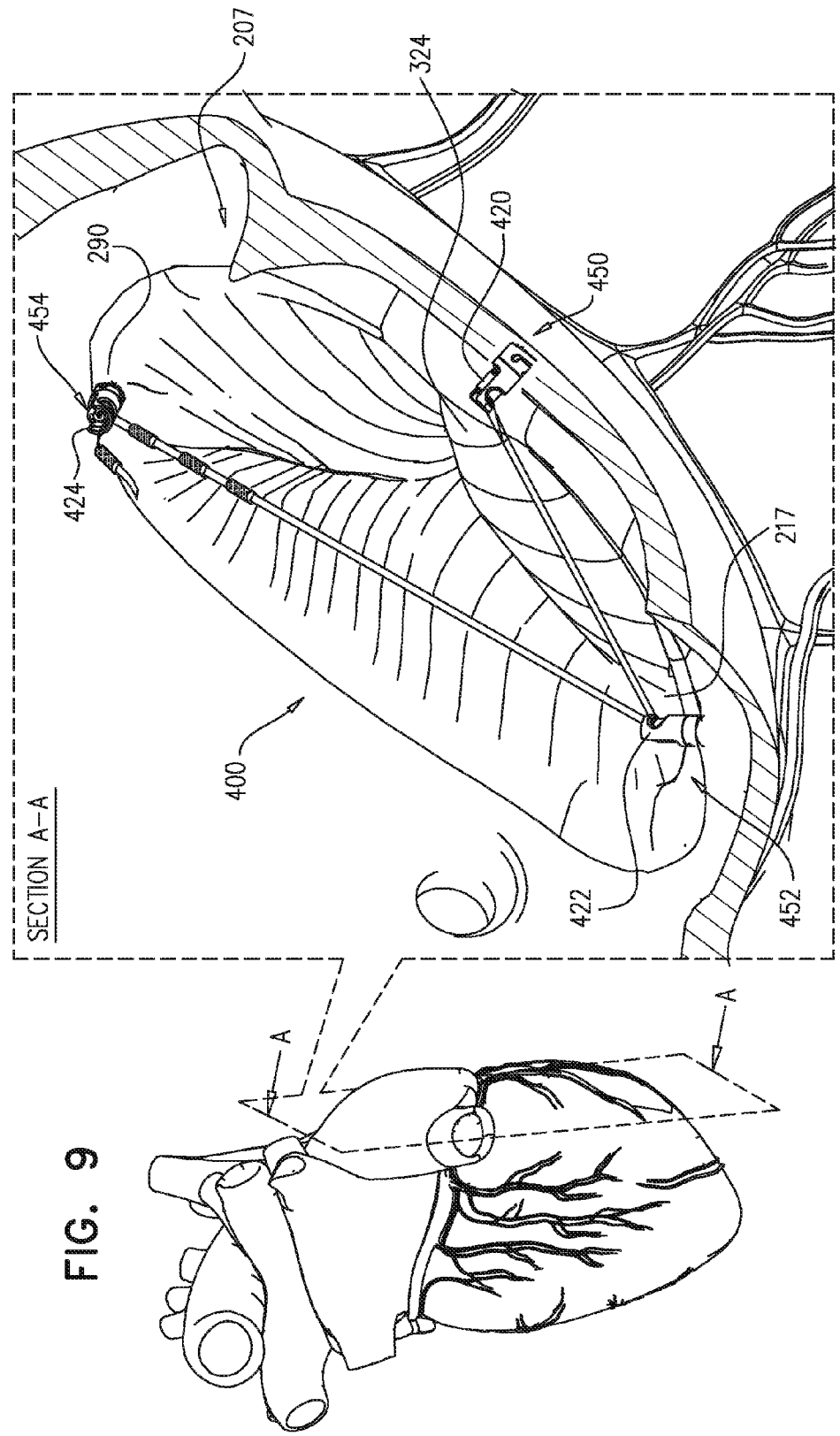
FIG. 9 is a schematic illustration of the multiple tissue-anchor system of FIG. 8 applied to a tricuspid valve, in accordance with an application of the present invention.

Reference is now made to FIG. 9, which is a schematic illustration of multiple tissue-anchor system 400 applied to tricuspid valve 207, in accordance with an application of the present invention. In this exemplary deployment, first tissue anchor 420 is first implanted at a first atial site 450, such as anteroposterior commissure (APC) 324, or any of the other right-atrial sites described herein above.

Thereafter, second tissue anchor 422 is implanted at a second atrial site 452, such as posteroseptal commissure 217 or any of the other right-atrial sites described hereinabove. Tether 22 is tensioned between first and second tissue anchors 420 and 422, thereby pulling APC 324 and posteroseptal commissure 217 toward one another, resulting in at least partial bicuspidization. Tether-locking mechanism 68 of second tissue anchor 422 is locked, as described hereinabove. Optionally, tether 22 comprises another set of friction-enhancing features along the portion of the tether than passes through the head of second tissue anchor 422 (not shown in FIG. 9, but shown in FIG. 8).

Thereafter, third tissue anchor 424 is implanted at a third atrial site 454, such as septoanterior commissure (SAC) 290, or any of the other right-atrial sites described hereinabove. Tether 22 is tensioned between second and third tissue anchors 422 and 424, thereby pulling SAC 290 and posteroseptal commissure 217 (and APC 324 to some extent) toward one another. Tether-locking mechanism 68 of third tissue anchor 424 is locked, as described hereinabove. Excess tether 22 is cut or secured, such as described above.

This tensioning between APC 324 and posteroseptal commissure 217, and between SAC 290 and posteroseptal commissure 217, results in a substantial reduction in tricuspid valve circumference and diameter.

Alternatively, second tissue anchor 422 does not comprise tether-locking mechanism 68, and tension is applied between APC 324 and posteroseptal commissure 217, and between SAC 290 and posteroseptal commissure 217, after third tissue anchor 424 has been implanted, and then tether-locking mechanism 68 of third tissue anchor 424 is locked.

It is noted that the physician may decide during the procedure not to implant third tissue anchor 424, such as if a sufficient reduction in regurgitation is achieved using only the first two anchors. Not implanting third tissue anchor 424 is possible because the tissue anchors are threaded over tether 22 one at a time during the procedure.

In some applications of the present invention, valve-tensioning implant system 202, described hereinabove with reference to FIGS. 5A-D, 6A-E, and 7, is used to remodel a pathologically dilated ventricular chamber, or to reduce future ventricular dilation, by applying tension between first and second tissue anchors 204 and 24 implanted in a left or right ventricle, such as in a papillary muscle or wall of the ventricle. This technique may improve ventricular pumping efficiency and/or reduce tricuspid or mitral regurgitation. When used in the right ventricle, this technique might be considered as creating a second artificial moderator band.

Figure 10B:
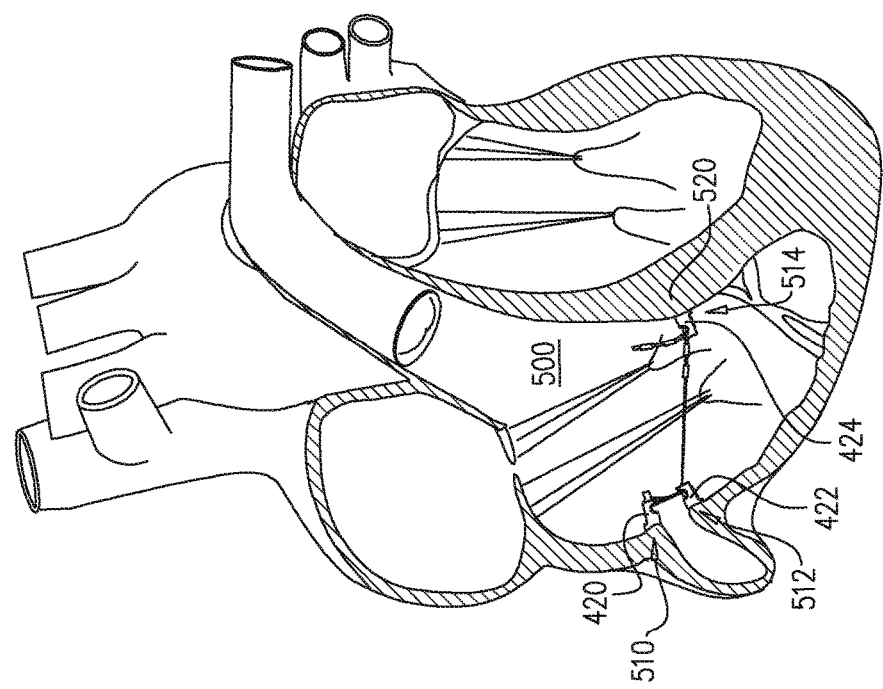
FIGS. 10A-B are schematic illustrations of the multiple tissue-anchor system of FIG. 8 applied to a right ventricle, in accordance with an application of the present invention.
Figure 10A:
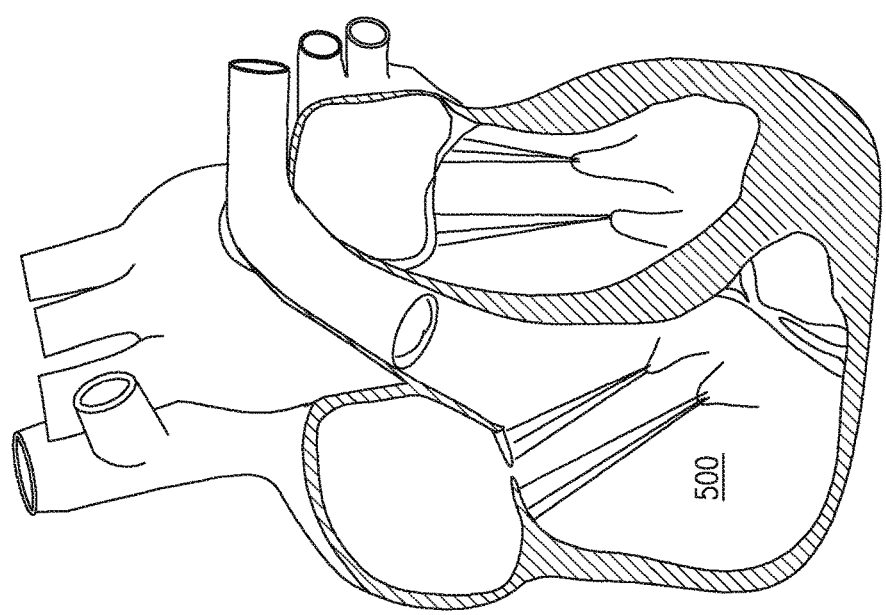

Reference is made to FIGS. 10A-B, which are schematic illustrations of multiple tissue-anchor system 400 applied to a right ventricle 500, in accordance with an application of the present invention. In this application, multiple tissue-anchor system 400 is used to treat dilated right ventricle 500, as shown in FIG. 10A. First tissue anchor 420 is first endovascularly (e.g., percutaneously) advanced to and implanted, from within right ventricle 500, at a first ventricular wall site 510, typically on a posterior or an anterior wall below the level of the papillary muscles. Thereafter, second tissue anchor 422 is endovascularly (e.g., percutaneously) advanced to and implanted, from within right ventricle 500, at a second ventricular wall site 512, typically on the anterior wall above the level of or at the junction of the natural moderator band and the anterior wall, typically no more than 2.5 cm from first ventricular wall site 510, depending on the extent of dilation of the ventricle. Tether 22 is tensioned between first and second tissue anchors 420 and 422, thereby approximating first and second ventricular wall sites 510 and 512, and plicating the wall. Tether-locking mechanism 68 of second tissue anchor 422 is locked, as described hereinabove. Thereafter, third tissue anchor 424 is endovascularly (e.g., percutaneously) advanced to and implanted, from within right ventricle 500, at a third ventricular wall site 514 on an interventricular septum 520, typically between the right ventricular outflow tract (RVOT) and a junction of the natural moderator band and an interventricular septal wall. Tether 22 is tensioned between second and third tissue anchors 422 and 424, thereby approximating (a) plicated (approximated) first and second ventricular wall sites 510 and 512, collectively, and (b) third ventricular wall site 514. Tether-locking mechanism 68 of third tissue anchor 424 is locked, as described hereinabove. Excess tether 22 is cut or secured, such as described above. As a result of this tensioning, tether 22 functions as an artificial moderator band, reducing ventricular dilation, such as by resisting movement of the anterior wall as the ventricle fills during diastole.

Alternatively, second tissue anchor 422 does not comprise tether-locking mechanism 68, and tension is applied between first and second ventricular wall site 510 and 512, and between these sites and third ventricular wall site 514, after third tissue anchor 424 has been implanted, and then tether-locking mechanism 68 of third tissue anchor 424 is locked.

For some applications, tether 22 is electrically conductive, in order to facilitate conduction of natural cardiac electrical signals from the wall of interventricular septum 520 to the anterior wall of right ventricle 500, mimicking one of the natural functions of the natural moderator band. Alternatively or additionally, for some applications, tether 22 is elastic, in order to facilitate diastolic relaxation of the right ventricle. For example, tether 22 may be sufficiently elastic to lengthen by at least 10%, no more than 100%, and/or between 10% and 100% under diastolic loading, compared to under systolic loading.

For some applications, the ventricular treatment method described with reference to FIGS. 10A-B is performed using tissue anchors other than those of multiple tissue-anchor system 400. These other tissue anchors do not comprise tether-locking mechanism 68. Typically, these other tissue anchors comprise respective helical tissue-coupling elements, as is known in the art. For some applications, tissue anchors are used that are described in International Application PCT/IL2014/050027, which published as PCT Publication WO 2014/108903, and/or in one or more of the other patent applications incorporated by reference hereinbelow.

Reference is now made to FIGS. 11A-D, which are schematic illustrations of a cutting tool 600, in accordance with an application of the present invention. Cutting tool 600 is configured to cut an elongate member 610, such as tether 22 described above, or any other elongate member, such as a suture; elongate member 610 is typically flexible. Cutting tool 600 is configured to be used in transcatheter procedures. Cutting tool 600 uses torsion to cut elongate member 610, which places no tension on the implant, such as the implanted anchors described hereinabove, and provides a high degree of control of the cutting.

Cutting tool 600 comprises an outer tube 620 and an inner tube 622 that is nested within outer tube 620. Typically, both the inner and the outer tubes are cylindrical. For some applications, outer tube 620 comprises a braided extruded material, such as a metal (such as stainless steel) and nylon, and/or inner tube 622 comprises a metal (such as stainless steel). For some applications, a proximal end of inner tube 622 is fixed (e.g., welded) to a distal end of a torque cable, which typically comprises a metal (such as stainless steel). Inner tube 622 is shaped so as to define an inner-tube distal end (non-lateral) opening 624 through a distal end 626 of inner tube 622. Inner tube 622 is also shaped so as to define an inner-tube lateral opening 628, typically having a distal-most portion 629 that is within 5 mm of distal end 626, such as within 3 mm of the distal end. Typically, inner-tube lateral opening 628 has an area of between 1 and 10 mm2.

Elongate member 610, before being cut, passes through both inner-tube distal end opening 624 and inner-tube lateral opening 628, such as shown in FIGS. 11A-C.

Outer tube 620 is shaped so as to define an outer-tube distal end (non-lateral) opening 630 through a distal end 632 of outer tube 620. Outer tube 620 is also shaped so as to define an outer-tube lateral opening 634, which extends to distal end 632. Typically, a proximal portion 640 of outer-tube lateral opening 634 has a first width W1 that is greater than (e.g., at least 125% of) a second width W2 of a distal portion 642 of outer-tube lateral opening 634, which distal portion 642 extends to distal end 632. First and second widths W1 and W2 are measured circumferentially around outer tube 620. For example, first width W1 may be at least 1.5 mm, no more than 5 mm, and/or between 1.5 and 5 mm, and second width W2 may be at least 0.5 mm, no more than 1.25 mm, and/or between 0.5 and 1.25. Second width W2 is greater than (e.g., at least 125% of) a diameter D of elongate member 610, in order to allow the elongate member to pass through distal portion 642, as described hereinbelow with reference to FIG. 11B.

Typically, proximal portion 640 of outer-tube lateral opening 634 has a first length L1 of at least 0.5 mm, no more than 2 mm, and/or between 0.5 and 2 mm, and distal portion 642 of outer-tube lateral opening 634 has a second length L2 of at least 0.5 mm, no more than 2 mm, and/or between 0.5 and 2 mm. First and second lengths L1 and L2 are measured parallel to a longitudinal axis 648 of outer tube 620.

Proximal portion 640 of outer-tube lateral opening 634 has first and second edges 650A and 650B, which extend axially along outer tube 620. One or both of the edges (typically both) are shaped so as to define a sharp cutting blade.

Outer tube 620 typically has an inner diameter of at least 0.75 mm, no more than 4 mm, and/or between 0.75 and 4 mm, and inner tube 622 typically has an outer diameter that is as least 90%, no more than 99%, and/or between 90% and 99% of the inner diameter of outer tube 620, and/or at least 0.65 mm, no more than 3.95 mm, and/or between 0.65 and 3.95 mm. Outer tube 620 typically has a length of at least 20 cm, no more than 200 cm, and/or between 20 and 200 cm. Inner tube 622 typically has a length of at least 1 cm, no more than 200 cm, and/or between 1 and 200 cm (for applications in which inner tube is fixed to the distal end of a torque cable, as described above, inner tube 622 typically has a length of at least 1 cm, no more than 5 cm, and/or between 1 and 5 cm; for applications in which inner tube 622 is not coupled to a torque cable, and thus extends out of the body, the length is typically at least 20 cm, no more than 200 cm, and/or between 20 and 200 cm.

During use of cutting tool 600, elongate member 610 is threaded through both inner-tube distal end opening 624 and inner-tube lateral opening 628, as shown in FIG. 11A. This threading is performed by passing a free proximal end of the elongate member through the tool, while the free end and the tool are outside the subject's body. A proximal portion of the elongate member extends proximally generally alongside an outer surface of outer tube 620, to outside the subject's body (typically through a catheter through which cutting tool 600 also passes). Distal end 626 of inner tube 622 is distal to distal end 632 of outer tube 620, such that a distal portion of inner tube 622 extends out of outer-tube distal end opening 630, typically by at least 1 mm, no more than 10 mm, and/or between 1 to 10 mm. This relative axial positioning of the inner and outer tubes allows free sliding of elongate member 610 as cutting tool 600 is advanced to a desired cutting location along the elongate member. At least a portion, such as all, of inner-tube lateral opening 628 is disposed distally to distal end 632 of outer tube 620.

As shown in FIG. 11B, inner tube 622 is moved proximally with respect to outer tube 620, either by proximally withdrawing the inner tube and/or by distally advancing the outer tube. Typically, a portion of elongate member 610 passes through distal portion 642 of outer-tube lateral opening 634 during such relative movement. A distal edge 660 of inner-tube lateral opening 628 (which edge is typically dull) presses elongate member 610 against a proximal edge 662 of outer-tube lateral opening 634 (which edge is typically dull), causing a proximal portion of the elongate member to extend radially outward from cutting tool 600, typically at an angle of between 60 and 90 degrees with respect to an outer surface of outer tube 620. (Such a disposition of the elongate member no longer provides free sliding of the elongate member; for this reason the inner tube is initially disposed distal to the outer tube, to allow such free sliding.)

As shown in FIG. 11C, inner tube 622 is rotated with respect to outer tube 620, either by rotating the inner tube and/or by rotating the outer tube. Such rotation pushes elongate member 610 against one of sharp first and second edges 650A and 650B of proximal portion 640 of outer-tube lateral opening 634. Inner and outer tubes 622 and 620 are torqued in opposite rotational directions to apply shear on elongate member 610 with the sharp blade edge, causing the sharp edge to cut elongate member 610, as shown in FIG. 11D. Thus cutting tool 600 performs the cutting with torsional force, rather than axial force.

Reference is now made to FIGS. 12A-14l, which are schematic illustrations of a tissue-anchor system 710, in accordance with an application of the present invention. FIGS. 12A-C show tissue-anchor system 710 in an engaged state, and FIGS. 13A-B and 14A-B show tissue-anchor system 710 in a disengaged state. Tissue-anchor system 710 comprises a torque-delivery tool 720, a tissue anchor 724, and a locking shaft 726, which is typically shaped so as to define a sharp distal tip 727. Locking shaft 726 is similar in many respects to locking wire 110, described hereinabove with reference to FIGS. 1A-2A.

Torque-delivery tool 720 is configured to implant tissue anchor 724 in cardiac tissue, and comprises a torque-delivery cable 728, which comprises a distal torque-delivery head 730, which is fixed to torque-delivery cable 728. Distal torque-delivery head 730 is shaped so as to define a chamber 732, which is shaped so as to define (a) a fenestration 734 through a lateral wall 736 of chamber 732, and (b) proximal and distal chamber end openings 738 and 740. Torque-delivery tool 720 further comprises a coupling element 741, which is (a) not fixed to any elements of tissue-anchor system 710, (b) too large to pass through fenestration 734, (c) too large to pass through distal chamber end opening 740, and, optionally, (d) too large to pass through proximal chamber end opening 738. For some applications, fenestration 734 has a greatest dimension (e.g., a greatest diameter) $D_F$ of at least 0.3 mm, no more than 3 mm, and/or between 0.3 mm and 3 mm, and/or distal chamber end opening 740 has a greatest dimension (e.g., a greatest diameter) $D_{EO}$ of at least 0.25 mm, no more than 2.9 mm, and/or between 0.25 and 2.9 mm.

Tissue anchor 724 comprises:
a helical tissue-coupling element 750, which is shaped so as to define and surrounds a helical tissue-coupling element channel 751 that extends to a distal end 753 of helical tissue-coupling element 750; and
a proximal anchor head 752, which (a) is attached to a proximal portion 754 of helical tissue-coupling element 750, and (b) is shaped so as to define a head-coupling channel 756, which has an internal wall 758 (labeled in FIG. 14l). Helical tissue-coupling element 750 is configured to puncture and screw into cardiac tissue.

It is noted that proximal anchor head 752 of tissue anchor 724 is typically shorter than proximal anchor head 52 of tissue anchor 24, described hereinabove with reference to FIGS. 1A-3E. The shorter anchor head allows tissue anchor 724 to be drawn closer to another tissue anchor when tension is applied using a tether, than can be achieved with tissue anchor 24. In addition, when two tissue anchors 724 are used, they can be drawn even closer to one another when tension is applied using a tether, than can be achieved with two tissue anchors 24.

For some applications, helical tissue-coupling element 750 implements features of one or more of the tissue-coupling elements described in PCT Application PCT/IL2014/050027, filed Jan. 9, 2014, which published as PCT Publication WO 2014/108903 and is incorporated herein by reference.

Typically, tissue-anchor system further comprises tether 22, which is coupled (optionally, fixed) to anchor head 752, and which typically is tensioned after tissue anchor 724 has been implanted in cardiac tissue.

Torque-delivery cable 728 and distal torque-delivery head 730 together are shaped so as to define a locking-wire-accepting channel 760 (labeled in FIGS. 13B and 14B). Locking-wire-accepting channel 760 passes through (i) torque-delivery cable 728, (ii) chamber 732 (and, typically, the entire distal torque-delivery head 730), and (iii) proximal and distal chamber end openings 738 and 740. In addition, locking-wire-accepting channel 760 is typically coaxial with helical tissue-coupling element channel 751.

Tissue-anchor system 710 is configured to assume engaged and disengaged states, in which distal torque-delivery head 730 is engaged and not engaged to anchor head 752, respectively. Tissue-anchor system 710 is in:
the engaged state when locking shaft 726 is removably disposed in locking-wire-accepting channel 760 and at least partially within helical tissue-coupling element channel 751, with locking shaft 726 constraining coupling element 741 to partially protrude through fenestration 734 out of chamber 732 and against internal wall 758 of head-coupling channel 756, thereby axially locking distal torque-delivery head 730 with respect to head-coupling channel 756, as shown in FIGS. 12A-C, and
the disengaged state when locking shaft 726 is not disposed in locking-wire-accepting channel 760 and is not disposed in helical tissue-coupling element channel 751, and does not constrain coupling element 741, as shown in FIGS. 13A-B and 14A-B.

As mentioned above, FIGS. 13A-B and 14A-B show tissue-anchor system 710 in the disengaged state. In FIGS. 13A-B, tissue-anchor system 710 is shown in the disengaged state, while distal torque-delivery head 730 is still in head-coupling channel 756 of anchor head 752. As can be seen, coupling element 741 has fallen away from internal wall 758 of head-coupling channel 756, such that coupling element 741 no longer axially locks distal torque-delivery head 730 with respect to head-coupling channel 756. This allows the removal of distal torque-delivery head 730 from head-coupling channel 756 of anchor head 752, as shown in FIGS. 14A-B. It is noted that, as shown in both FIGS. 13A-B and 14A-B, coupling element 741 is trapped in chamber 732 because the coupling element is too large to pass through fenestration 734 and too large to pass through distal chamber end opening 740, and, typically, proximal chamber end opening 738. Coupling element 741 thus cannot be released into the patient's body.

For some applications, coupling element 741 is spherical (as shown), and may, for example, have a diameter $D_{CE}$ of at least 0.3 mm, no more than 3 mm, and/or between 0.3 and 3 mm. For some applications, coupling element 741 has a volume of at least 0.3 mm3, no more than 8 mm3, and/or between 0.3 and 8 mm3. For some applications, coupling element 741 comprises a metal. For other applications, coupling element 741 comprises a polymer, such as an elastomer.

Typically, internal wall 758 of head-coupling channel 756 is shaped so as to define a coupling indentation 762. Tissue-anchor system 710 is in the engaged state when locking shaft 726 is removably disposed in locking-wire-accepting channel 760 and at least partially within helical tissue-coupling element channel 751, with locking shaft 726 constraining coupling element 741 to partially protrude through fenestration 734 out of chamber 732 and into coupling indentation 762 of the internal wall 758 of head-coupling channel 756.

For some applications, torque-delivery tool 720 further comprises a depth-finding tool 764, which comprises a radiopaque bead 766 shaped so as to define a hole 768 therethrough (labeled in FIGS. 139 and 149). Bead 766 is removably positioned within helical tissue-coupling element channel 751. Locking shaft 726 passes through hole 768 of bead 766, such that bead 766 is slidable along locking shaft 726 and along helical tissue-coupling element channel 751, when locking shaft 726 is removably disposed at least partially within helical tissue-coupling element channel 751 when tissue-anchor system 710 is in the engaged state. For some applications, depth-finding tool 764 further comprises a bead-coupling wire 770, which is at least partially removably disposed within helical tissue-coupling element channel 751, and which is fixed to bead 766 and a distal portion 772 of distal torque-delivery head 730 (labeled in FIGS. 13B and 14A), thereby (a) preventing bead 766 from exiting a distal end 774 of helical tissue-coupling element channel 751, and (b) facilitating removal of depth-finding tool 764 from tissue anchor 724 upon removal of distal torque-delivery head 730 from anchor head 752. For some applications, bead-coupling wire 770 is shaped as a helical spring 776, such as shown.

For some applications, depth-finding tool 764 implements techniques described in PCT Publication WO 2014/108903, which is incorporated herein by reference. For example, bead 766 serves as a marker that indicates a depth of penetration of helical tissue-coupling element 750 into soft tissue, such as cardiac tissue. When rotated, helical tissue-coupling element 750 penetrates and is advanced into the tissue. Bead 766 does not penetrate the tissue, and thus remains at the surface of the tissue, in contact therewith. As a result, as the tissue-coupling element advances into the tissue, the bead remains stationary, and moves toward a proximal end of tissue anchor 724 (and toward anchor head 752 and distal torque-delivery head 730). In other words, the proximal end of tissue anchor 742 (and anchor head 752 and distal torque-delivery head 730) move closer to bead 766, as measured along a central longitudinal axis of tissue anchor 742.

Both the bead and more proximal portions of the anchor (such as anchor head 752) are viewed using imaging (e.g., fluoroscopy, computed tomography, echocardiography, sonography, or MRI), and the distance between the bead and the proximal end of the tissue anchor (e.g., the anchor head) is estimated and monitored in real time as the anchor is advanced into the tissue. When the bead reaches a desired distance from the head (such as reaches the head itself), the tissue-coupling element has been fully advanced, e.g., screwed, into and embedded in the tissue, and the physician thus ceases rotating the anchor.

Without using a technique such as this for visualizing the advancement of the anchor into the tissue, it is often difficult to ascertain when the tissue anchor has been fully embedded into the tissue, because the tissue is difficult to see in some images, such as fluoroscopic images. As a result, the tissue anchor may inadvertently be insufficiently advanced into the tissue, resulting in poor anchoring in the tissue, or overadvanced into the tissue, possible tearing or otherwise damaging the tissue.

Bead 766 may have any appropriate shape, such as a sphere (as shown) or a disc (not shown). An outer diameter of the bead is typically slightly greater than the inner diameter of an empty space within helical tissue-coupling element 750, in order to provide some friction between the bead and helical tissue-coupling element 750, and prevent the bead from being free-floating within the helix. For example, the outer diameter of the bead may be at least 0.05 microns less than the inner diameter of the empty space. Alternatively or additionally, the bead comprises a coating which provides some friction between the bead and the helix; the coating may be sheared off as the bead moves proximally through the helix. Further alternatively or additionally, the bead and shaft are configured to provide some friction therebetween. For some applications, the outer diameter of the bead may be between 1 and 5 mm.

FIGS. 13A-B show helical spring 776 axially compressed, with bead 766 as close as possible to anchor head 752 and distal torque-delivery head 730. As mentioned above, such a state is reached when bead 766 pushes against tissue. Although the tissue is not shown in FIGS. 13A-B, FIGS. 13A-B nevertheless show helical spring 776 axially compressed, because the spring is typically in this state upon and after removal of locking shaft 726, which removal is performed after the anchor has been implanted in the tissue and the tissue has pushed the bead up against the anchor head.

For some applications, anchor head 752 is shaped so as to define a tether-securing element 780, which is typically shaped so as to define a lateral opening 782 through which tether 22 is disposed. For some applications, tether-securing element 780 is rotatable with respect to helical tissue-coupling element 750, in order to provide rotational freedom of movement to tether 22 after implantation of tissue anchor 724, particularly during tensioning of tether 22. This rotational freedom of movement avoids twisting of the tether around anchor head 752, and facilitates ideal orientation of the tether with another tissue anchor.

Tissue-anchor system 710 is advanced into the heart in the engaged state. Tissue anchor 724 is implanted in cardiac tissue, using torque-delivery cable 728 while tissue-anchor system 710 is in the engaged state. Typically, as tissue anchor 724 is screwed into the tissue, locking shaft 726, which is disposed within locking-wire-accepting channel 760 and helical tissue-coupling element channel 751, penetrates and advances into the tissue along with the tissue anchor. For some applications, when the locking shaft penetrates to a certain depth, the locking shaft is withdrawn slightly. Optionally, sharp distal tip 727 of locking shaft 726 is inserted into the tissue slightly, even before insertion of tissue anchor 724, in order to prevent sliding of the anchor on the surface of the tissue before commencement of insertion of the anchor into the tissue.

After tissue anchor 724 has been fully implanted, locking shaft 726 is withdrawn entirely from the tissue, from helical tissue-coupling element channel 751, and from locking-wire-accepting channel 760, thereby allowing the disengagement of distal torque-delivery head 730 from anchor head 752, as described hereinabove with reference to FIGS. 13A-B and 14A-B. Because depth-finding tool 764 is fixed to distal torque-delivery head 730, removal of distal torque-delivery head 730 from anchor head 752 removes depth-finding tool 764, including radiopaque bead 766, from tissue anchor 724. Removal of radiopaque bead 766 from the empty space within helical tissue-coupling element 750 allows for greater integration of the helical tissue-coupling element with cardiac tissue. In addition, for applications in which bead-coupling wire 770 is shaped as helical spring 776, as described above, removal of radiopaque bead 766 and helical spring 776 prevents the radiopaque bead and the spring from compressing the tissue in the space within the helical tissue-coupling element on a long-term basis.

Figure 15:
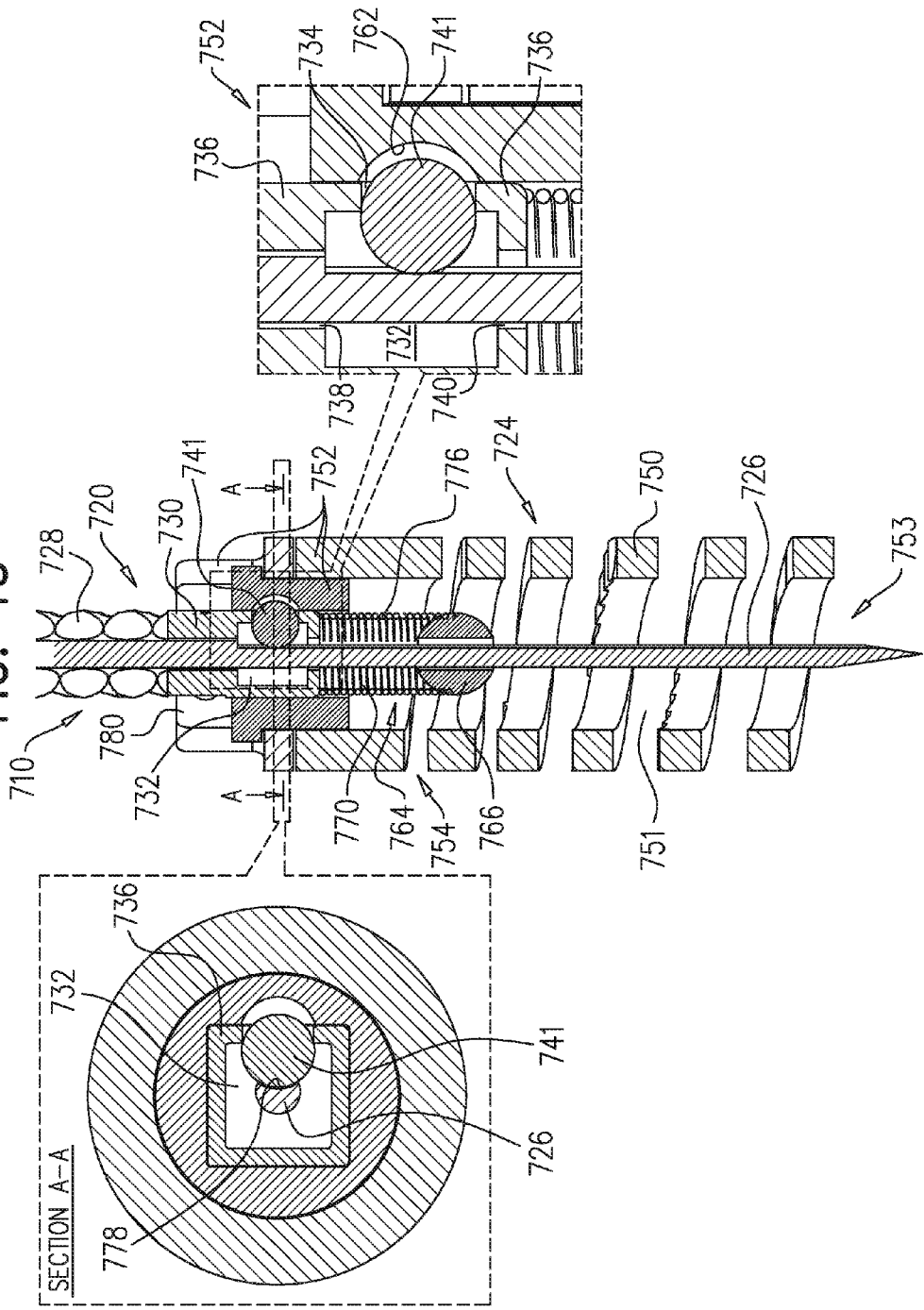
FIG. 15 is a schematic illustration of another configuration of the tissue anchor system of FIGS. 12A-C, in accordance with an application of the present invention.

Reference is now made to FIG. 15, which is a schematic illustration of another configuration of tissue anchor system 710, in accordance with an application of the present invention. In this configuration, locking shaft 726 is shaped so as to define one or more longitudinally-extending grooves 778, such as exactly one groove 778 as shown in FIG. 15. Alternatively, for some applications, locking shaft 726 is shaped so as to define one or more longitudinally-extending flat surfaces, such as a plurality of longitudinally-extending flat surfaces facing in respective different directions (for example, locking shaft 726 may be polygonal in cross-section, such as hexagonal) (configurations not shown). The groove or flat surface helps better seat and secure coupling element 741, by providing a greater contact surface area between the shaft and the coupling element. The groove or flat surface also allows for the use of a larger coupling element 741, which may also increase the contact surface area between the shaft and the coupling element. The groove or flat surface may also prevent rotation of the shaft with respect to torque-delivery cable and anchor 724.

Figure 16A:
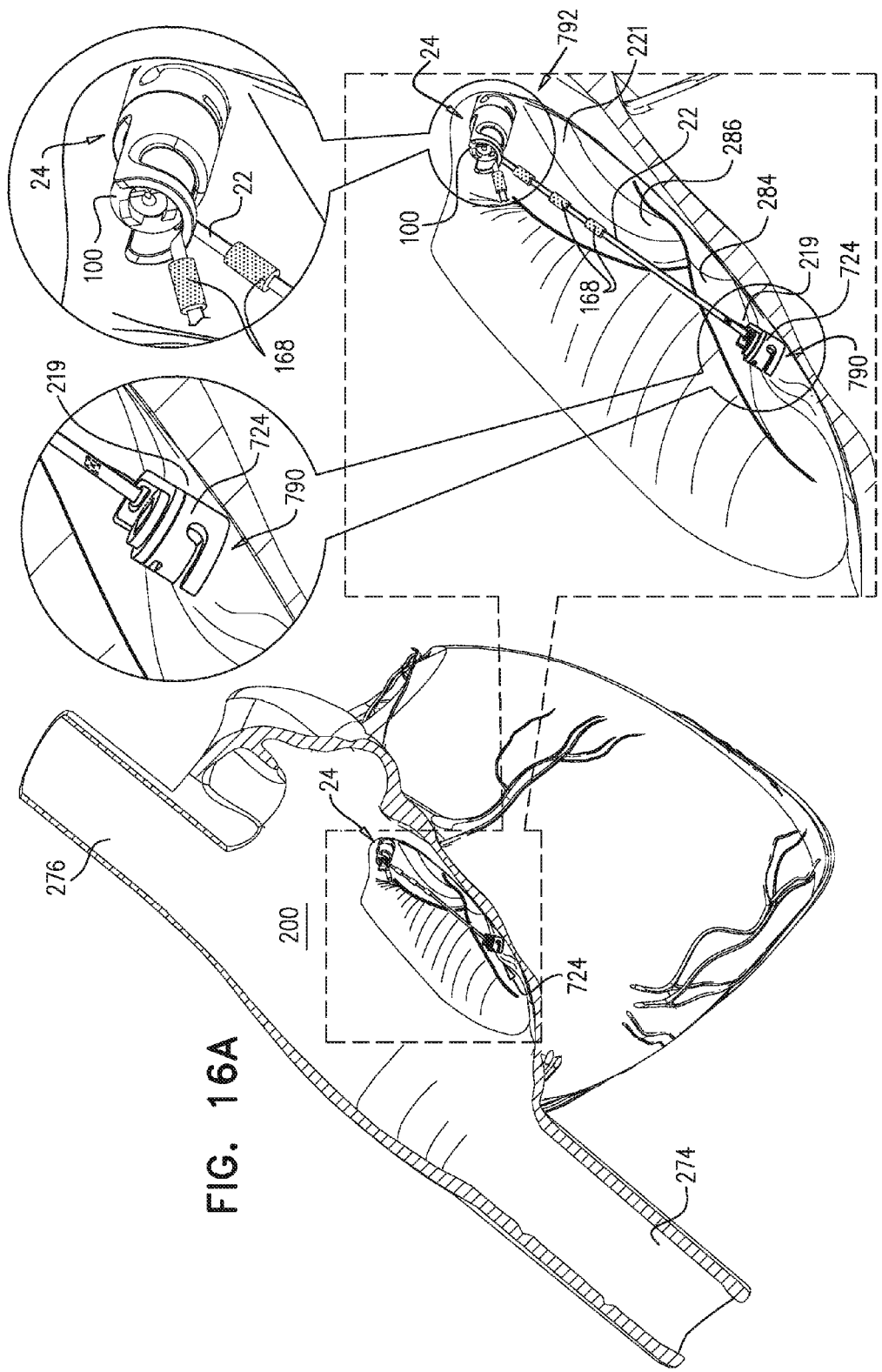
Figure 16B:
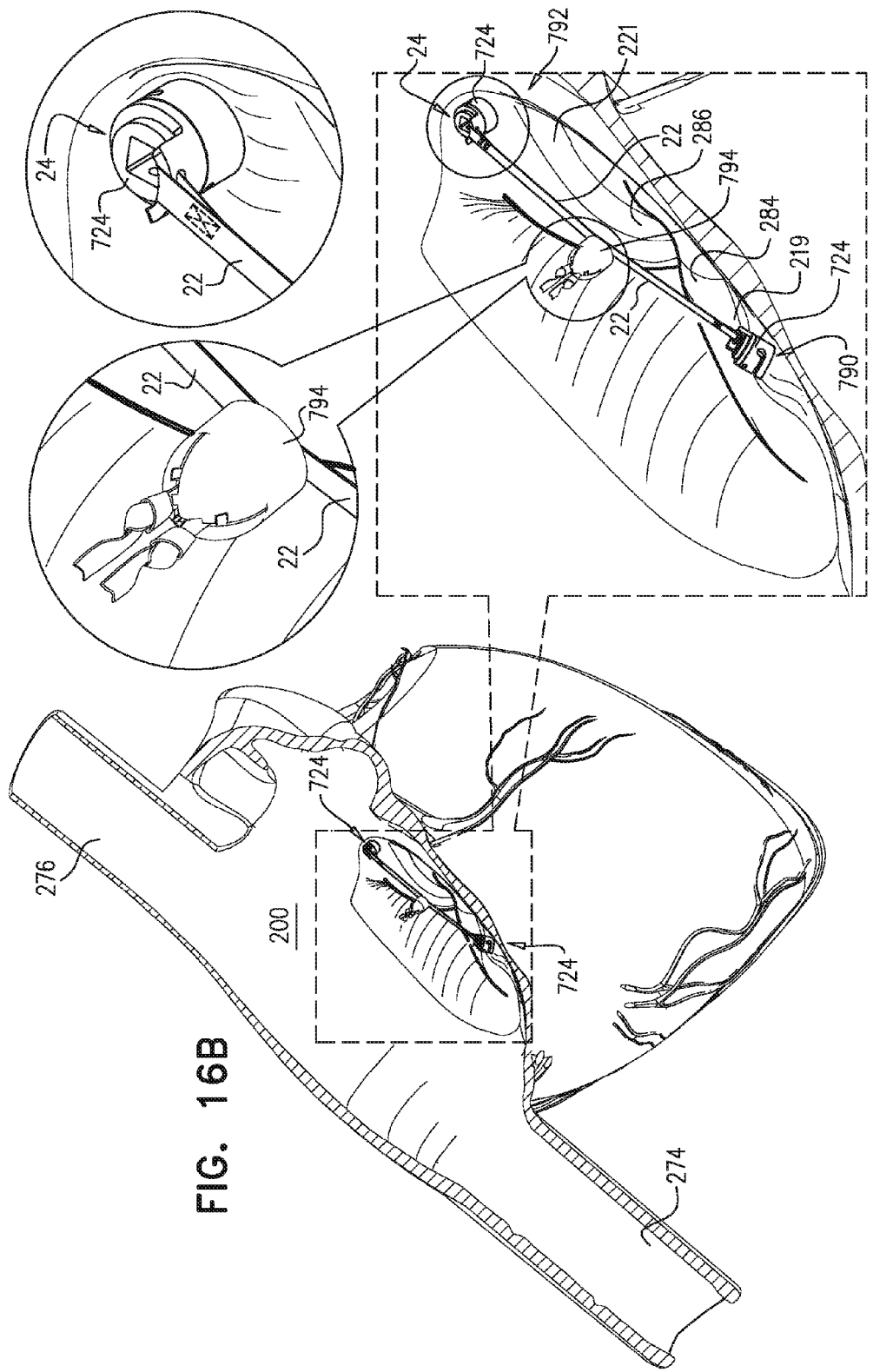

Reference is now made to FIGS. 16A-C, which are schematic illustrations of three exemplary deployments of tissue anchor 724 using torque-delivery tool 720, in accordance with respective applications of the present invention. These deployments may be performed using techniques described hereinabove with reference to FIGS. 5A-D mutatis mutandis, and/or described in the patent applications incorporated hereinbelow by reference, mutatis mutandis.

In the deployment illustrated in FIG. 16A, tissue anchor 724, described hereinabove with reference to FIGS. 12A-149, is shown deployed at a first atrial site 790, and tissue anchor 724, described hereinabove with reference to FIGS. 1A-F, 2A-B, 3A-E, and 5A-D, is shown deployed at a second atrial site 792. Tether 22 is tensed as described hereinabove regarding tissue anchor 724.

In the deployment illustrated in FIG. 16B, two tissue anchors 724, described hereinabove with reference to FIGS. 12A-14B, are shown deployed at first and second atrial sites 790 and 792, respectively. Respective tethers 22 are fixed to heads of tissue anchors 724, and are coupled together in tension by a tether-securing device 794. For example, tether-securing device 794 may comprise (a) tether-securing device 330, described with reference to FIGS. 6A-9 of U.S. application Ser. No. 14/525,668, filed Oct. 28, 2014, which published as US Patent Application Publication 2015/0119936 and is assigned to the assignee of the present application and is incorporated herein by reference, or (b) tether-securing device 30, described with reference to FIGS. 1-3 of the '668 application. Techniques for deploying the tether-securing device may be used that are described in the '668 application. Alternatively, a single tissue anchor 724 is deployed, and a second tissue anchor comprises second tissue anchor 252B fixed to tether-securing device 230, both of which are described with reference to FIGS. 4A-5 of the '668 application.

In the deployment illustrated in FIG. 16C, two tissue anchors 724, described hereinabove with reference to FIGS. 12A-14B, are shown deployed at first and second atrial sites 790 and 792, respectively. Tether 22 is provided with securement protrusions 160, which are described hereinabove with reference to FIGS. 4A-E. Tether 22 is fixed to the head of the tissue anchor 724 at first atrial site 790, and passes through lateral opening 782 of tether-securing element 780 of head 752 of the tissue anchor 724 at second atrial site 792. A tether-locking element 796, typically separate from head 752, is provided. Tether 22 passes through tether-locking element 796. Tether-locking element 796 is configured to allow advancement of securement protrusions 160 through tether-locking element 96 in one direction, and inhibit (typically prevent) advancement of the tether through the tether-locking element in the opposite direction. As a result, as tension is applied to tether 22 by pulling on the tether in a direction indicated by an arrow 798, one or more of securement protrusions 160 pass through tether-locking element 796 in the direction indicated by arrow 798, and are prevented from returning through the tether-locking element in the opposite direction, thereby maintaining the tension applied to the tether. Although securement protrusions 160 are shown in FIG. 16C comprising cylinders 168, the securement protrusions may alternatively comprise the other configuration described hereinabove with reference to FIGS. 4B-E or other configurations.

Reference is now made to FIGS. 17A-19, which are schematic illustrations of a flexible tether 822, in accordance with an application of the present invention. FIG. 17C shows tether 822 straight-on from the side. FIGS. 18A-B are cross-sectional views of tether 822 taken along lines XVIIA-XVIIA and XVIIB-XVIIB, respectively, of FIG. 17A. FIG. 19 shows the cross-sectional views of FIGS. 18A-B superimposed on one another for illustrative purposes. Tether 822 may be used, for example, to apply tension between two or more tissue anchors, such as tissue anchors described herein, and/or in the patent applications incorporated by reference hereinbelow. Typically, tether 822 is sterile when provided, typically in protective packaging.

Tether 822, at least when tensioned into a straight, non-twisted configuration, such as shown in FIGS. 17A-19, has a central longitudinal axis 828, and is shaped so as to define first and second blades 830A and 830B (and, typically, at least several more blades), which are disposed (a) at first and second longitudinal locations 832A and 832B, and (b) within 10 mm of one another along central longitudinal axis 828. By "within 10 mm of one another" it is meant that respective portions of the blades that are closest to one another along the axis are within 10 mm of one another; "within 10 mm" does not refer to a distance between respective longitudinal centers of the blades. For some applications, first and second blades 830A and 830B are disposed within 5 mm of one another along central longitudinal axis 828, such as touching one another (as shown in FIGS. 17A-C).

First and second blades 830A and 830B have respective best-fit planes 834A and 834B, which intersect at an angle θ (theta) of at least 30 degrees, such as at least 60 degrees, e.g., at least 85 degrees, for example 90 degrees (as shown). In other words, adjacent first and second blades 830A and 830B are rotationally offset by at least angle θ (theta). For example, for applications in which angle θ (theta) equals 90 degrees, the blades may be considered to have two rotational phases, while for other applications in which angle θ (theta) is less than 90 degrees, the blades may be considered to have three or more rotational phases. Typically, each of the blades defines two opposing generally flat external surfaces that are generally parallel with the blade's best-fit plane.

As used in the present application, including the claims, a "blade" of tether 822 is a generally flat thin part or section. A "blade" does not necessarily define a sharp cutting edge, and, in fact, blades 830 do not generally define any sharp cutting edges.

As used in the present application, including in the claims, a "best-fit plane" of a given blade is the plane that results in the minimum sum of squares of distances between the plane and all points of the volume of the blade. As used in the present application, including in the claims, an angle between two lines or two planes is the smaller of the two supplementary angles between the two lines or two planes, or equals 90 degrees if the two lines or two planes are perpendicular. As used in the present application, including in the claims, a "non-twisted configuration" means that the tether is not twisted, i.e., not altered in shape, as by turning the ends in opposite directions, so that parts previously in the same straight line and plane are located in a spiral curve, as might occur if the tether were twisted.

As used in the present application, including in the claims, a "central longitudinal axis" of an elongate structure is the set of all centroids of transverse cross-sectional sections of the structure along the structure. Thus the cross-sectional sections are locally perpendicular to the central longitudinal axis, which runs along the structure. (If the structure is circular in cross-section, the centroids correspond with the centers of the circular cross-sectional sections.)

For some applications, central longitudinal axis 282 falls in first and second best-fit planes 834A and 834B (as shown). For some other applications, central longitudinal axis 282 is parallel to first and second best-fit planes 834A and 834B (configuration not shown).

For some applications, a plane defined by a longitudinal edge 836 of first blade 830A forms an angle with central longitudinal axis 828 of at least 60 degrees, such as 90 degrees. For some applications, the longitudinal edge includes a flat portion, or is entirely flat. Another edge of first blade 830A, as well edges of the other blades 830, may also have one or more of these properties.

First and second blades 830A and 830B have respective first and second greatest dimensions $D_{GA}$ and $D_{GB}$ perpendicular to central longitudinal axis 828. For some applications, each of first and second greatest dimensions $D_{GA}$ and $D_{GB}$ is at least 0.25 mm (e.g., at least 0.5 mm), no more than 5 mm, and/or between 0.5 and 5 mm (e.g., between 0.25 and 5 mm).

For some applications, first and second greatest dimensions $D_{GA}$ and $D_{GB}$ are first and second greatest major dimensions $D_{GA}$ and $D_{GB}$, and first and second blades 830A and 830B have respective first and second greatest minor dimensions $D_{MA}$ and $D_{MB}$, which are measured perpendicular to (a) first and second greatest major dimensions $D_{GA}$ and $D_{GB}$, respectively, and (b) central longitudinal axis 828. First and second greatest minor dimensions $D_{MA}$ and $D_{MB}$ typically equal no less than 10% (e.g., no less than 25%), no more than 90% (e.g., no more than 50%), and/or between 10% and 90%, such as between 25% and 50% of first and second greatest major dimensions $D_{GA}$ and $D_{GB}$, respectively. For some applications, each of first and second greatest minor dimensions $D_{MA}$ and $D_{MB}$ is at least 0.05 mm, such as at least 0.1 mm, or no more than 3 mm, such as between 0.05 mm (e.g., 0.1 mm) and 3 mm.

As labeled in FIG. 17C, first and second blades 830A and 830B have first and second lengths $L_A$ and $L_B$, respectively, which are measured along central longitudinal axis 828. For some applications, each of first and second lengths $L_A$ and $L_B$ is at least 0.25 mm (e.g., at least 0.5 mm), no more than 10 mm (e.g., no more than 5 mm), and/or between 0.25 and 10 mm, such as between 0.5 mm and 5 mm, typically between 1 and 5 mm.

Typically, tether 822 is shaped so as to define at least two, no more than 50, and/or between two and 50 blades 830, such as at least 10, no more than 30, and/or between 10 and 30 blades 830. These blades 830 include first and second blades 830A and 830B, and a third blade 830C, which is disposed (a) at a third longitudinal location 832C, and (b) within 10 mm of second blade 830B along central longitudinal axis 828. Second longitudinal location 832B is longitudinally between first and third longitudinal locations 832A and 832C along central longitudinal axis 828. Third blade 830C has a third best-fit plane, which intersects second best-fit plane 834B at an angle of at least 30 degrees, when tether 822 is tensioned into the straight, non-twisted configuration.

For some applications, first blade 830A is shaped so as to define at least one flat planar surface portion 840 having a cross-sectional area of at least 025 mm2 (labeled in FIG. 18A). For some applications, first blade 830A is shaped so as to define at least two non-coplanar flat planar surface portions 840 and 842, each of which has the area of at least 0.25 mm2. For some applications, the at least two flat planar surface portions 840 and 842 are parallel to one another (such as shown). For some applications, second blade 830B is shaped so as to define at least one flat planar surface portion 844 having a cross-sectional area of at least 0.25 mm2 (labeled in FIG. 18B).

For some applications, first and second blades 830A and 830B have a same shape, which has different rotational orientations about central longitudinal axis 828 at first and second longitudinal locations 832A and 832B (such as shown). For other applications, first and second blades 830A and 830B have different shapes (configuration not shown).

For some applications, tether 822 comprises a polymer. For some applications, tether 822 comprises a polymer/metal composite material. In some applications, the tether is radiopaque such that it is visible under fluoroscopy. For example, the metal may comprise a precious metal or a heavy metal. The radiopaque material may be encapsulated in the tether or may be an independent layer embedded in the structure, such as a wire running along the central longitudinal axis of the tether. The metal component may also be configured to vary in diameter and/or material from the distal end to the proximal end of the tether. A proximal portion of the tether composite may be constructed to be stiff to allow effective torque delivery, and a distal portion of the tether may be constructed to be more flexible and allow for cutting of the tether in situ, for example using cutting tool 600, described hereinabove with reference to FIGS. 11A-D or another cutting tool.

For some applications, first and second blades 830A and 8309 have respective first and second greatest cross-sectional areas, measured perpendicular to central longitudinal axis 828, each of which is at least 0.1 mm2, no more than 20 mm2, and/or between 0.1 and 20 mm2, such as at least 0.5 mm2, no more than 5 mm2, and/or between 0.5 and 5 mm2. For some applications, the first and the second greatest cross-sectional areas are equal. For some applications, first and second blades 830A and 830B have respective first and second volumes, each of which is at least 0.05 mm3, no more than 150 mm3, and/or between 0.05 and 150 mm3, such as at least 0.25 mm3, no more than 15 mm3, and/or between 0.25 and 15 mm3.

For some applications, tether 822 is shaped so as to define at least three blades 830, which include first and second blades 830A and 830B, and which are disposed along a longitudinal portion of tether 822. For some applications, an average cross-sectional area of tether 822 along the longitudinal portion is less than 20 mm2, such as less than 4 mm2, and/or a greatest cross-sectional area of tether 822 along the longitudinal portion is less than 20 mm2.

For some applications, a longitudinal portion of tether 822 includes (a) a bladed sub-portion, which is shaped so as to define blades 830, and (b) a non-bladed sub-portion, which is not shaped so as to define any blades 830. The longitudinal portion has a constant cross-sectional area, measured perpendicular to central longitudinal axis 828. For some applications, tether 822 is manufactured by taking a tether that initially has a circular cross-sectional shape, and shape-setting longitudinal portions of the circular tether so as to form blades 830. For some applications, the shape-setting includes flattening and twisting the circular tether, to produce the shape shown in FIGS. 17A-C, which includes short twisted portions at the interfaces between adjacent blades. For other applications, the shape-setting includes flattening portions of the circular tether, to produce the shape shown in FIGS. 21A-C.

For some applications, blades 830 have a hardness of at least 40 Shore D. For some applications in which the tether includes one or more non-bladed sub-portions, the one or more non-bladed sub-portions have the same hardness as blades 830.

Reference is now made to FIGS. 20A-C, which are schematic illustrations of cross sections of tether 822, in accordance with an application of the present invention. For some applications, when tether 822 is tensioned into a straight (typically non-twisted) configuration, tether 822 has central longitudinal axis 828, and is shaped so as to define first and second cross sections 850A and 850B perpendicular to central longitudinal axis 828, at first and second different longitudinal locations 832A and 832B that are within 10 mm of one another along central longitudinal axis 828. First and second cross sections 850A and 850B have respective first and second greatest dimensions $D_{GA}$ and $D_{GB}$, which define respective first and second lines 852A and 852B. If first and second cross sections 850A and 850B were to be projected onto one another while preserving rotation about central longitudinal axis 828, as shown in FIG. 20C, (a) first and second lines 852A and 852B would intersect at an angle $\epsilon$ (epsilon) of at least 30 degrees, such as at least 60 degrees, e.g., at least 85 degrees, for example 90 degrees (as shown), and (b) first and second cross sections 850A and 850B would not coincide.

For some applications, when tensioned into the straight, non-twisted configuration, tether 822 is shaped so as to define a third cross section perpendicular to central longitudinal axis 828 at third longitudinal location 832C. The third second cross section has a third greatest dimension, which defines a third line. If second cross section 850B and the third cross section were to be projected onto one another while preserving rotation about central longitudinal axis 828, (a) the second and the third lines would intersect at an angle of at least 30 degrees, and (b) the second and the third cross sections would not coincide.

For some applications, a first perimeter 860A of first cross section 850A is shaped so as to define at least one straight line segment 862 having a length of at least 0.5 mm. For some applications, first perimeter 860A is shaped so as to define at least two non-coaxial straight line segments 862 and 864, each of which has the length of at least 0.5 mm. For some applications, the at least two non-coaxial straight line segments 862 and 864 are parallel to one another (such as shown). For some applications, a second perimeter 860B of second cross section 850B is shaped so as to define at least one straight line segment 866 having a length of at least 0.5 mm.

For some applications, first and second cross sections 850A and 850B have a same shape, which has different rotational orientations about central longitudinal axis 828 at first and second longitudinal locations 832A and 832B.

For some applications, when tensioned into the straight, non-twisted configuration, tether 822 is shaped so as to define a first longitudinal segment 870A (labeled in FIG. 17C) that includes first longitudinal location 832A and has a first length $L_A$ of at least 0.25 mm (e.g., at least 0.5 mm), no more than 10 mm (e.g., no more than 5 mm), and/or between 0.25 and 10 mm, such as between 0.5 mm and 5 mm, typically between 1 and 5 mm. First length $L_A$ is measured along central longitudinal axis 828, and corresponds to first length $L_A$ described hereinabove regarding first blade 830A. First longitudinal segment 870A, at every longitudinal location therealong, has first cross sections, which (a) include first cross section 850A, and (b) have respective first greatest dimensions, which define respective first lines, which include the first line 852A. If the first cross sections were to be projected onto second cross section 850B while preserving rotation about central longitudinal axis 828: (a) the first lines would intersect second line 852B at respective angles, each of at least 30 degrees, and (b) the first cross sections would not coincide with second cross section 850B. For some applications, the first cross sections have a same shape. For some applications, the shape has a same rotational orientation about central longitudinal axis 828 along first longitudinal segment 870A. Alternatively, for some applications, the shape has different rotational orientations about central longitudinal axis 828 at at least two longitudinal locations along first longitudinal segment 870A.

For some applications, when tensioned into the straight, non-twisted configuration, tether 822 is shaped so as to define a second longitudinal segment 870B (labeled in FIG. 17C) that includes second longitudinal location 832B and has a second length $L_B$ of at least 0.25 mm (e.g., at least 0.5 mm), no more than 10 mm (e.g., no more than 5 mm), and/or between 0.25 and 10 mm, such as between 0.5 mm and 5 mm, typically between 1 and 5 mm. Second length $L_B$ is measured along central longitudinal axis 828, and corresponds to second length $L_B$ described hereinabove regarding second blade 830B. Second longitudinal segment 870B, at every longitudinal location therealong, has second cross sections, which (a) include second cross section 850B, and (b) have respective second greatest dimensions, which define respective second lines, which include second line 852B. If the second cross sections were to be projected onto first cross section 850A while preserving rotation about central longitudinal axis 828: (a) the second lines would intersect first line 852A at respective angles, each of at least 30 degrees, and (b) the second cross sections would not coincide with first cross section 850A.

For some applications, first and second cross sections 850A and 850B have first and second areas, respectively, each of which is at least 0.05 mm2, no more than 15 mm2, and/or between 0.05 and 15 mm2.

Reference is now made to FIGS. 21A-C, which are schematic illustrations of another configuration of flexible tether 822, in accordance with an application of the present invention. FIG. 21B shows tether 822 straight-on from the side. FIG. 21C is a cross-sectional view of tether 822 taken along line XXIC-XXIC of FIG. 21A. In this configuration, first and second blades 830A and 830B are separated by a blade-free longitudinal gap 874, which has a length of at least 0.25 mm. Tether 822 is thus narrower along the gap, because no blades are disposed in the gap. For some applications, tether 822 along gap 874 is circular in cross-section. Gaps 874 may be provided between all or a portion of longitudinally-adjacent blades 830 of tether 822. This configuration may be particularly suitable for practicing the techniques described hereinbelow with reference to FIGS. 23A-B.

Figure 22:
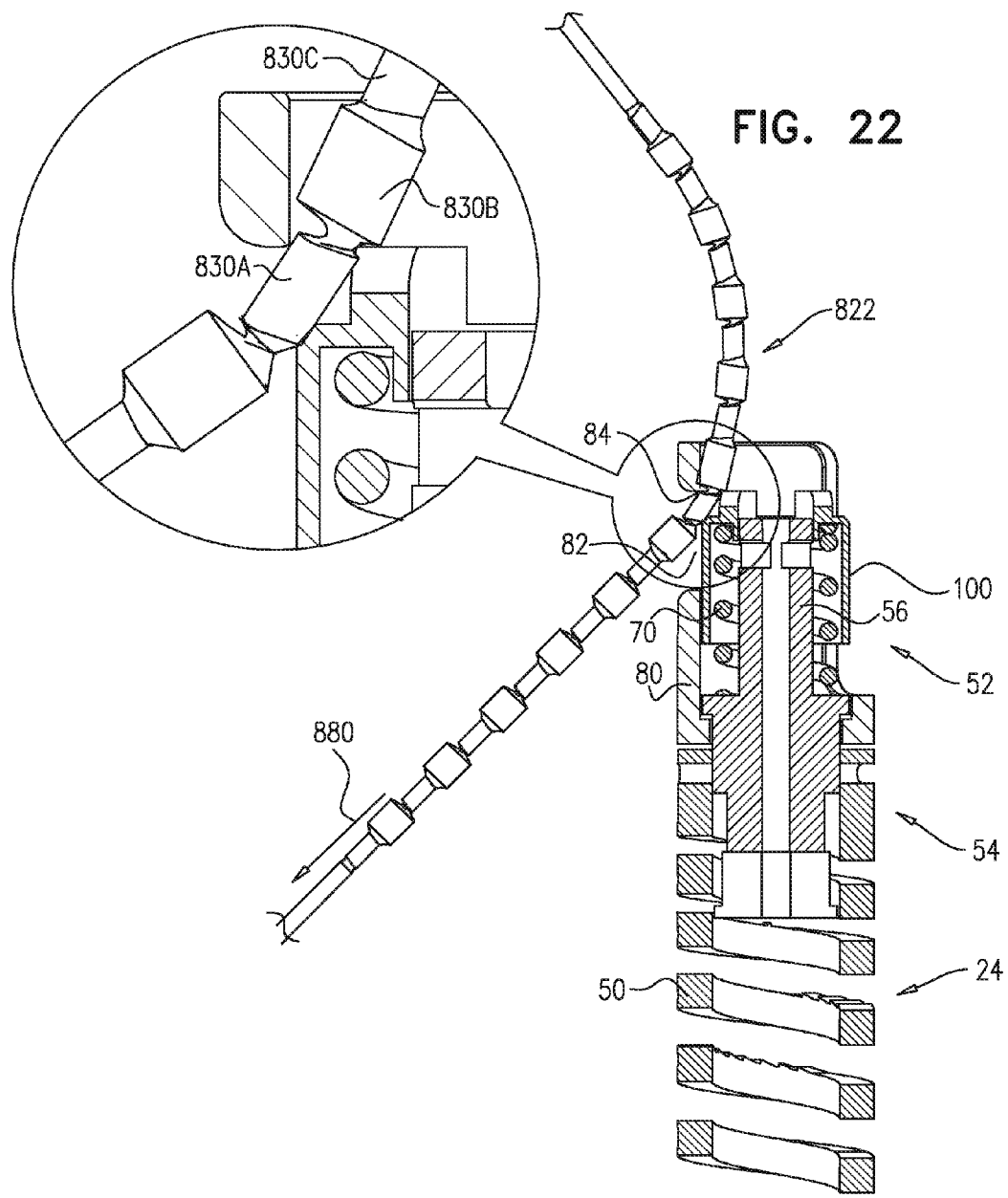
FIG. 22 is a schematic illustration of one use of the flexible tether of FIGS. 20A-C, in accordance with an application of the present invention.

Reference is now made to FIG. 22, which is a schematic illustration of one use of tether 822, in accordance with an application of the present invention. In FIG. 22, tether 822 is shown passing through lateral opening 82 of tissue anchor 24, while tissue anchor system 10 is in the locked state. Tissue anchor system 10 and tissue anchor 24 are described hereinabove with reference to FIGS. 1A-3E. When tissue-anchor system 10 (and tether-locking mechanism 68 thereof) is in the locked state, spring 70 (and, optionally, hammer cap 100) inhibits the sliding of tether 822 through lateral opening 82 by pressing tether 822 against outer tether-securing element 80, such as against perimeter 84 of lateral opening 82, and/or an inner surface of outer tether-securing element 80.

When anchor system 10 transitions from the unlocked state to the locked state, tether 822, at some longitudinal location therealong, is pressed between perimeter 84 of lateral opening 82 (or the inner surface of outer tether-securing element 80) and spring 70 (or hammer cap 100). Spring 70 (or hammer cap 100) impinges on tether 822 and causes the tether to rotate such that the opposing generally flat surfaces of the blade 830 at the longitudinal location (e.g., blade 830A) respectively contact (a) perimeter 84 of lateral opening 82 (or the inner surface of outer tether-securing element 80) and (b) spring 70 (or hammer cap 100). As a result of this rotational alignment, the two adjacent blades 830 (e.g., blades 830A and 830B) are aligned with respect to one another about central longitudinal axis 828 at angle θ (theta), described hereinabove with reference to FIGS. 17A-19, e.g., at least 30 degrees.

When tension is applied to tether 822 in the direction indicated by an arrow 880, the adjacent blade 830 that is opposite the direction of tension (e.g., blade 830B) is pulled against (a) perimeter 84 of lateral opening 82 (or the inner surface of outer tether-securing element 80) and (b) spring 70 (or hammer cap 100). The rotationally-offset orientation of this adjacent blade inhibits passage of this adjacent blade (e.g., blade 830B) through the narrow space between perimeter 84 of lateral opening 82 (or the inner surface of outer tether-securing element 80) and spring 70 (or hammer cap 100).

Figure 23B:
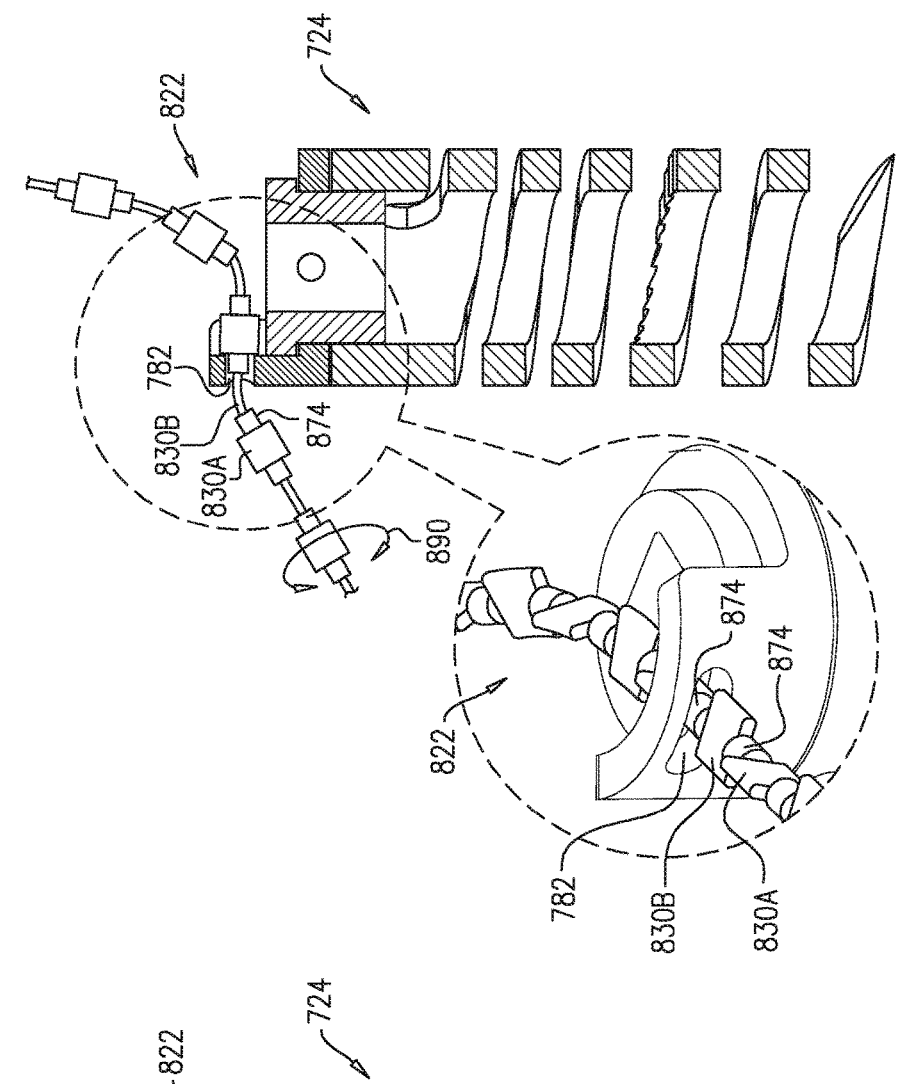
FIGS. 23A-B are schematic illustrations of one use of the flexible tether of FIGS. 21A-C, in accordance with an application of the present invention.
Figure 23A:
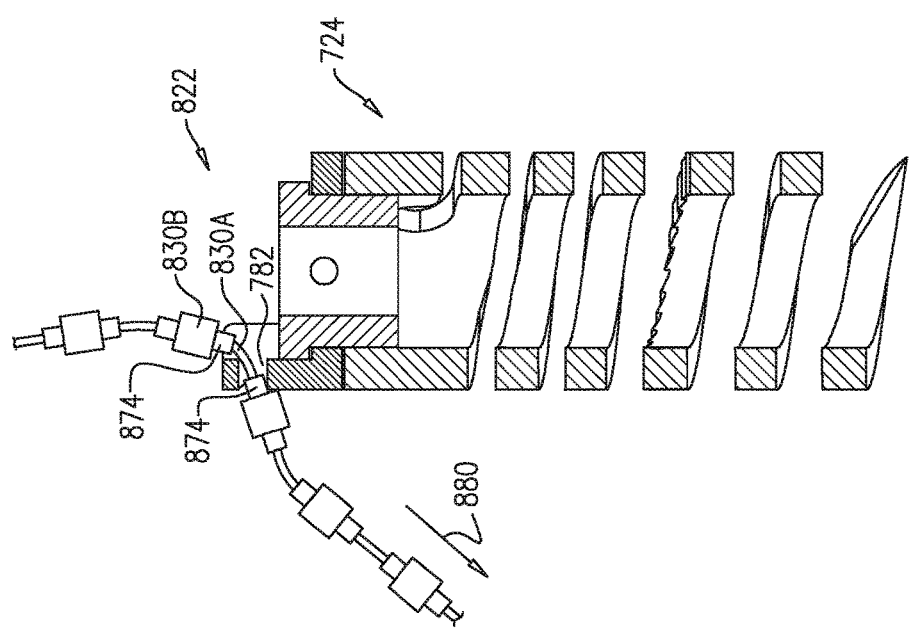

Reference is now made to FIGS. 23A-B, which are schematic illustrations of another use of tether 822, in accordance with an application of the present invention. In FIGS. 23A-B, tether 822, in the configuration described hereinabove with reference to FIG. 21A-C, is shown passing through lateral opening 782 of tissue anchor 724. Lateral opening 782 is fairly narrow, such that the angled orientation of the adjacent blade 830 that is opposite the direction of tension (e.g., blade 830B) inhibits passage of this adjacent blade (e.g., blade 830B) through the opening. The blade-free longitudinal gap 874 between adjacent blades 830 allows for full passage of one blade 830 before the adjacent blade (e.g., blade 830B) contacts the perimeter of the opening.

In order to advance tether 822 with respect to opening 782, either in the direction of arrow 880 or the opposite direction, the physician (a) pulls tether 822, until one of gaps 874 is in opening 782, (b) rotates tether 822, as indicated by an arrow 890, and (c) pulls the tether in the desired direction of advancement. For example, FIG. 23B shows tether 822 after it has been advanced in the direction indicated by arrow 880. As can be seen, the angled orientation of the next adjacent blade 830 that is opposite the direction of tension (e.g., blade 830C) inhibits passage of this adjacent blade (e.g., blade 830C) through the opening. Tether 822 is sufficiently rigid to transmit torque, at least from a longitudinal location of a rotation tool to opening 782.

Reference is now made to FIGS. 24A-C, which are schematic illustrations of one use of tether 822 in the configuration described hereinabove with reference to FIG. 21A-C, in accordance with an application of the present invention. FIGS. 24B-C are cross-sectional views taken along the line XXIVB-XXIVB of FIG. 24A. In FIG. 24A-C, tether 822 is shown passing through lateral opening 82 of tissue anchor 24. FIGS. 24A-B show tissue anchor system 10 is in the unlocked state, and FIG. 24C shows tissue anchor system in the locked state. Tissue anchor system 10 and tissue anchor 24 are described hereinabove with reference to FIGS. 1A-3E, except that in the present configuration, lateral opening 82 is oriented vertically, i.e., has a long axis that is parallel to the axis of the anchor. Lateral opening 82 is typically shaped as a vertical slot.

When anchor system 10 is the unlocked state, lateral opening 82 is not obstructed by spring 70 (or hammer cap 100), and thus allows for passage of tether 822. Tether 822 can only advance through lateral opening 82 when the blade 830 at the opening has the same orientation as the opening. Tether 822 is advanced through the opening to a desired level of tension, as described hereinabove with reference to FIGS. 23A-B. The blade-free longitudinal gap 874 between adjacent blades 830 allows for full passage of one blade 830 before the adjacent blade contacts the perimeter of lateral opening 82.

When anchor system 10 transitions from the unlocked state to the locked state, tether 822, at some longitudinal location therealong, is pressed between the perimeter of lateral opening 82 (or the inner surface of outer tether-securing element 80) and spring 70 (or hammer cap 100). Spring 70 (or hammer cap 100) impinges on tether 822 and causes the tether rotate such that both of the blades adjacent to opening 82 (e.g., blades 830A and 830B in FIG. 24C) become substantially parallel to one another. Blade 830B thus become oriented perpendicular to the long axis of opening 82, and inhibits motion in the direction indicated by arrow 880, when tension is applied to tether 822 in the direction indicated by arrow 880.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. application Ser. No. 12/692,061, filed Jan. 22, 2010, which issued as U.S. Pat. No. 8,475,525;

U.S. application Ser. No. 13/188,175, filed Jul. 21, 2011, which issued as U.S. Pat. No. 8,961,596;

U.S. application Ser. No. 13/485,145, filed May 31, 2012, which issued as U.S. Pat. No. 8,961,594;

U.S. application Ser. No. 13/553,081, filed Jul. 19, 2012, which published as US Patent Application Publication 2013/0018459;

U.S. application Ser. No. 13/574,088, filed Oct. 19, 2012, which published as US Patent Application Publication 2013/0046380;

U.S. application Ser. No. 14/143,355, filed Dec. 30, 2013, which published as US Patent Application Publication 2014/0114390;

U.S. application Ser. No. 14/525,668, filed Oct. 28, 2014, which published as US Patent Application Publication 2015/0119936;

International Application PCT/IL2011/000064, flied Jan. 20, 2011, which published as PCT Publication WO 2011/089601;

International Application PCT/IL2012/000282, filed Jul. 19, 2012, which published as PCT Publication WO 2013/011502;

International Application PCT/IL2013/050470, filed May 30, 2013, which published as PCT Publication WO 2013/179295;

International Application PCT/IL2014/050027, filed Jan. 9, 2014, which published as PCT Publication WO 2014/108903;

International Application PCT/IL2014/050233, filed Mar. 9, 2014, which published as PCT Publication WO 2014/141239;

International Application PCT/IL2014/002351, filed Oct. 28, 2014, which published as PCT Publication WO 2015/063580;

U.S. Provisional Application 61/897,491, filed Oct. 30, 2013;

U.S. Provisional Application 61/897,509, filed Oct. 30, 2013; and

U.S. Provisional Application 62/014,397, filed Jun. 19, 2014.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
   making an opening through an atrial septum at a septal site at least 5 mm from a fossa ovalis;
   endovascularly advancing a first tissue anchor to a left-atrial site selected from the group of sites consisting of: a mitral annular site on an annulus of a mitral valve, and a wall of a left atrium of a heart above the mitral annular site;
   implanting the first tissue anchor at the left-atrial site;
   endovascularly advancing a second tissue anchor to a right-atrial site selected from the group of sites consisting of: a tricuspid annular site on an annulus of a tricuspid valve, and a wall of a right atrium of the heart above the tricuspid annular site;
   implanting the second tissue anchor at the right-atrial site; and
   reducing the size of the tricuspid valve orifice and the size of the mitral valve orifice by approximating the left-atrial site and the right-atrial site by tensioning a tether that passes through the opening of the atrial septum and connects the first and the second tissue anchors.

2. The method according to claim 1, wherein endovascularly advancing the first and the second tissue anchors comprises percutaneously advancing the first and the second tissue anchors to the left- and right-atrial sites, respectively.

3. The method according to claim 1, wherein the mitral annular site circumferentially corresponds to a posterior leaflet of the mitral valve.

4. The method according to claim 3, wherein the mitral annular site circumferentially corresponds to an annular site of the mitral valve, which is characterized by at least one of the following: the annular site is within 1 cm of a lateral scallop (P1) of the posterior leaflet, and the annular site is within 1 cm of a middle scallop (P2) of the posterior leaflet.

5. The method according to claim 1, wherein the tricuspid annular site circumferentially corresponds to an annular site of the tricuspid valve that is (a) at or clockwise to a point on the tricuspid annulus 2 cm counterclockwise to an anteroposterior commissure (APC) of the tricuspid valve, and (b) at or counterclockwise to a posteroseptal commissure of the tricuspid valve, as viewed from the right atrium.

6. The method according to claim 1,
   wherein the mitral annular site circumferentially corresponds to a posterior leaflet of the mitral valve, and
   wherein the tricuspid annular site circumferentially corresponds to an annular site of the tricuspid valve that is (a) at or clockwise to a point on the tricuspid annulus 2 cm counterclockwise to an anteroposterior commissure (APC) of the tricuspid valve, and (b) at or counterclockwise to a posteroseptal commissure of the tricuspid valve, as viewed from the right atrium.

7. The method according to claim 1, wherein the septal site is at least 10 mm from the fossa ovalis.

8. The method according to claim 1, wherein the septal site is anterior to the fossa ovalis.

9. The method according to claim 1, wherein the septal site is apical to the fossa ovalis.

10. The method according to claim 1, wherein the septal site is between 3 and 20 mm superior and anterior to a coronary sinus orifice and between 3 and 10 mm posterior to an aorta.

11. The method according to claim 1, wherein implanting the first and the second tissue anchors and tensioning the tether comprises implanting the first and the second tissue anchors and tensioning the tether such that an angle formed in the tether at the opening of the atrial septum is at least 120 degrees.

12. The method according to claim 11, wherein, if the tensioned tether were to be projected onto a coronal plane of the heart, the angle as projected would be at least 120 degrees.

13. The method according to claim 11, wherein, if the tensioned tether were to be projected onto a transverse plane of the heart, the angle as projected would be at least 120 degrees.

14. The method according to claim 1, wherein implanting the first and the second tissue anchors and tensioning the tether comprises implanting the first and the second tissue anchors and tensioning the tether such that (a) a portion of the tensioned tether in the left atrium between the opening of the atrial septum and the first tissue anchor and (b) a plane defined by the annulus of the mitral valve, form an angle of less than 30 degrees.

15. The method according to claim 1, wherein implanting the first and the second tissue anchors and tensioning the tether comprises implanting the first and the second tissue anchors and tensioning the tether such that (a) a portion of the tensioned tether in the right atrium between the opening of the atrial septum and the second tissue anchor and (b) a plane defined by the annulus of the tricuspid valve, form an angle of less than 30 degrees.

16. The method according to claim 1, further comprising placing, in the opening of the atrial septum, an annular reinforcement element that is shaped so as to define an opening therethrough, and wherein the tether passes through the opening of the reinforcement element.

17. The method according to claim 1, wherein endovascularly advancing the second tissue anchor comprises endovascularly advancing the second tissue anchor after implanting the first tissue anchor.

18. The method according to claim 1, wherein endovascularly advancing the first tissue anchor comprises endovascularly advancing the first tissue anchor after implanting the second tissue anchor.

19. The method according to claim 1, further comprising:
placing a locking mechanism in the opening of the atrial septum; and
transitioning the locking mechanism from an unlocked state to a locked state, wherein the locking mechanism, in the locked state, inhibits sliding of the tether through the locking mechanism, thereby fixing respective distances between the opening of the atrial septum and the first and the second tissue anchors.

20. The method according to claim 19, wherein transitioning the locking mechanism comprises transitioning the locking mechanism from the unlocked state to the locked state after tensioning the tether.

* * * * *